United States Patent
Swanton et al.

(10) Patent No.: US 12,416,051 B2
(45) Date of Patent: Sep. 16, 2025

(54) METHOD OF PREDICTING SURVIVAL RATES FOR CANCER PATIENTS

(71) Applicants: The Francis Crick Institute Limited, London (GB); University College London, London (GB)

(72) Inventors: Robert Charles Swanton, London (GB); Dhruva Biswas, London (GB); Nicholas McGranahan, London (GB); Nicolai Juul Birkbak, Aarhus (DK)

(73) Assignees: The Francis Crick Institute Limited, London (GB); University College London, London (GB)

( * ) Notice: Subject to any disclaimer, the term of this patent is extended or adjusted under 35 U.S.C. 154(b) by 1049 days.

(21) Appl. No.: 17/427,329

(22) PCT Filed: Jan. 30, 2020

(86) PCT No.: PCT/GB2020/050221
§ 371 (c)(1),
(2) Date: Jul. 30, 2021

(87) PCT Pub. No.: WO2020/157508
PCT Pub. Date: Aug. 6, 2020

(65) Prior Publication Data
US 2022/0136063 A1    May 5, 2022

(30) Foreign Application Priority Data
Feb. 1, 2019 (GB) .................................... 1901439

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2010/0184063 A1 | 7/2010 | Tsao et al. |
| 2012/0004116 A1* | 1/2012 | Tsao .................. G01N 33/57423 435/6.12 |
| 2014/0227372 A1* | 8/2014 | Missiaglia ........... C12Q 1/6886 424/649 |
| 2018/0002761 A1 | 1/2018 | Jablons et al. |

FOREIGN PATENT DOCUMENTS

| | | |
|---|---|---|
| JP | 2014516531 A | 7/2014 |
| WO | 2010063121 A1 | 6/2010 |
| WO | 2012160177 A1 | 11/2012 |
| WO | 2015138769 A1 | 9/2015 |

OTHER PUBLICATIONS

GEO Accession Viewer (downloaded from the Internet Nov. 1, 2024 at https://www.ncbi.nlm.nih.gov/geo/query/acc.cgi?acc=GPL570). (Year: 2003).*
"International Search Report and Written Opinion corresponding to International Application No. PCT/GB2020/050221 mailed Apr. 24, 2020".
"Search Report corresponding to Application No. GB1901439.8 dated Oct. 18, 2019".
Beer, David G, et al., "Gene-expression profiles predict survival of patients with lung adenocarcinoma", Nature Medicine 8(8):816-824 (Jul. 15, 2002).
Bianchi, Fabrizio , et al., "Survival prediction of stage I lung adenocarcinomas by expression of 10 genes", J. Clin. Invest 117(11):3436-3444 (Nov. 2007).
Biswas, Dhruva , et al., "A Clonal Expression Biomarker Associates With Lung Cancer Mortality", Nat Med. 25(10):1540-1548 (Oct. 1, 2019).
Blackhall, Fiona H, et al., "Stability and Heterogeneity of Expression Profiles in Lung Cancer Specimens Harvested Following Surgical Resection", Neoplasia 6(6):761-767 (Nov./Dec. 2004).
Burrell, Rebecca A, et al., "The causes and consequences of genetic heterogeneity in cancer evolution", Nature 501:338-346 (Sep. 19, 2013).
Das, Kakoli , et al., "NanoString expression profiling identifies candidate biomarkers of RAD001 response in metastatic gastric cancer", ESMO Open 2016;1:e000009. doi:10.1136/esmoopen-2015-000009 (11 pages) (Jan. 2016).
Detterbeck, Frank C, et al., "The Eighth Edition Lung Cancer Stage Classification", Chest 151(1):193-203 (2017).
Djureinovic, Dijana , et al., "Profiling cancer testis antigens in non-small-cell lung cancer", JCI insight 1 (10):86837 (18 pages) (Jul. 7, 2016).
Dobin, Alexander , et al., "STAR: ultrafast universal RNA-seq aligner", Bioinformatics 29(1):15-21 (Oct. 25, 2012).
Durinck, Steffen , et al., "Mapping Identifiers for the Integration of Genomic Datasets with the R/Bioconductor package biomaR!", Nat Protoc 4(8): 1184-1191 ((2009).
Friedman, Jerome , et al., "Regularization Paths for Generalized Linear Models via Coordinate Descent", J Stat Softw. 33(1): 1-22 (Aug. 30, 2010).
Garber, Mitchell E, et al., "Diversity of gene expression in adenocarcinoma of the lung", PNAS 98(24):13784-13789 (Nov. 20, 2001).

(Continued)

*Primary Examiner* — Daniel E Kolker
*Assistant Examiner* — Peter Johansen
(74) *Attorney, Agent, or Firm* — Myers Bigel, P.A.

(57) ABSTRACT

The present invention provides a method for providing a prognosis for a subject with lung cancer, the method comprising: (a) contacting a biological sample from the subject with reagents that specifically bind to each member of a panel of biomarkers comprising ANLN, ASPM, CDCA4, ERRFI1, FURIN, GOLGA8A, ITGA6, JAG1, LRP12, MAFF, MRPS17, PLK1, PNP, PPP1 R13L, PRKCA, PTTG1, PYGB, RPP25, SCPEP1, SLC46A3, SNX7, TPBG, XBP1; (b) determining a riskscore of the subject based on the nucleic acid levels of expression of the biomarkers in the samples; and (c) providing a prognosis for the lung cancer based on the risk score of the subject.

14 Claims, 23 Drawing Sheets

(56) References Cited

OTHER PUBLICATIONS

Geiss, et al., "Direct multiplexed measurement of gene expression with color-coded probe pairs", Nat Biotechnol. 26(3):317-25 (4 pages) (Mar. 2008).
Gentles, Andrew J, et al., "The prognostic landscape of genes and infiltrating immune cells across human cancers", Nat Med 21(8): 938-945 (Aug. 2015).
Gyanchandani, Rekha, et al., "Intra-tumor heterogeneity affects gene expression profile test prognostic risk stratification in early breast cancer", Clin Cancer Res 22(21): 5362-5369 (Nov. 1, 2016).
Jamal-Hanjani, Mariam, et al., "Tracking Genomic Cancer Evolution for Precision Medicine: The Lung TRACERx Study", PLOS Biology 12(7):e1001906 (7 pages) (Jul. 2014).
Jamal-Hanjani, M, et al., "Tracking the Evolution of Non-Small-Cell Lung Cancer", N Engl J Med 376(22):2109-2120 (Jun. 1, 2017).
Kim, Daehwan, et al., "TopHat2: accurate alignment of transcriptomes in the presence of insertions, deletions and gene fusions", Genome Biology 14:R36 (13 pages) (2013).
Kratz, Johannes R, et al., "A practical molecular assay to predict survival in resected nonsquamous, non-small-cell lung cancer: development and international validation studies", Lancet. 379(9818):823-832 (Mar. 3, 2012).
Krystanek, Marcin, et al., "A robust prognostic gene expression signature for early stage lung adenocarcinoma", Biomarker Research 4:4 DOI 10.1186/s40364-016-0058-3 (Feb. 19, 2016) 7 pages.
Kumar-Sinha, Chandan, et al., "Precision oncology in the age of integrative genomics", Nat Biotechnol 36(1):46-60 (Jan. 10, 2018).
Li, Bailiang, et al., "Development and Validation of an Individualized Immune Prognostic Signature in Early-Stage Nonsquamous Non-Small Cell Lung Cancer", JAMA Oncol 3(11):1529-1537 (Jul. 2017).
Li, Bo, et al., "RSEM: accurate transcript quantification from RNA-Seq data with or without a reference genome", BMC Bioinformatics 12:323 (16 pages) (Aug. 4, 2011).
Liao, Yang, et al., "The Subread aligner: fast, accurate and scalable read mapping by seed-and-vote", Nucleic Acids Research 41(10):e108 (17 pages) (Apr. 4, 2013).
Love, Michael, et al., "Moderated estimation of fold change and dispersion for RNA-seq data with DESeq2", Genome Biology 15:550 (21 pages) (Dec. 5, 2014).
Mlecnik, Bernhard, et al., "Comprehensive Intrametastatic Immune Quantification and Major Impact of Immunoscore on Survival", JNCI J Natl Cancer Inst 110(1):97-108 (2018).
Quon, Gerald, et al., "Computational purification of individual tumor gene expression profiles leads to significant improvements in prognostic prediction", Genome Medicine 5:29 (20 pages) (Mar. 28, 2013).
Raz, Dan J, et al., "A Multigene Assay Is Prognostic of Survival in Patients with Early-Stage Lung Adenocarcinoma", Clin Cancer Res 14(17):5565-5570 (Sep. 1, 2008).
Sarkar, I.N., et al., "Characteristic attributes in cancer microarrays", Journal of Biomedical Informatics 35(2):111-122 (Apr. 1, 2002).
Shukla, Sudhanshu, et al., "Development of a RNA-Seq Based Prognostic Signature in Lung Adenocarcinoma", JNCI J Natl Cancer Inst 109(1): djw200 (9 pages) (2017).
Simon, Noah, et al., "Regularization Paths for Cox's Proportional Hazards Model via Coordinate Descent", J Stat Softw 39(5): 1-13 (Mar. 2011).
Subramanian, Jyothi, et al., "Gene Expression-Based Prognostic Signatures in Lung Cancer: Ready for Clinical Use?", J Natl Cancer Inst 102(7):464-474 (Apr. 7, 2010).
Van 'T Veer, Laura J, et al., "Enabling personalized cancer medicine through analysis of gene-expression patterns", Nature 452:564-570 (Apr. 3, 2008).
Vargas, Ashley J, et al., "Biomarker development in the precision medicine era: lung cancer as a case study", Nat Rev Cancer 16(8):525-537 (Aug. 2016).
Wistuba, Ignacio I, et al., "Validation of a Proliferation-based Expression Signature as Prognostic Marker in Early Stage Lung Adenocarcinoma", Clin Cancer Res 19(22):doi:10.1158/1078-0432. CCR-13-0596 (Nov. 15, 2013).
Yachida, Shinichi, et al., "Distant Metastasis Occurs Late during the Genetic Evolution of Pancreatic Cancer", Nature 467(7319): 1114-1117 (Oct. 28, 2010).

\* cited by examiner

METHOD OF PREDICTING SURVIVAL RATES FOR CANCER PATIENTS

STATEMENT OF PRIORITY

This application is a 35 U.S.C. § 371 national phase application of PCT Application PCT/GB2020/050221 filed Jan. 30, 2020, which claims the benefit of British Application No. 1901439.8, filed Feb. 1, 2019, the entire contents of each of which are incorporated by reference herein in its entirety.

FIELD

The invention relates to a method of determining the prognosis of cancer patients and/or predicting treatment response to guide therapeutic options and/or survival rates and/or survival risks and/or clinical outcomes for cancer patients and/or a method of determining whether a therapy is appropriate for a particular cancer patient and/or a method of determining the treatment course (such as a method for stratification of therapy regimen) for cancer patients, particularly those with lung cancers such as non-small cell lung cancer.

BACKGROUND

Lung cancer is the leading cause of global cancer mortality, with non-small cell lung cancer (NSCLC) accounting for 85-90% of cases diagnosed worldwide. As described in "Lung Cancer Stage Classification" by Detterbeck et al published in CHEST 15, 193-203, 2017, tumour stage helps inform the clinical decision to administer adjuvant chemotherapy. However, as described in "Biomarker development in the precision medicine era: lung cancer as a case study" by Vargas et al published in Nat Rev Cancer (2016), TNM stage is an imperfect predictor of survival risk, as patients with the same tumour stage can have markedly different clinical outcomes.

There have been suggestions that cancer patients may be stratified into more precise disease subtypes by incorporating molecular biomarkers, such as gene-expression based correlates of tumour aggressiveness, into current diagnostic criteria. Examples are described in "Enabling personalized cancer medicine through analysis of gene-expression patterns" by Van't Veer et al in Nature 452, 564-570 (2008), "Biomarker development in the precision medicine era: lung cancer as a case study" by Vargas et al in Nat. Rev. Cancer 16, 525-537 (2016) and "Precision oncology in the age of integrative genomics" by Kumar-Sinha et al in Nat. Biotechnol. 36, 46-60 (2018). Accurate identification of patients at high-risk of NSCLC recurrence after surgery may have considerable clinical utility, helping to inform decisions such as whether to administer adjuvant chemotherapy or the required intensity of patient follow-up after surgical resection.

Multiple attempts have been made over the last two decades to derive a prognostic gene expression signature for lung adenocarcinoma (LUAD) patients, the most common histological subtype of NSCLC. Examples are described in "Gene-expression profiles predict survival of patients with lung adenocarcinoma" by Beer et al in Nat Med 8, 816-824 (2002), "A Robust prognostic gene expression signature for early stage lung adenocarcinoma" by Krystanek et al published in Biomark Res 4, 4 (2016) and "Validation of a Proliferation Based Expression Signature as Prognostic Marker in Early Stage Lung Adenocarcinoma" by Wistuba et al published in Clin Cancer Res (2013). However, these efforts have been hindered by poor reproducibility, or limited prognostic power independent of existing clinicopathological risk factors as described for example in "Gene Expression-Based Prognostic Signatures in Lung Cancer; Ready for Clinical Use?" by Subramanian et al in JNCL J Natl Cancer Inst 102, 464-474 (2010).

FIGS. 1a to 1d illustrate some of the problems associated with known signatures. FIG. 1a shows a lung 10 comprising a tumour 12. There are multiple regions R1, R2, R3 and R4 from which a biopsy of the lung can be taken. However, as schematically illustrated in red and blue, biopsies taken from regions R1, R2 and R3 will result in a high risk classification using known prognostic biomarkers and a biopsy taken from region R4 will result in a low risk classification. Typically, in routine clinical practice, diagnosis or prognosis is made using a single biopsy 14. Accordingly, the hypothetical prognostic signature illustrated in FIG. 1a will exhibit a discordant risk classification of the tumour as the result of a biopsy from region R4 is not aligned with the result that would be achieved if the sample was taken from a different region. Thus, the read-out of the signature is vulnerable to tumour sampling bias.

FIG. 1b illustrates the effect of the tumour sampling bias on a patient population. A plurality of lung tumours 20, 22, 24, 26, 28, 30 each having multiple regions (e.g. R1 to R5) for sampling are shown. A prognostic biomarker applied to a biopsy from one of the regions stratifies lung cancer patients 40, 42, 44, 46, 48, 50 into more precise disease subtypes based on estimated survival risk and this may help inform therapeutic decision making. Correctly distinguishing high-risk patients in need of adjuvant chemotherapy from low risk patients for whom surgery alone is curative is important.

In each of the regions of the lung tumours 20, 22, a biopsy would correctly result in a low-risk classification for the associated patients 40, 42 and thus these patients would be classified as being suitable for treatment by surgical resection alone. Similarly, in each of the regions of the lung tumours 28, 30, a biopsy would correctly result in a high-risk classification for the associated patients 48, 50 and thus these patients would be classified as requiring treatment by surgical resection and adjuvant chemotherapy. However, a third patient 44 has a lung tumour 24 similar to that illustrated in FIG. 1a. As illustrated, the biopsy from region R4 results in a classification as low risk which is not in line with the classification which results from biopsies from other regions within the lung tumour 24. This is significant because the patient is unlikely to receive adjuvant treatment based on this diagnosis and is thus not receiving sufficient treatment. Thus, the patient has sub-optimal treatment and follow-up. Similarly, a fourth patient 46 has a lung tumour 26 which will produce different results depending on where the biopsy is sampled from. In this illustration, the biopsy provides a high risk classification which may result in the patient being subject to unnecessary treatment and thus subject to the side effects of chemotherapy.

FIG. 1c shows the result of analysing a known signature for LUAD described in "Development of a RNA-seq Based Prognostic Signature in Lung Adenocarcinoma" by Shukla et al in JNCL J Natl Cancer Inst 109 (2017). The signature is analysed using information from the TRACERx lung trial which is the world's largest multi-region sequencing study, enabling detailed exploration of tumour evolution. The study is described for example in "Tracking genomic cancer evolution for precision medicine: the lung TRACERx study" by Jamal-Hanjani et al published in PLos Biol 12 (2014). In FIG. 1c, 89 tumour regions from 28 patients within the TRACERx study are analysed and as plotted on the graph, each patient is ordered by predicted survival "riskscore" with the lowest risk patients at the left of the graph. To calculate the "riskscore" in this example, regression coefficients were re-derived from supplementary data provided in the original publication by fitting a linear model without intercept through regression of the calculated riskscore on expression values of the four genes in the signature. Each point on FIG. 1c represents a single tumour region and the vertical lines display the range of the riskscore for each patient. 11 patients are classified as low risk and 5 are classified as high risk regardless of the location of the biopsy. However, there are 12 discordant patients where the riskscore depends on the location of the biopsy.

FIG. 1d presents the data in FIG. 1c as a bar chart with the percentages of low risk, high risk and discordant patients. FIG. 1e is a similar bar chart for a different signature based on immune-related gene pairs which is described in "Development and Validation of an Individualized Immune Prognostic Signature in Early-Stage Nonsquamous Non-Small Cell Lung Cancer" by Li et al published in JAMA Oncol (2017). In both cases, there is a significant proportion of discordant patients—43% or 29%—whereby different regions from the same tumour may be classified as harbouring distinct profiles of molecular risk. The high proportion of patients vulnerable to tumour sampling bias potentially limits the clinical utility of such prognostic assays.

To-date the majority of gene expression based prognostic signatures in LUAD have been defined using microarray expression profiling, rather than RNA-sequencing. FIG. 1f shows the concordance results for nine published LUAD prognostic signatures detailed in the table below. The number of patients n in each paper is indicated. Hierarchical clustering was performed for each prognostic signature using the Ward method on the Manhattan metric as described in "Intratumour Heterogenity Affects Gene Expression Profile Test Prognostic Risk Stratification in Early Breast Cancer" by Gyanchandani et al in Clin Cancer Res 22, 5362-5369 (2016). For a given number of clusters, clustering concordance is quantified as the percentage of patients with all tumour regions in the same cluster. The results are plotted as the percentage of patients with tumour regions clustering together against the number of clusters. Vertical dashed lines mark the range of clusters (2, 3, 14 and 28):

| Reference | Signature described in: | n= |
|---|---|---|
| 100 | Gene-expression profiles predict survival of patients with lung adenocarcinoma by Beer et al - Nat Med 8,816-824, 2002 | 97 |
| 102 | Development and Validation of an Individualized Immune Prognostic Signature in Early-Stage Nonsquamous Non-Small Cell Lung Cancer by Li et al published in JAMA Oncol (2017) | 40 |
| 104 | Diversity of gene expression in adenocarcinoma of the lung by Garber et al in Proc Natl Acad Sci 98, 13874-13879 (2001) | 25 |
| 106 | Survival prediction of stage I lung adenocarcinomas by expression of 10 genes by Bianchi et al in J Clin Invest 117, 3426-3444 (2007) | 10 |
| 108 | A practical molecular assay to predict survival in resected non-squamous, non-small lung cancer: development and international validation studies by Kratz et al published in the Lancet 379, 823-832 (2012) | 11 |
| 110 | A robust prognostic gene expression signature for early stage lung adenocarcinoma by Krystanek et al in Biomark Res 4 (2016) | 6 |
| 112 | Validation of a Proliferation based expression signature as prognostic marker in early stage lunch adenocarcinoma by Wistuba et al published in Clin Cancer Res (2013) | 31 |
| 114 | Development of a RNA-seq Based Prognostic Signature in Lung Adenocarcinoma by Shukla et al in JNCL J Natl Cancer Inst 109 (2017). | 56 |
| 116 | Multi-gene assay is prognostic of survival in patients with early stage lung adenocarcinoma by Raz et al published in Clin Cancer Res 14, 5565-5570 (2008) | 4 |

At 28 clusters, the median clustering discordance rate was 50% (15.5/28 LUAD tumours) indicating that half the tumour regions would be at risk of misclassification due to sampling bias. The range was between 18-82% indicating that some signatures performs significantly better than others. Taken together FIGS. 1a to 1f illustrate that sampling bias can confound the use of molecular biomarkers in several cancer types. As described in "Tracking the evolution of non-small cell lung cancer" by Jamal-Hanjani et al in N Engl J Med 376, 2109-2121 (2017), ITH and chromosomal instability (CIN) are common features of NSCLC and other types of cancer. Furthermore, genetic intra-tumour heterogeneity (ITH) is prevalent across cancer types as described in "The Causes and Consequence of Genetic Heterogeneity in Cancer Evolution" by Burrell et al published in Nature 501, 338-345 (2013).

Background information on previous lung cancer prognostic signatures can be found in International Patent Publication WO201/063121 (describes using a 16-gene prognostic signature to classify non-small cell lung cancer (NSCLC) patients into risk groups); US Patent Publication US2010/184063 (describes using a 15-gene prognostic and predictive signature to classify NSCLC patients into risk groups); and International Patent Publication WO2015/138769 (describes using a 9-gene prognostic signature to classify NSCLC patients into risk groups).

The present applicant has recognised the need for improved gene signatures to assist clinicians to refine prognostic accuracy to help inform therapeutic decision-making, e.g. to choose between surgical resection alone or surgical resection followed by chemotherapy or another adjuvant treatment.

SUMMARY

According to the present invention there is provided an apparatus and method as set forth in the appended claims. Other features of the invention will be apparent from the dependent claims, and the description which follows.

We describe a method for providing a prognosis for a subject with lung cancer, the method comprising: (a) contacting a biological sample from the subject with reagents that specifically bind to each member of a panel of biomarkers comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1; (b) determining a riskscore of the subject based on the nucleic acid levels of expression of the biomarkers in the samples; and (c) providing a prognosis for the lung cancer based on the risk score of the subject.

Determining a risk score of the subject may comprise: for each of the biomarkers, determining a score indicative of nucleic acid levels of expression in the tissue sample; calculating a riskscore based on the determined scores, wherein the riskscore is calculated by summing weighted biomarker scores, wherein the biomarker scores are based on the determined scores and each biomarker score has an associated weight; and comparing the riskscore to a threshold. In this way, each subject may for example be stratified into a high risk group (e.g. a riskscore above the threshold) or a low risk group (e.g. a riskscore equal to or below the threshold). For example, when considering all types of lung cancer, the high risk group may have a low survival outcome and the low risk group may have a good chance of survival. Alternatively, when considering early stage cancers, the high risk group may be more likely to relapse than the low risk group. The associated weight for each of the biomarker scores for GOLGA8A, SCPEP1, SLC46A3 and XBP1 may have a negative value indicating that they are genes which are favourable. The associated weight for the biomarker score for ANLN, ASPM, CDCA4, ERRFI1, FURIN, ITGA6, JAG1, LRP12, MAFF, MRPS17, PLK1, PNP, PPP1R13L, PRKCA, PTTG1, PYGB, RPP25, SNX7 and TPBG may have a positive value.

The weighted sum for the riskscore may be determined from:

$$riskscore = b_1 x_{1i} + b_2 x_{2i} + \ldots + b_n x_{ni}$$

where $x_{1i}, x_{2i}, \ldots, x_{ni}$ are the biomarker scores for the four selected biomarkers for each subject i and $b_1, b_2, \ldots, b_n$ are a set of associated weights for each biomarker score.

The method may further comprise determining the weights for the weighted sum using a Cox proportional hazard model which is trained using training data comprising information on a plurality of biomarkers in a set of subjects. The method may comprise identifying the plurality of biomarkers to be used in the Cox proportional hazard model, wherein the plurality of biomarkers are selected from the group comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1.

The threshold may be the median riskscore for the training data.

Determining a score indicative of a level of the biomarker may comprise determining a scaled intensity score. The biomarker score may be based on the scaled intensity score which has been adjusted by subtracting an adjustment factor. Determining a score indicative of a level of the biomarker may comprise awarding a first value when the level is above a threshold and a second value when the level is below the threshold. Determining a score indicative of a level of the biomarker may comprise awarding a first value when the level is above an upper threshold, a second value when the level is below the upper threshold but above a lower threshold and a third value when the level is below the lower threshold.

The reagents may be nucleic acids.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA, miRNA, lncRNA), naturally occurring, mutated, synthetic DNA or RNA molecules, and analogues of the DNA or RNA generated using nucleotide analogues. Nucleic acids can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene", "allele" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences. Thus, according to the various aspects of the invention, genomic DNA, cDNA or coding DNA may be used. In one embodiment, the nucleic acid is cDNA or coding DNA. Thus, genes may include introns and exons as in genomic sequence, or may comprise only a coding sequence as in cDNAs, and/or may include cDNAs in combination with regulatory sequences.

Analysis of nucleic acids may be carried out using suitable techniques, for example techniques for measuring gene expression, including but not limited to digital PCR, qPCR, microarrays, RNA-Seq or nanostring® assays. In certain embodiments described herein, gene expression is measured by quantifying RNA, including RNA-Seq or nanostring® assays. It will be understood that more than one technique for measuring gene expression may be used.

RNA sequencing (RNA-Seq) is a transcriptome profiling technology that utilizes next-generation sequencing platforms based on next generation sequencing (NGS). RNA-Seq transcripts are reverse-transcribed into cDNA, and adapters are ligated to each end of the cDNA. Sequencing can be done either unidirectional (single-end sequencing) or bidirectional (pared-end sequencing) and then aligned to a reference genome database or assembled to obtain de novo transcripts, proving a genome-wide expression profile. RNA-seq can qualitatively and quantitatively investigate any RNA type including messenger RNAs (mRNAs), microRNAs, small interfering RNAs, and long noncoding RNAs.

RNA can be analysed using the NanoString nCounter gene expression assay. NanoString is a relatively new molecular profiling technology that can generate accurate genomic information from small amounts of fixed patient tissues. The NanoString platform uses digital, colour-coded barcodes or code sets tagged to sequence-specific probes, allowing quantification of mRNA expression (Geiss et al, Nat Biotechnol. 2008 March; 26 (3):317-25, Das et al, NanoString expression profiling identifies candidate biomarkers of RAD001 response in metastatic gastric cancer, ESMO Open 2016, 1-9). The NanoString system hybridizes two probes to each target transcript: a biotin-labeled capture probe and a fluorescent barcode-labeled reporter probe. Reporter probes hybridize with specific RNAs in a sample and capture probes lock them via avidin onto a static surface. The NanoString nCounter Analysis System counts the immobilized RNAs using their barcodes.

The lung cancer may be non-small lung cancer (NSCLC). The NSCLC may be selected from invasive adenocarcinoma (LUAD), squamous cell carcinoma (LUSC), large cell carcinoma, adenosquamous carcinoma, carcinosarcoma, large cell neuroendocrine, undifferentiated non small cell lung cancer or bronchioalveolar. LUAD and LUSC make up the majority of NSCLC cases and the other types tend to be grouped together. The NSCLC may be stage I, stage II, stage III or stage IV.

The sample may be from a surgically resected tumour. The sample may be from lung tissue or a lung tumour biopsy.

The prognosis may provide a risk assessment.

The method may further comprise determining a treatment. Thus, we also describe a method for determining a treatment for a subject the method comprising the method described above and further comprising the further step of determining a treatment. Said treatment may be selected from surgical treatment, chemotherapy, surgery, radiotherapy, immunotherapy or CAR-T therapy. Such treatments are known in the art. It will be appreciated that there are various types of immunotherapies such as immune checkpoint inhibitors, oncolytic virus therapy, T cell therapy and cancer vaccines. The appropriate therapy may be selected.

We also describe a composition comprising a panel of reagents that specifically bind to each member of a panel of biomarkers comprising or consisting of ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1.

We also describe a kit comprising reagents that specifically bind to each member of a panel of biomarkers comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1.

The reagents may be nucleic acids in the composition or kit described above. We also describe use of a composition or a kit in a method for providing a prognosis for a subject with lung cancer as described above. We also describe use of a composition or a kit in a method for providing a treatment for a subject with lung cancer as described above.

We also describe use of ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1 in a method for providing a prognosis for a subject with lung cancer as described above. We also describe use of ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1 in a method for providing a treatment for a subject with lung cancer as described above.

We also describe a method of treatment of a subject with lung cancer comprising the steps of predicting a level of risk of mortality for a subject with lung cancer the method comprising (a) contacting a biological sample from the subject with reagents that specifically bind to each member of a panel of biomarkers comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1; (b) determining a riskscore of the subject based on the nucleic acid levels of expression of the biomarkers in the samples; (c) comparing the riskscore to a threshold to predict whether the subject is high risk of mortality; (d) selecting a treatment; and (e) administering the treatment.

We also describe a method for generating a biomarker signature for a subject with cancer, the method comprising: generating training data from a plurality of subjects who have had cancer, the training data comprising gene expression data for a plurality of genes for each of the plurality of subjects; calculating both an intra-tumour heterogeneity measure and an inter-tumour heterogeneity measure for each gene in the plurality of genes based on the gene expression data; and applying an heterogeneity filter to select genes having both an intra-tumour heterogeneity below an intra-tumour heterogeneity threshold and an inter-tumour heterogeneity above an inter-tumour heterogeneity threshold; wherein the biomarker signature comprises at least some of the selected genes. Such a method may be applicable to a variety of different cancers, especially those associated with ITH.

The method may further comprise: calculating a concordance score for each gene; and applying a concordance filter to select genes having a concordance score below a concordance threshold. The concordance filter may be considered to be a type of heterogeneity filter that removes noisy genes. The concordance score may be calculated for the selected genes after applying the heterogeneity filter. Alternatively, the concordance filter may be applied before calculating both the intra-tumour heterogeneity measure and the inter-tumour heterogeneity measure.

The intra-tumour heterogeneity measure for each gene may be calculated by: obtaining values for the gene expression of each gene at multiple locations within the same tumour, calculating, for each tumour, a measure which is indicative of the obtained gene expression values of each gene, and obtaining the intra-tumour heterogeneity measure as the average value of the indicative measure for each gene in each tumour. The measure which is indicative of the gene expression values may be selected from the standard deviation, the median absolution deviation and the coefficient of variation.

The inter-tumour heterogeneity measure may be calculated by: obtaining values for the gene expression of each gene for each subject at one of multiple regions in a tumour; and taking the standard deviation across the obtained values. The method may further comprise iterating the obtaining and taking steps multiple times and averaging the standard deviation across iterations to obtain the inter-tumour heterogeneity measure. It will be appreciated that other measures than standard deviation may also be used, for example coefficient of variation and median absolute deviation.

The biomarker signature may be prognostic. The method may further comprise: generating training data comprising associated survival data for each of the plurality of subjects; calculating a prognostic measure for each of the plurality of genes based on the survival data; and applying a prognostic filter to select genes having a prognostic measure above a prognostic threshold. The prognostic measure may be calculated using Cox univariate regression analysis.

The biomarker signature may be predictive for a response of a subject to a particular treatment, e.g. immunotherapy. The method may further comprise: generating training data comprising associated response data (e.g. outcome from the particular treatment) for each of the plurality of subjects; calculating a predictive measure for each of the plurality of genes based on the response data; and applying a predictive filter to select genes having a predictive measure above a predictive threshold. The predictive measure may be calculated using regression analysis, correlating gene expression with response to treatment, or proxy measures of treatment response. Such a method may be used to create a predictive signature of treatment response, to help stratify patients for the most appropriate treatment regime. There is thus the potential for a biomarker signature generated as described above to differentiate between cancer subtypes and determining treatment strategy on the basis of the cancer subtype. It will be appreciated that the method of providing a prognosis, the method for determining a treatment for a subject, the composition, the kit, the method of treatment and the uses described above can be applied to any signature which is generated as described above.

We also describe a method for providing a prognosis for a subject with cancer, the method comprising: contacting a biological sample from the subject with reagents that specifically bind to each member of a panel of biomarkers in the signature generated as described above; determining a riskscore of the subject based on the nucleic acid levels of expression of the biomarkers in the samples; and providing a prognosis for the cancer based on the risk score of the subject. We also describe a method for determining a treatment for a subject, the method comprising the method of providing a prognosis and further comprising the further step of determining a treatment. We also describe a composition comprising a panel of reagents that specifically bind to each member of a panel of biomarkers in the signature generated as described above. We also describe a kit comprising reagents that specifically bind to each member of a panel of biomarkers in the signature generated as described above.

We also describe use of the biomarkers in the signature generated as described above in a method for providing a prognosis for a subject with cancer. We also describe use of the biomarkers in the signature generated as described above in a method for providing a treatment for a subject with cancer. We also describe a method of treatment of a subject with cancer comprising the steps of predicting a level of risk of mortality for a subject with cancer the method comprising contacting a biological sample from the subject with reagents that specifically bind to each member of a panel of biomarkers in the signature generated as described above; determining a riskscore of the subject based on the nucleic acid levels of expression of the biomarkers in the samples; comparing the riskscore to a threshold to predict whether the subject is high risk of mortality; selecting a treatment; and administering the treatment.

There may also be a computer device comprising at least one processor; and instructions that, when executed by the at least one processor cause the computer device to perform any of the determining, calculating and comparing steps of the methods described above. There may also be a tangible non-transient computer-readable storage medium having recorded thereon instructions which, when implemented by a computer device, cause the computer device to be arranged as described above and/or which cause the computer device to perform any of the relevant steps of the methods as described above. There may also be a kit comprising the computer device and a microarray for the tissue sample and/or one or more reagents to determine the presence of the biomarkers.

Thus far, we have described using a panel of biomarkers comprising or consisting of 23 specific biomarkers. We now describe embodiments using a panel of biomarkers comprising two or more biomarkers selected from the 23 specific biomarkers.

We also describe a method for providing a prognosis for a subject with lung cancer, the method comprising: (a) contacting a biological sample from the subject with reagents that specifically bind to each member of a panel of biomarkers, the panel comprising at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1; (b) determining a riskscore of the subject based on the nucleic acid levels of expression of the biomarkers in the samples; and (c) providing a prognosis for the lung cancer based on the risk score of the subject.

Determining a risk score of the subject may comprise: for each of the selected biomarkers, determining a score indicative of nucleic acid levels of expression in the tissue sample; calculating a riskscore based on the determined scores, wherein the riskscore is calculated by summing weighted biomarker scores, wherein the biomarker scores are based on the determined scores and each biomarker score has an associated weight; and comparing the riskscore to a threshold. In this way, each subject may for example be stratified into a high risk group (e.g. a riskscore above the threshold) or a low risk group (e.g. a riskscore equal to or below the threshold). For example, when considering all types of lung cancer, the high risk group may have a low survival outcome and the low risk group may have a good chance of survival. Alternatively, when considering early stage cancers, the high risk group may be more likely to relapse than the low risk group. The associated weight for each of the biomarker scores for GOLGA8A, SCPEP1, SLC46A3 and XBP1 may have a negative value indicating that they are genes which are favourable. The associated weight for the biomarker score for ANLN, ASPM, CDCA4, ERRFI1, FURIN, ITGA6, JAG1, LRP12, MAFF, MRPS17, PLK1, PNP, PPP1R13L, PRKCA, PTTG1, PYGB, RPP25, SNX7 and TPBG may have a positive value.

The weighted sum for the riskscore may be determined from:

$$riskscore = b_1 x_{1i} + b_2 x_{2i} + \ldots + b_n x_{ni}$$

where $x_{1i}, x_{2i}, \ldots, x_{ni}$ are the biomarker scores for the four selected biomarkers for each subject i and $b_1, b_2, \ldots, b_n$ are a set of associated weights for each biomarker score.

The method may further comprise determining the weights for the weighted sum using a Cox proportional hazard model which is trained using training data comprising information on a plurality of biomarkers in a set of subjects. The method may comprise identifying the plurality of biomarkers to be used in the Cox proportional hazard model, wherein the plurality of biomarkers are selected from the group comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1.

The threshold may be the median riskscore for the training data.

Determining a score indicative of a level of the biomarker may comprise determining a scaled intensity score. The biomarker score may be based on the scaled intensity score which has been adjusted by subtracting an adjustment factor. Determining a score indicative of a level of the biomarker may comprise awarding a first value when the level is above a threshold and a second value when the level is below the threshold. Determining a score indicative of a level of the biomarker may comprise awarding a first value when the level is above an upper threshold, a second value when the level is below the upper threshold but above a lower threshold and a third value when the level is below the lower threshold.

The reagents may be nucleic acids.

The lung cancer may be non-small lung cancer (NSCLC). The NSCLC may be selected from invasive adenocarcinoma (LUAD), squamous cell carcinoma (LUSC), large cell carcinoma, adenosquamous carcinoma, carcinosarcoma, large cell neuroendocrine, undifferentiated non small cell lung cancer or bronchioalveolar. LUAD and LUSC make up the majority of NSCLC cases and the other types tend to be grouped together. The NSCLC may be stage I, stage II, stage III or stage IV.

The sample may be from a surgically resected tumour. The sample may be from lung tissue or a lung tumour biopsy.

The prognosis may provide a risk assessment.

The method may further comprise determining a treatment. Thus, we also describe a method for determining a treatment for a subject the method comprising the method described above and further comprising the further step of determining a treatment. Said treatment may be selected from surgical treatment, chemotherapy, surgery, radiotherapy, immunotherapy or CAR-T therapy. Such treatments are known in the art. It will be appreciated that there are various types of immunotherapies such as immune checkpoint inhibitors, oncolytic virus therapy, T cell therapy and cancer vaccines. The appropriate therapy may be selected.

We also describe a composition comprising a panel of reagents that specifically bind to each member of a panel of biomarkers comprising or consisting of at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1.

We also describe a kit comprising reagents that specifically bind to each member of a panel of biomarkers comprising at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1. The reagents may be nucleic acids in the composition or kit described above. We also describe use of a composition or a kit in a method for providing a prognosis for a subject with lung cancer as described above. We also describe use of a composition or a kit in a method for providing a treatment for a subject with lung cancer as described above.

We also describe use of at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1 in a method for providing a prognosis for a subject with lung cancer. We also describe use of at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG and XBP1 in a method for providing a treatment for a subject with lung cancer as described above.

We also describe a method of treatment of a subject with lung cancer comprising the steps of predicting a level of risk of mortality for a subject with lung cancer the method comprising: (a) contacting a biological sample from the subject with reagents that specifically bind to each member of a panel of biomarkers, the panel comprising at least two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1; (b) determining a riskscore of the subject based on the nucleic acid levels of expression of the biomarkers in the samples; (c) comparing the riskscore to a threshold to predict whether the subject is high risk of mortality; (d) selecting a treatment; and (e) administering the treatment.

In each of the embodiments of the invention where the panel of biomarkers comprises a selection of biomarkers, the skilled person will understand that the panel of biomarkers may comprise or consist of at least three biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least four biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least five biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least six biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least seven biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least eight biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least nine biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least ten biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least eleven biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least twelve biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least thirteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least fourteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least fifteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least sixteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least seventeen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least eighteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least nineteen biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least twenty biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least twenty-one biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of at least twenty-two biomarkers selected from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1.

In each of the embodiments of the invention where the panel of biomarkers comprises a selection of biomarkers, the skilled person will understand that the panel of biomarkers may comprise or consist of ANLN and at least one of ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of ASPM and at least one of ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of CDCA4 and at least one of ASPM, ANLN, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of ERRFI1 and at least one of ASPM, ANLN, CDCA4, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of FURIN and at least one of ASPM, ANLN, CDCA4, ERRFI1, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of GOLGA8A and at least one of ASPM, ANLN, CDCA4, ERRFI1, FURIN, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of ITGA6 and at least one of ASPM, ANLN, CDCA4, ERRFI1, FURIN, GOLGA8A, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of JAG1 and at least one of ASPM, ANLN, CDCA4, ERRFI1, FURIN, GOLGA8A, ITGA6, LRP12, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of LRP12 and at least one of ASPM, ANLN, CDCA4, ERRFI1, FURIN, GOLGA8A, ITGA6, JAG1, MAFF, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of MAFF and at least one of ASPM, ANLN, CDCA4, ERRFI1, FURIN, GOLGA8A, ITGA6, JAG1, LRP12, MRPS17, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of MRPS17 and at least one of ASPM, ANLN, CDCA4, ERRFI1, FURIN, GOLGA8A, ITGA6, JAG1, LRP12, MAFF, PLK1, PNP, PPP1R13L, PRKCA, PTTG1, PYGB, RPP25, SCPEP1, SLC46A3, SNX7, TPBG, XBP1. It will be understood that the panel of biomarkers may comprise or consist of PLK1 and at least one of ASPM, ANLN, CDCA4, ERRFI1, FURIN, GOLGA8A, ITGA6, JAG1, LRP12, MAFF, MRPS17, PNP, PPP1R13L, PRKCA, PTTG1, PYGB, RPP25, SCPEP1, SLC46A3, SNX7, TPBG, XBP1. It will be understood that the panel of biomarkers may comprise or consist of PNP and at least one of ASPM, ANLN, CDCA4, ERRFI1, FURIN, GOLGA8A, ITGA6, JAG1, LRP12, MAFF, MRPS17, PLK1, PPP1R13L, PRKCA, PTTG1, PYGB, RPP25, SCPEP1, SLC46A3, SNX7, TPBG, XBP1. It will be understood that the panel of biomarkers may comprise or consist of PPP1R13L and at least one of ASPM, ANLN, CDCA4, ERRFI1, FURIN, GOLGA8A, ITGA6, JAG1, LRP12, MAFF, MRPS17, PLK1, PNP, PRKCA, PTTG1, PYGB, RPP25, SCPEP1, SLC46A3, SNX7, TPBG, XBP1. It will be understood that the panel of biomarkers may comprise or consist of PRKCA and at least one of ASPM, ANLN, CDCA4, ERRFI1, FURIN, GOLGA8A, ITGA6, JAG1, LRP12, MAFF, MRPS17, PLK1, PNP, PPP1R13L, PTTG1, PYGB, RPP25, SCPEP1, SLC46A3, SNX7, TPBG, XBP1. It will be understood that the panel of biomarkers may comprise or consist of PTTG1 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PYGB, RPP25, SCPEP1, SLC46A3, SNX7, TPBG, XBP1. It will be understood that the panel of biomarkers may comprise or consist of PYGB and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, RPP25, SCPEP1, SLC46A3, SNX7, TPBG, XBP1. It will be understood that the panel of biomarkers may comprise or consist of RPP25 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, SCPEP1, SLC46A3, SNX7, TPBG, XBP1. It will be understood that the panel of biomarkers may comprise or consist of SCPEP1 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SLC46A3, SNX7, TPBG, XBP1. It will be understood that the panel of biomarkers may comprise or consist of SLC46A3 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SNX7, TPBG, XBP1. It will be understood that the panel of biomarkers may comprise or consist of SNX7 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, TPBG, XBP1. It will be understood that the panel of biomarkers may comprise or consist of TPBG and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, XBP1. It will be understood that the panel of biomarkers may comprise or consist of XBP1 and at least one of ASPM, ANLN, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG.

The skilled person would understand that any combination of two or more biomarkers from ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1 may be sufficient to provide a prognosis for a subject with lung cancer or to determine a treatment.

Although a few preferred embodiments of the present invention have been shown and described, it will be appreciated by those skilled in the art that various changes and modifications might be made without departing from the scope of the invention, as defined in the appended claims.

BRIEF DESCRIPTION OF DRAWINGS

For a better understanding of the invention, and to show how embodiments of the same may be carried into effect, reference will now be made, by way of example only, to the accompanying diagrammatic drawings in which:

FIG. 1b is a schematic illustration of the steps of a prediction method and the clinical implications of the tumour sampling bias problem of FIG. 1a;

DESCRIPTION OF DRAWINGS

As explained above, FIGS. 1a to 1f illustrate that sampling bias can confound the use of molecular biomarkers in several cancer types. This is because intratumour heterogeneity (i.e. spatial variation in genetic and transcriptomic features within an individual tumour), as substrate for tumour evolution, impacts the outcome of the application of the molecular biomarkers because the result may depend on the location of the tumour sample which is being tested. Multiple solutions to the tumour sampling bias problem have been proposed, including leveraging multi-region sequencing to (i) pool multiple biopsies in order to gain a global molecular risk estimate for an individual tumour (as described in "Stability and Heterogeneity of Expression Profiles in Lung Cancer Specimens Harvested Following Surgical Resection" by Blackhall at al published in Neoplasia (2004)); or (ii) to identify the "lethal" subclone with maximal immune evasive (e.g. as described in "Comprehensive Intrametastatic Immune Quantification and Major Impact of Immunoscore on Survival" by Mlecnik et al published in JNCL J Natl Cancer Inst 110, 97-108 (2018)) or metastatic potential (e.g. as described in "Distant metastasis occurs late during the genetic evolution of pancreatic cancer" by Yachida et al published in Nature 467, 1114-1117 (2010)). However, in the clinical setting multi-region sequencing is currently impractical.

Figure 1A:
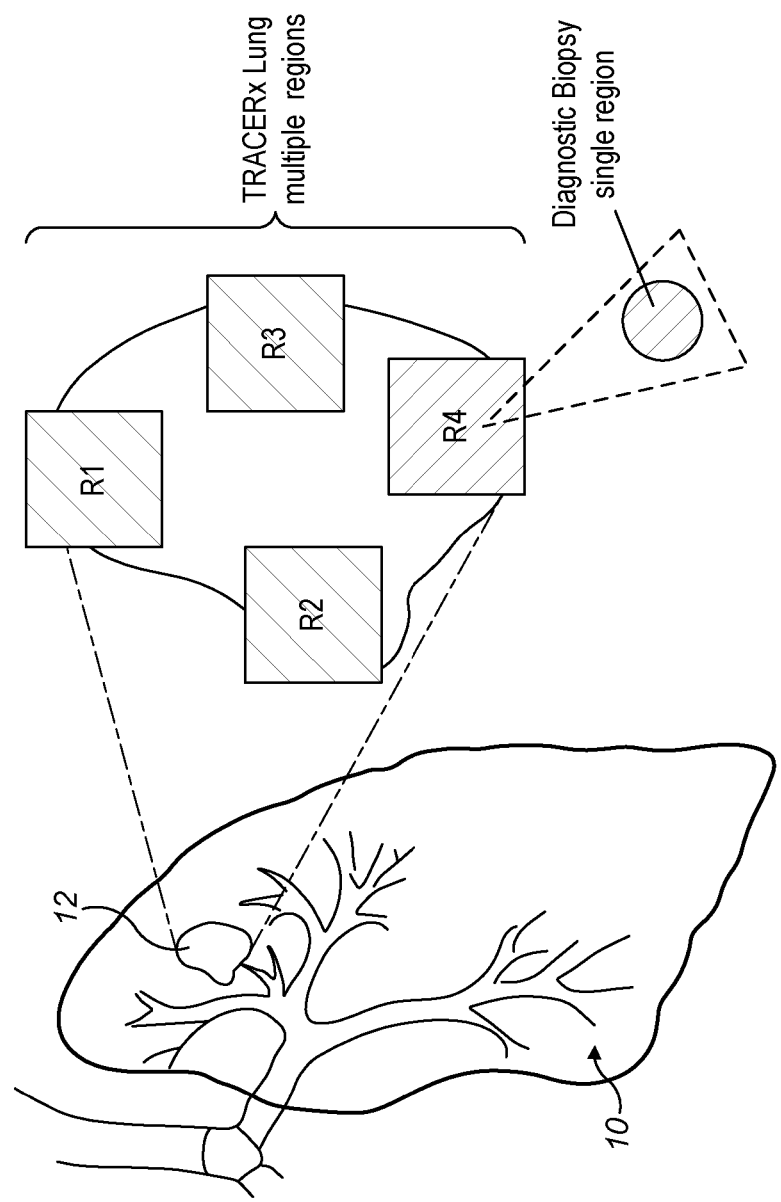
FIG. 1a is a schematic illustration of a lung tumour showing sampling sites which illustrate the tumour sampling bias problem.
Figure 1B:
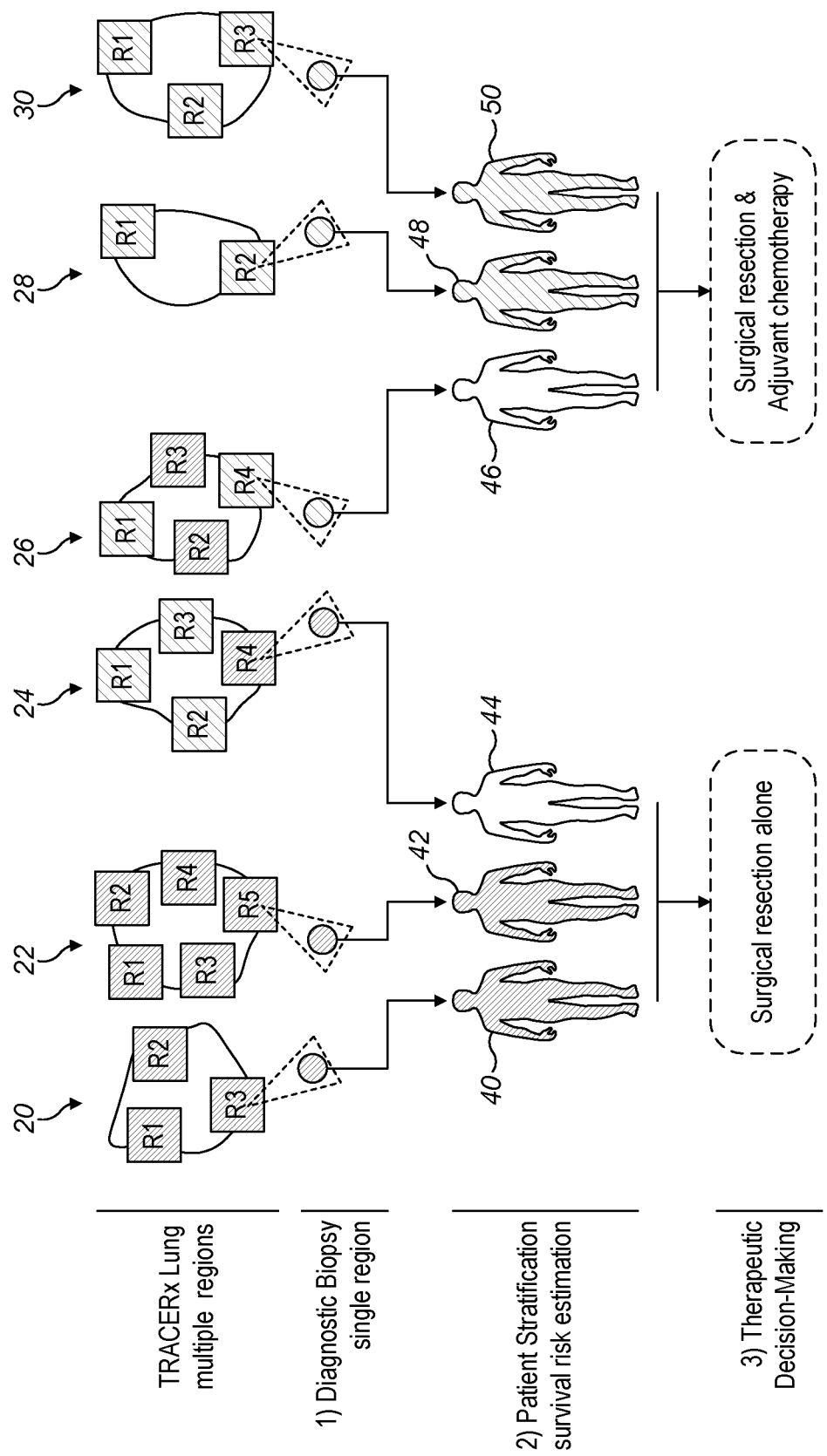
Figure 1C:
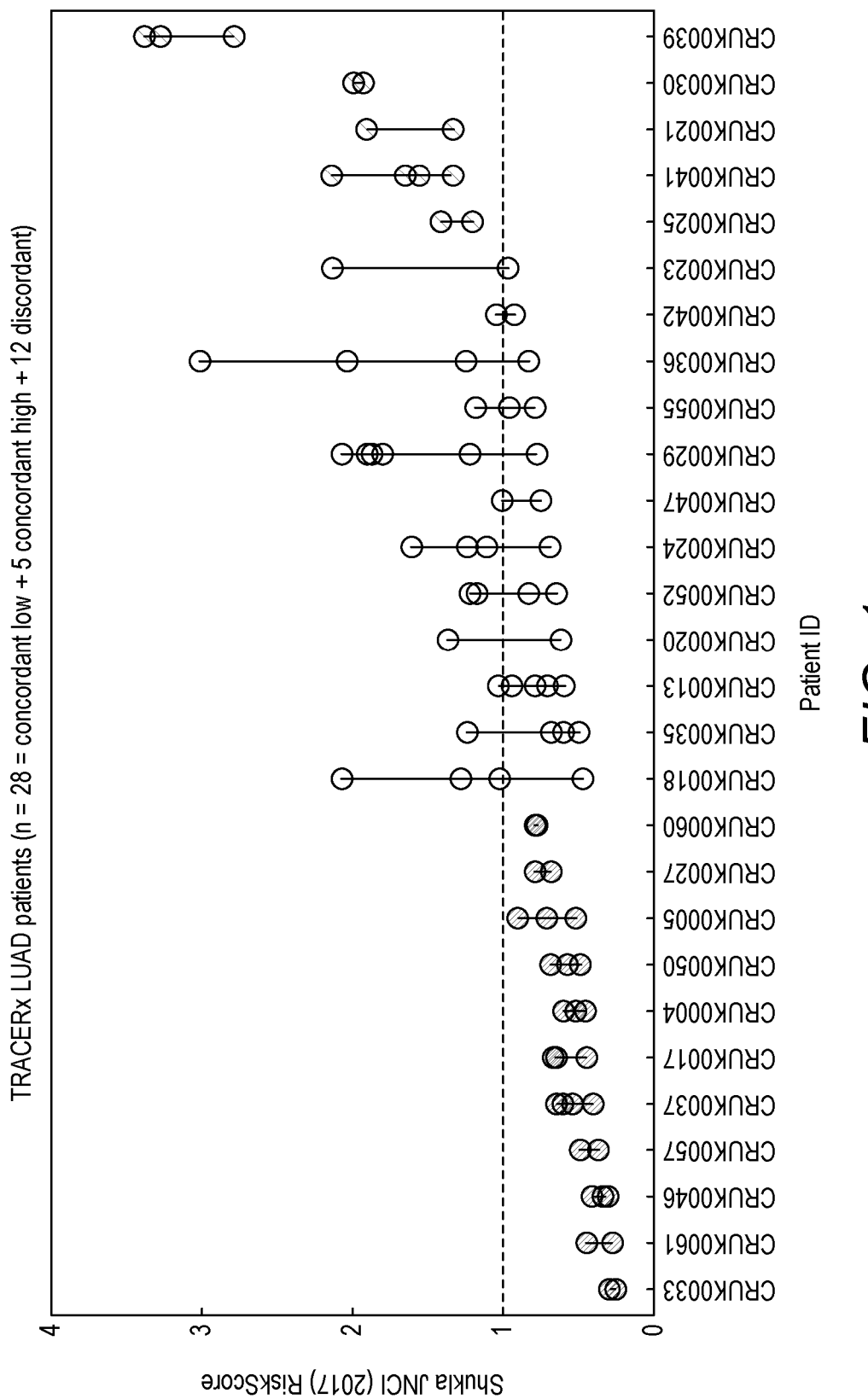
FIG. 1c plots the riskscore against patient using a particular known signature.
Figure 1D:
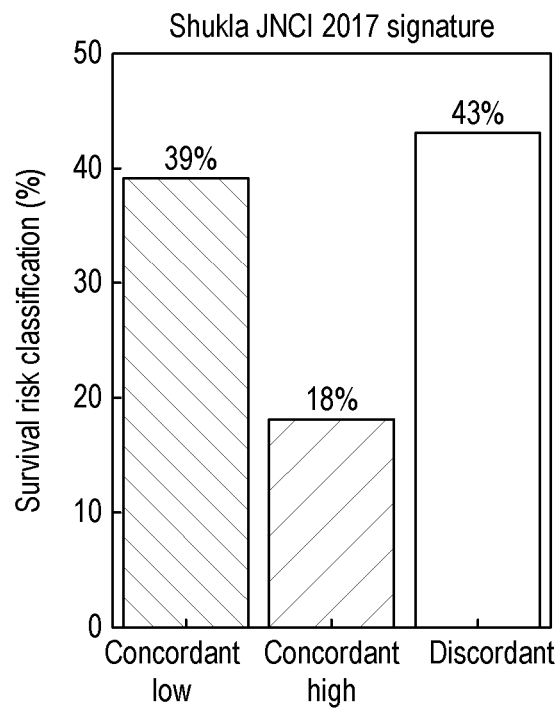
FIGS. 1d and 1e are bar charts showing the proportions of low, high and discordant risk patients using two known signatures.
Figure 1E:
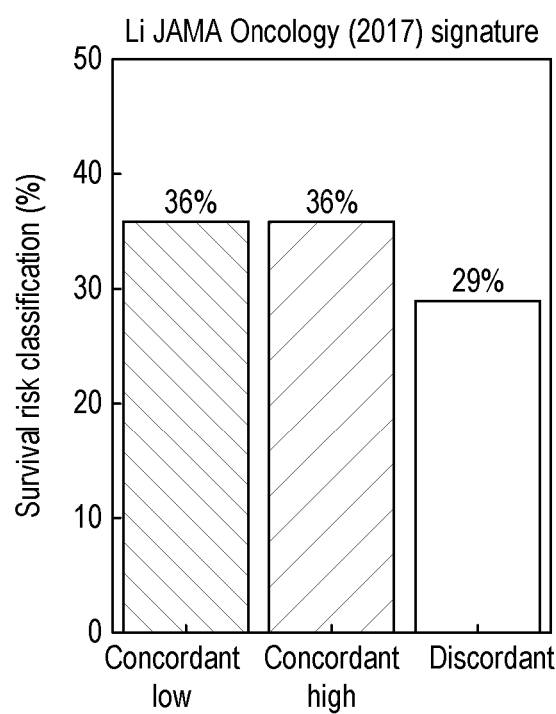
Figure 1F:
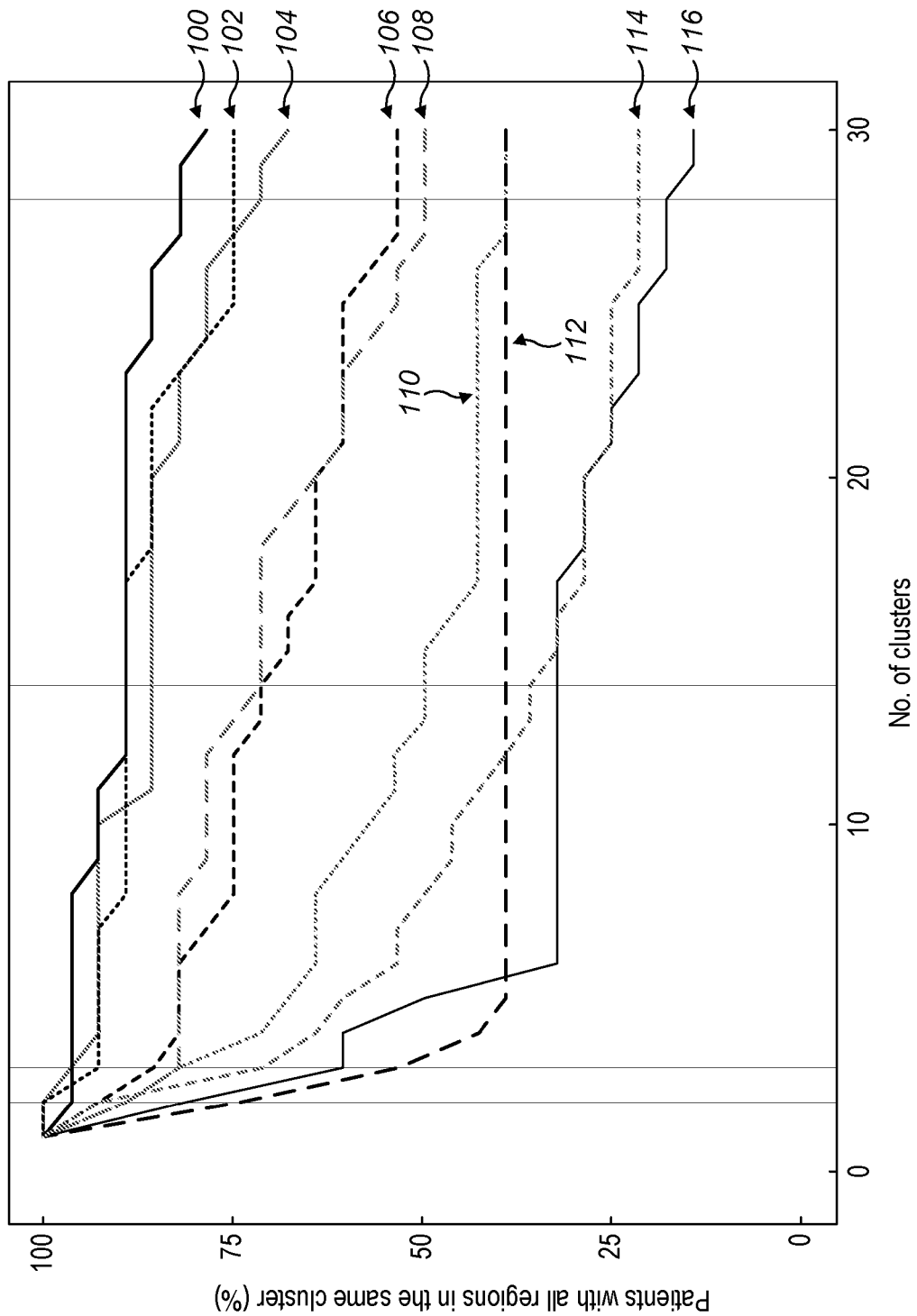
FIG. 1f plots percentage of patients with tumour regions clustering together against the number of clusters for 9 known signatures.
Figure 2A:
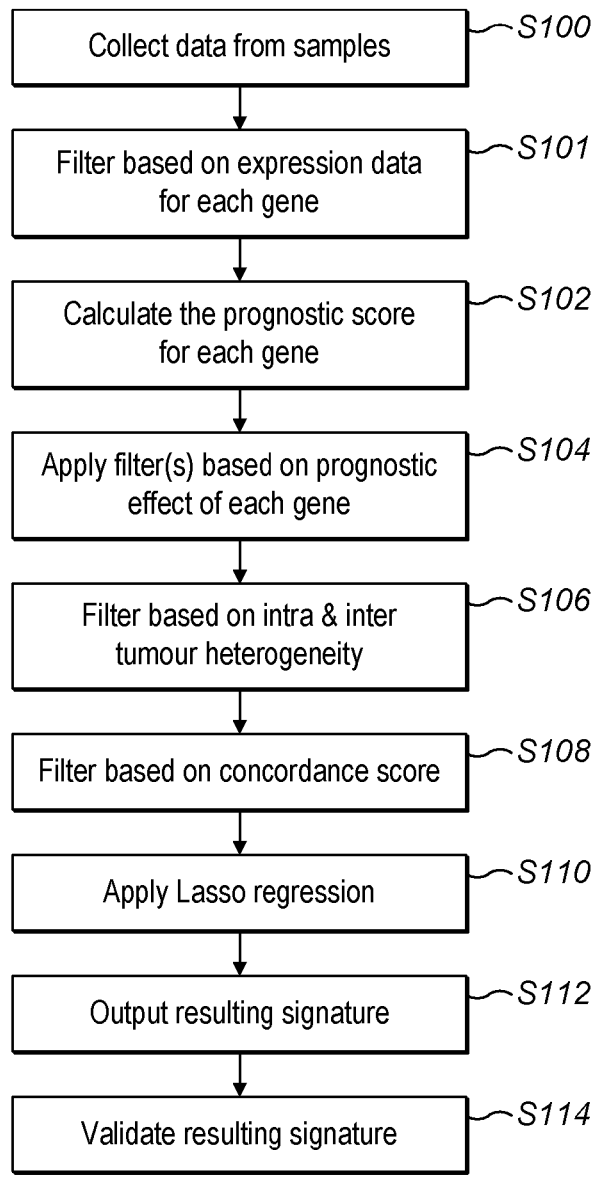
FIG. 2a is a flowchart showing the steps of the method for developing and validating a prognostic signature.

FIG. 2a is a flowchart of the steps in developing a set of biomarkers (or gene-expression signature) which produces a reliable prognostic result that is applicable to single region tumour samples which are routinely collected in clinical practice. As explained in more detail below, the set of biomarkers comprises genes with low intra-tumour heterogeneity but high inter-tumour heterogeneity which minimises the confounding effects of sampling bias but maximises discriminatory power between patients.

The first step S100 is to collect training data, for example gene expression and survival data from the Cancer Genome Atlas (TCGA) for 959 NSCLC patients who are at stages I to III (469 LUAD patients and 490 LUSC patients). This data forms a training dataset which is used to derive the signature as described below. The downloaded data may thus be processed as per standard techniques in an RNA-seq pre-processing pipeline to form the training data. For example, alignment to the human genome may be performed, e.g. using the MapSplice package described in 67. Gene expression may then be quantified, e.g. using the GenomicFeatures and Genomic Ranges packages from Bioconductor. An expression filter may then be applied keeping genes with at least 0.5 CPM in at least 2 tumour samples, as shown in step S101. Normalised count values are then obtained for filtered genes using a variance stabilizing transformation from the DESeq2 package described in "Moderated estimation of fold change and dispersion for RNA-seq data with DESeq2" by Love at al published in Genome Biol 15, 550 (2014). It will be appreciated that data for different patients could also be collected when developing a prognostic signature for a different disease.

The next step S102 is to calculate a prognostic measure for each gene which identifies significantly prognostic genes. A first filtering step S104 is then applied to remove genes based on their prognostic effect (i.e. to select the genes having a prognostic measure above a threshold). Each of these genes has an unknown impact on the overall survival for each patient. The prognostic measure may be calculated using any suitable technique.

For example, Cox univariate regression analysis may be applied. The Cox model is expressed by the hazard function denoted by h(t), is used. The hazard function can be interpreted as the risk of dying at time t. It can be estimated as follows:

$$h(t) = h_0(t) \times \exp(b_1 x_1 + b_2 x_2 + \ldots + b_p x_n)$$

where t represents the survival time, h(t) is the hazard function determined by a set of n covariates ($x_1, x_2, \ldots, x_n$)—in this cases the genes, the set ($b_1, b_2, \ldots, b_n$) are weights (or coefficients) for each covariate and the term $h_0$ is called the baseline hazard which corresponds to the value of the hazard if all the $x_i$ are equal to zero (the quantity exp(0) equals 1). The 't' in h(t) reminds us that the hazard may vary over time. However, the time variance can be removed so that the model can be rewritten in linear form by taking the log of the hazard ratio for patient i to the reference group and this may be written as:

$$\log \frac{h(t; x_i)}{h_0(t)} = b_1 x_{1i} + b_2 x_{2i} + \ldots + b_n x_{ni}$$

This linear equation is known as the Cox Proportional Hazards model with a set of n covariates (i.e. genes) ($x_{1i}, x_{2i}, \ldots, x_{ni}$) for each patient i and a set ($b_1, b_2, \ldots, b_n$) of weights which optimise the model for all patients. A univariate analysis means considering each variable in term. Typically for each variable, the coefficient is calculated together with the lower and upper limits for the 95% confidence interval around the coefficient (CI95L and CI95U respectively). The P-value is a measure of the statistical significance of the variable and is calculated either using the Wald-test or the Log-rank test. The Q-value is an adjusted P-value using the Benjamini & Hochberg method.

As shown in step S104, one than one prognostic filter may be applied. For example, a first filter may comprise filtering all genes based on a prognostic significance threshold, e.g. with P<0.05 which in this example may reduce the number of genes from 19026 to 4240. A second filter may be applied to filter genes based on a median threshold, e.g. to filter out all genes which have a value for the prognostic measure which is below a prognostic threshold may be removed. In this example, this may reduce the number of genes from 19026 to 9512. The two thresholds together may be considered a prognostic threshold and thus overall the first filtering step may reduce the number of genes from 19026 to 2023.

A second filtering step S106 may then be applied. This filter may be termed a clonal expression filter or heterogeneity filter. As explained in more detail below, the clonal expression filter may remove the genes which do not have both low intra-tumour heterogeneity and high inter-tumour heterogeneity (i.e. select the genes which have both low intra-tumour heterogeneity and high inter-tumour heterogeneity). In this example, this may reduce the number of genes from 2023 to 176.

A third filtering step S108 may then be applied. This filter which may be termed a concordance filter may short-list the remaining genes based on gene-wise clustering concordance scores. The clustering concordance score may be calculated using any suitable technique. For example, concordance may be determined through hierarchical clustering analysis on cancer expression data where multiple samples have been obtained from each tumour, e.g. using the Ward method on the Manhattan metric as described in "Intratumor Heterogeneity Affects Gene Expression Profile Test Prognostic Risk Stratification in Early Breast Cancer" by Gyanchandani et al published in *Clin. Cancer Res.* 22, 5362-5369 (2016). Concordance is determined on a per gene level as the percent of tumours where all samples cluster together. The clustering analysis may be run iteratively from 2 to the total number of patients (e.g. 28 in this TRACERx LUAD cohort). For each gene, a curve may be plotted for the number of patients will al regions in the same cluster against the number of clusters. For example, as shown in FIGS. 2d and 2e, the proportion of patients with all samples in the same cluster has been plotted against the number of clusters (2 to 28) for two genes CKMT2 and HOXC11. The clustering concordance score for each gene is then summarised as the area under the curve. The concordance scores for each gene may be plotted as shown in FIG. 2f which shows the hierarchical clustering concordance for each gene. Once the concordance scores for each gene have been calculated, all genes having a concordance score below a concordance threshold may be removed. The concordance threshold (i.e. cut-off) may be determined using ten-fold cross-validation. In this example, this may reduce the number of genes from 176 to 90.

The number of genes may still be too high for a practical prognostic kit and thus the number of genes may be optionally further reduced using standard techniques such as Lasso regression (S110). Lasso regression may be applied in the R software environment using the glmnet package described in "Regularised Paths for Generalized Linear Models via Coordinate Descent" by Friedman et al published in J Stat Softw 33, 1 to 22 (2010) for a Cox's Proportional Hazard Model (e.g. as described in "Regularisation Paths for Cox's Proportional Hazards Model via Coordinate Descent" by Simon et al published in J Stat Softw 39, 1-13 (2011)) applying the lasso penalty (alpha=1). In this example, this may reduce the number of genes from 90 to 23. The resulting set of 23 genes (i.e. signature) is then output (S112). The resulting signature may be termed an ORACLE signature (Outcome Risk Associated Clonal Lung Expression). The prognostic accuracy of the output signature may be evaluated using validation data (S114).

It will be appreciated that each of the filtering steps in FIG. 2a may be applied in any order. The order shown is merely exemplary and not intended to be limiting.

The prognostic biomarker signature comprises the following genes: ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1. There are five genes related to cell proliferation: ANLN, ASPM, CDCA4, PLK1, PRKCA) and six genes relating to oncogenic signalling pathways (ERRFI, FURIN, ITGA6, JAG1, PPP1R13L, PTTG1). Only seven of the genes appear to have been previously used in LUAD prognostic signatures, namely ASPM, FURIN, PLK1, PNP, PRKCA, PTTG1 and TTBG. Prognostic biomarkers predict survival risk independent of therapy.

A method for providing a prognosis or predicting a level of risk for a subject with lung cancer, the method comprising:
  a) contacting a biological sample from the subject with reagents that specifically bind to each member of a panel of biomarkers comprising or consisting of ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, XBP1; b) determining a riskscore of the subject based on the nucleic acid levels of expression of the biomarkers in the samples; and
  c) providing a prognosis for the lung cancer based on the risk score of the subject.

The method may also comprise obtaining the sample from the patient. The sample may be a tumour sample. The reagent used in the methods, kits and compositions provided herein may be a nucleic acid, for example an oligonucleotide or primer.

Prognosis as used herein relates to a clinical outcome, such as overall survival, medium or long term mortality (e.g. 1, 2, 3, 4 or 5 years) or disease free survival.

It will be appreciated that FIG. 2a shows a method for generating a signature which is prognostic, but the method may be readily adapted for prediction by replacing the prognostic measures with predictive measures.

Figure 2B:
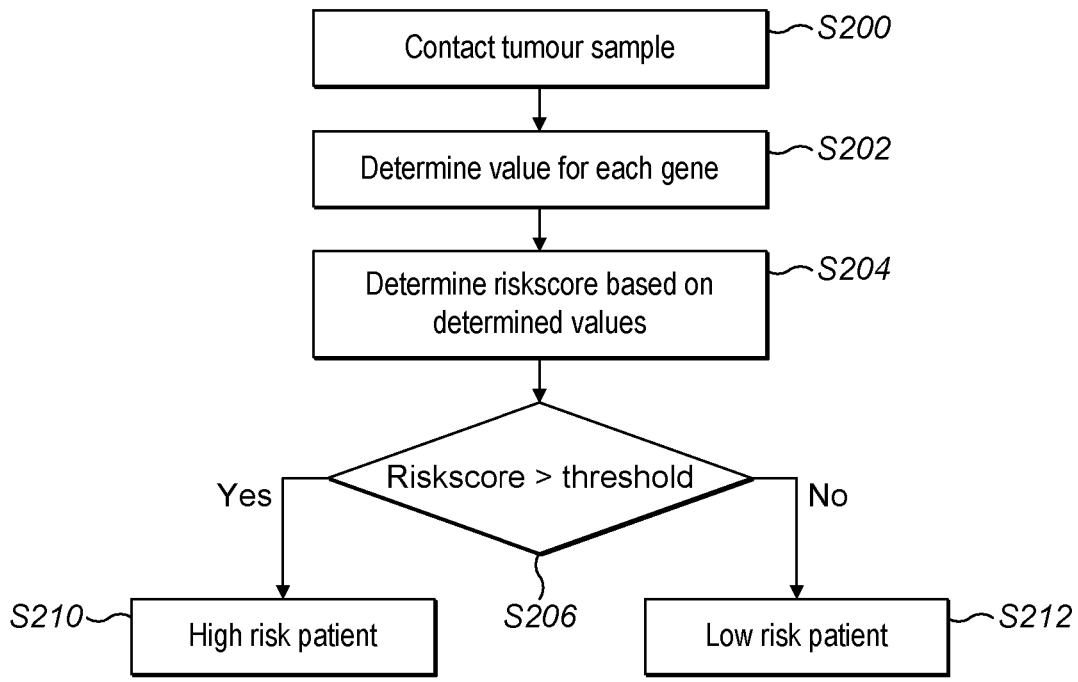
FIG. 2b is a flowchart showing the steps of the prognostic method.

FIG. 2b provides an embodiment of the method for prognosis. It shows the steps which may be carried out in a prognosis method using the output signature. The first step is contacting a biological sample (step S200). The biological sample may be a tumour sample may be obtained using any appropriate method, e.g. from a donor sample obtained using a biopsy. A value for each of the 23 genes within the tumour sample is then determined (step S202) using standard techniques.

The next step (S204) is to determine the risk score from a weighted sum of the values for each of the 23 genes. The riskscore may thus be calculated from:

$$\text{riskscore} = b_1 x_{1i} + b_2 x_{2i} + \ldots + b_n x_{ni}$$

where $x_{1i}, x_{2i}, \ldots, x_{ni}$ are the values for the 23 selected genes for each patient i and $b_1, b_2, \ldots, b_n$ are a set of associated weights for each gene. The weights may be determined using Lasso regression as described above.

As an example, suitable weights are shown below for each of the genes in the signature. Genes with a positive beta coefficient are associated with a hazard ratio>1 (i.e. are "unfavourable genes", predicting worse survival) and vice versa for genes with negative coefficients ("favourable genes"). It will be appreciated that these weights are indicative of suitable values and not limiting.

| Gene | Description | beta |
|---|---|---|
| ANLN | Anillin Actin Binding Protein | 0.058692 |
| ASPM | Abnormal Spindle Microtubule Assembly | 0.003462 |
| CDCA4 | Cell Division Cycle Associated 4 | 0.04194 |
| ERRFI1 | ERBB Receptor Feedback Inhibitor 1 | 0.013238 |
| FURIN | Furin, Paired Basic Amino Acid Cleaving Enzyme | 0.208437 |
| GOLGA8A | Golgin A8 Family Member A | −0.02849 |
| ITGA6 | Integrin Subunit Alpha 6 | 0.058465 |
| JAG1 | Jagged 1 | 0.012599 |
| LRP12 | LDL Receptor Related Protein 12 | 0.03841 |
| MAFF | MAF BZIP Transcription Factor F | 0.075071 |
| MRPS17 | Mitochondrial Ribosomal Protein S17 | 0.146466 |
| PLK1 | Polo Like Kinase 1 | 0.029842 |
| PNP | Purine Nucleoside Phosphorylase | 0.011775 |
| PPP1R13L | Protein Phosphatase 1 Regulatory Subunit 13 Like | 0.062383 |
| PRKCA | Protein Kinase C Alpha | 0.0389 |
| PTTG1 | Pituitary Tumor-Transforming 1 | 0.082889 |
| PYGB | Glycogen Phosphorylase B | 0.143943 |
| RPP25 | Ribonuclease P And MRP Subunit P25 | 0.019158 |
| SCPEP1 | Serine Carboxypeptidase 1 | −0.00145 |
| SLC46A3 | Solute Carrier Family 46 Member 3 | −0.0316 |
| SNX7 | Sorting Nexin 7 | 0.133635 |
| TPBG | Trophoblast Glycoprotein | 0.012242 |
| XBP1 | X-Box Binding Protein 1 | −0.12135 |

Returning to FIG. 2b, once the riskscore has been determined, it is compared to a riskscore threshold (step S206). If the riskscore is equal to or above the threshold, there is deemed to be a high risk that the patient will not survive and thus the patient is classified as a high risk patient (step S210). Conversely if the riskscore is below the threshold, there is deemed to be a low risk that the patient will not survive and thus the patient is classified as a low risk patient (step S212). The threshold may for example be the median riskscore of the data which was used to derive the signature and/or the median riskscore of the most significant spits (log-rank $P<0.01$). In other words, the threshold may be the riskscore which most significantly spits the training cohort into relapsing and not-relapsing (i.e. cured) patients.

As an alternative to step S208, the riskscore may be compared to an upper and a lower threshold. If the riskscore is equal to or above the upper threshold, the patient is classified as a high risk patient. If the riskscore is below the lower threshold, the patient is classified as a low risk patient. If the riskscore is between the two thresholds, the patient is classified as an intermediate risk patient. The upper and lower thresholds may be determined as the tertiles of the riskscores determined from the training cohort as explained below.

Once the riskscore has been determined, this may optionally be used to decide on the most appropriate treatment. For example, for a high risk patient, adjuvant chemotherapy is recommended to supplement the surgery. Such treatment results in an improved overall survival rate than chemotherapy alone. This is especially relevant for stage I patients, where a clinical metric for identifying high-risk patients is lacking. Currently stage I patients tend not to receive chemotherapy resulting in under-treatment of approximately 25% of stage I patients who recur within 5 years. By contrast, for a low risk patient, the treatment can be selected from either surgery alone or the combined surgical approach specified above. Both options are equally effective in such cases.

Figure 2C:
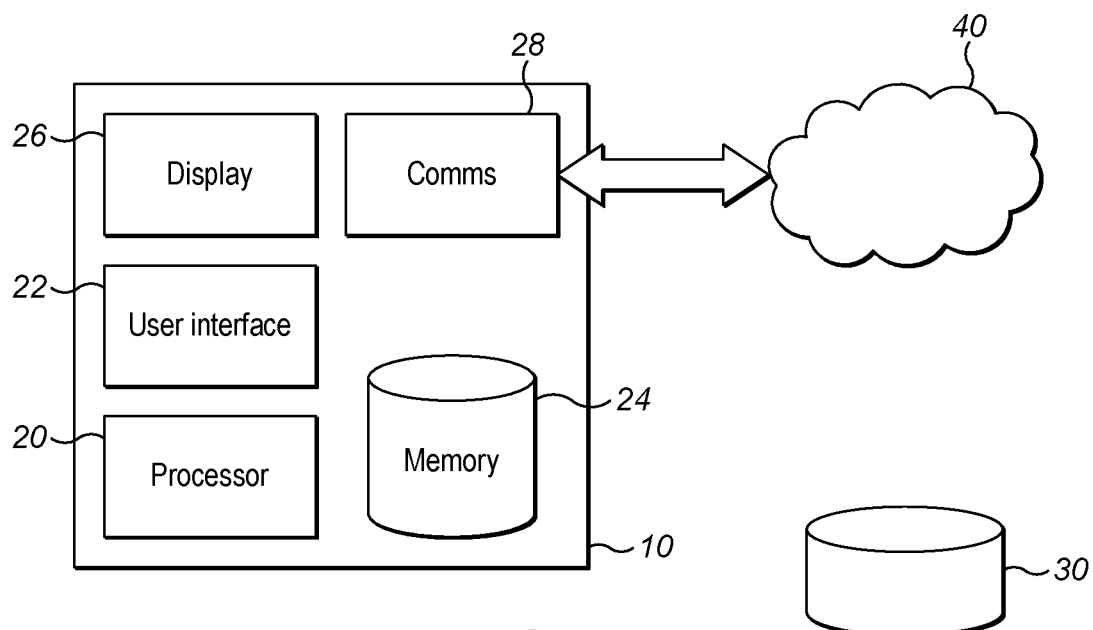
FIG. 2c is a schematic box diagram showing the components of the system for implementing the method of FIG. 2b.
Figure 2D:
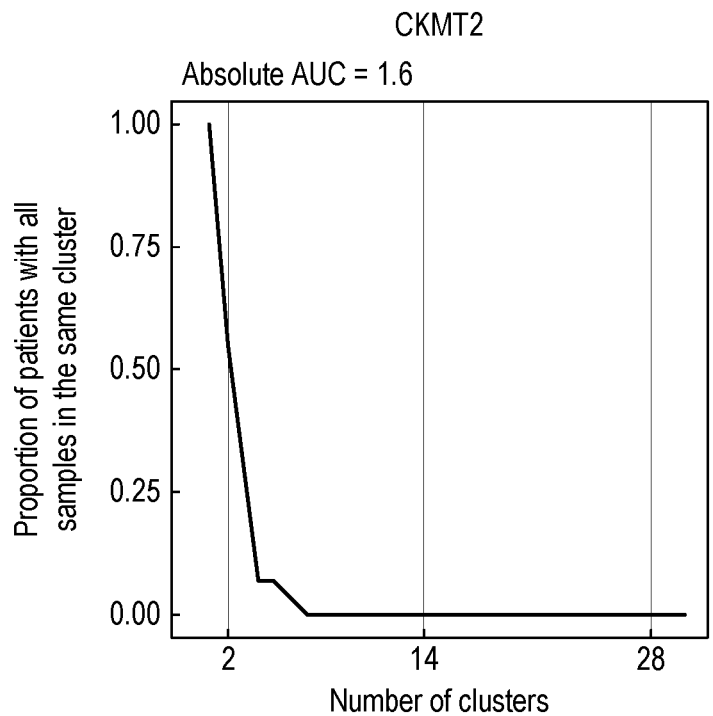
FIGS. 2d and 2e plot the proportion of patients with all samples in the same cluster against the number of clusters for two genes CKMT2 and HOXC11, respectively.
Figure 2E:
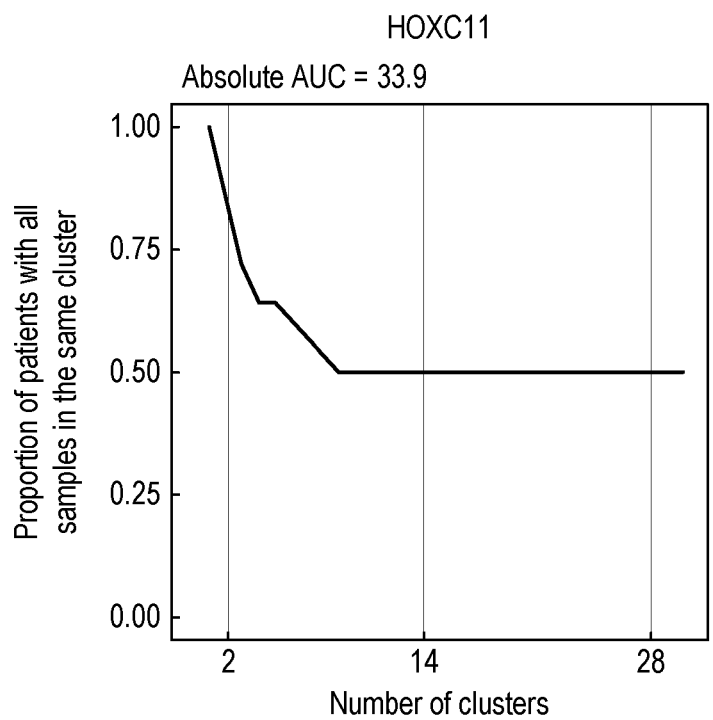
Figure 2F:
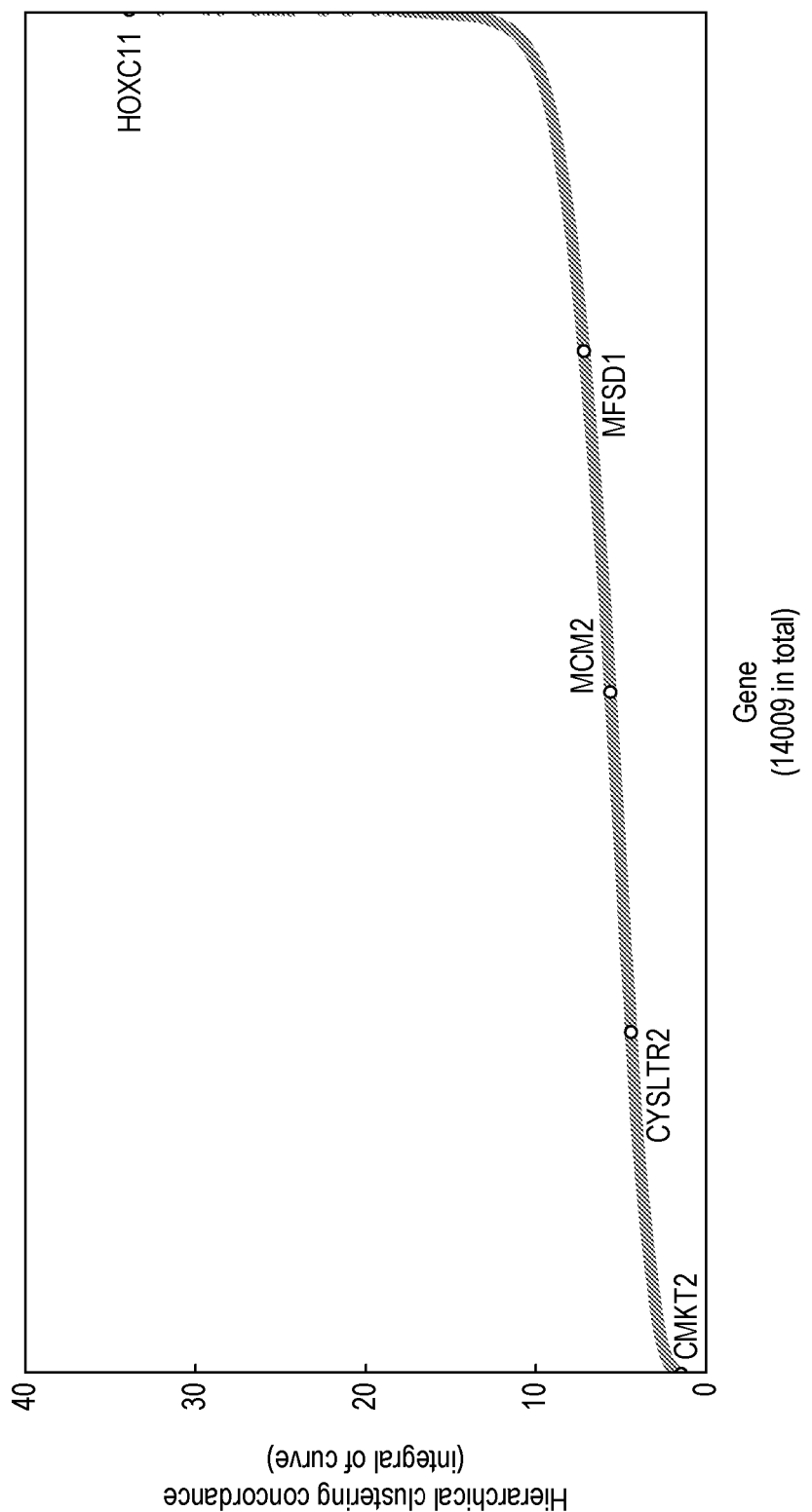
FIG. 2f plots the hierarchical clustering concordance against each gene.

A schematic of an associated system for performing the method is shown in FIG. 2c. The system comprises a computing device 210 which could be a handheld device which is portable for a clinician to transport from patient to patient and an app could be loaded onto the device for calculation of the riskscore. The computing device 210 comprises the standard components such as a processing unit or processor 220, a user interface unit 222 for allowing a user to input information, e.g. determined scores, and a memory 224 for storing the code to perform the calculation and/or the threshold for comparing the calculated riskscore. The user interface may display information or alternatively, there may be a display 224 for displaying information to a user, e.g. a calculated riskscore and/or a suggestion for treatment as described above and a communications module 228 for communicating with other devices and/or accessing the cloud 240, e.g. to process the riskscore. The tissue sample 230 is also shown schematically.

This schematic system may be constructed, partially or wholly, using dedicated special-purpose hardware. Terms such as 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components discussed herein, such functional elements may be combined into fewer elements or separated into additional elements.

FIGS. 3a to 3e illustrate how a clonal expression filter may be created. For each gene an RNA intra-tumour heterogeneity value and an RNA inter-tumour heterogeneity value is calculated. These per-gene metrics may quantify variability by the standard deviation between regions within the same tumour to generate a value for intra-tumour heterogeneity and quantify variability by the standard deviation between the same tumour regions from different tumours to generate a value for inter-tumour heterogeneity. They may be calculated using multi-region RNAseq data (normalised count values).

FIGS. 3a to 3e plot the data for tumour samples from the dataset collected from 100 NSCLC patients enrolled in the TRACERx lung cancer study sponsored by University College London. Multi-region sampling was performed to obtain DNA and RNA sequentially from the same tissue. Whole exome sequencing was performed on DNA samples. Of the cohort of 100 tumours, RNA samples of sufficient quality were obtained from 174 regions of 68 tumours. Of these, at least two samples were available from 48 tumours.

Further processing may be performed as necessary. For example, alignment was performed, for example using the STAR package described in "STAR:ultrafast universal RNA-seq aligner" by Dobin et al published in Bioinformatics 29, 15 to 21 (2013) to map reads to the human genome. Transcript expression was quantified, for example using the RSEM package described in "RSEM: accurate transcript quantification from RNA-Seq data with or without a reference genome" by Li et al published in BMC Bioinformatics 12, 323 (2011) to generate count and transcript per million (TPM) expression values. An expression filter was applied, keeping genes with at least 1 TPM in at least 20% (30/156) of tumour samples. Lastly, a variance stabilizing transformation was applied to counts from filtered genes (assuming a negative binomial distribution for count values) using the DESeq2 package described above. Homoscedastic and library size normalised count values were output to be used as described below. In this example, there may be 19206 genes to consider.

Figure 3A:
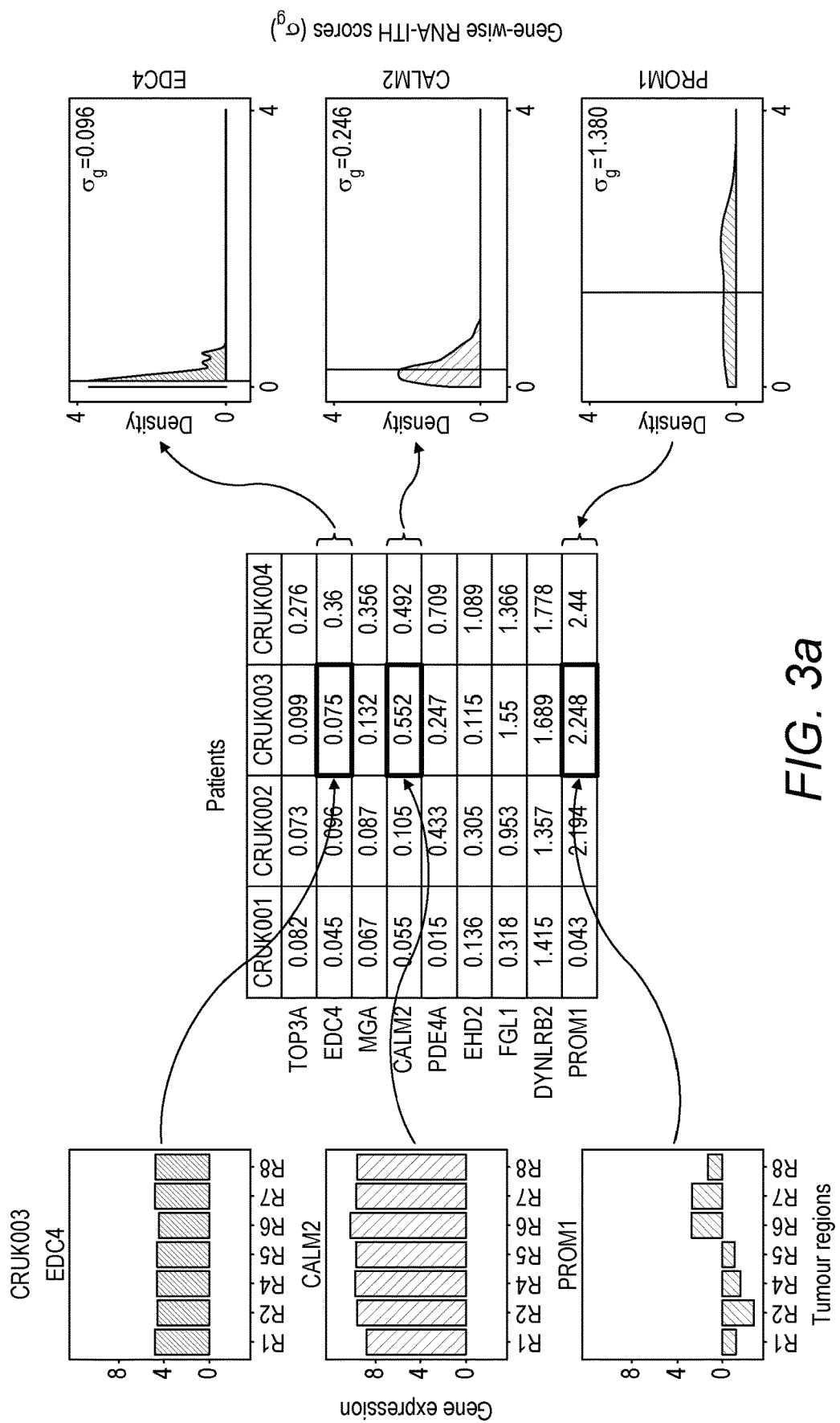
FIG. 3a illustrates the steps in calculating RNA intratumour heterogeneity for a plurality of genes.

As shown in FIG. 3a, for each patient (e.g. CRUK0003) the gene expression at multiple locations (e.g. R1 to R8) for each gene is determined. The plots on the left side of FIG. 3a show the gene expression at a plurality of locations for EDC4, CALM2 and PROM1 as examples. For a given tumour, the standard deviation of expression values for a particular gene across tumour regions may be calculated yielding a gene-specific, patient specific measure of RNA-intra-tumour heterogeneity ($\sigma_{g,p}$). For the example patient, these are shown in the table in the centre of FIG. 3a and for the three genes are 0.075, 0.552 and 2.248 respectively. Thus, EDC4 has little variation across the tumour but PROM1 has a significant variation. This may then be repeated for all genes and then for all tumours, generating a matrix of $\sigma_{g,p}$ values which is depicted as a table showing the patients (p) in columns and the genes (g) in rows in this example.

Gene-wise RNA-intra-tumour heterogeneity values may be summarised as the average (median) value per gene across all tumours in the cohort ($\sigma_g$). These values may be determined for example by plotting graphs such as those shown on the right side of FIG. 3a. For the three example genes, the $\sigma_g$ values are 0.096, 0.246 and 1.380 respectively. Alternatively, patient-wise RNA-ITH values may be summarised as the average (median) value per tumour across all expressed genes in the cohort ($\sigma_p$).

Figure 3B:
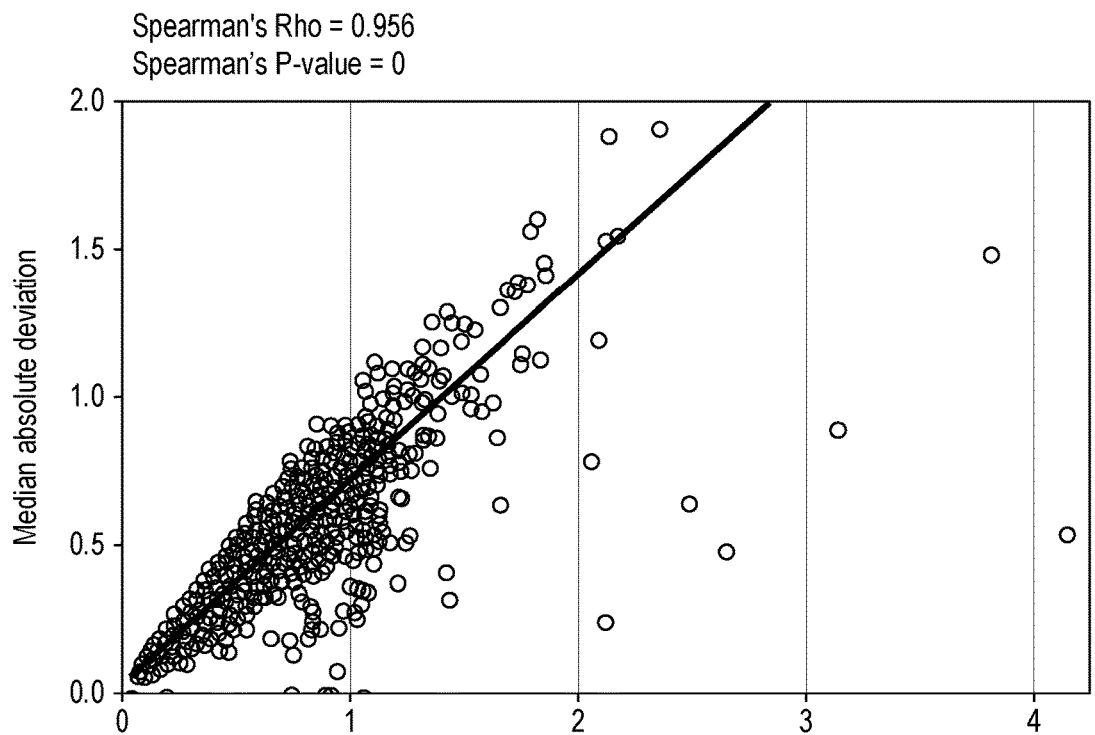
FIG. 3b plots the median absolute deviation (MAD) against the standard deviation scores for each gene.
Figure 3C:
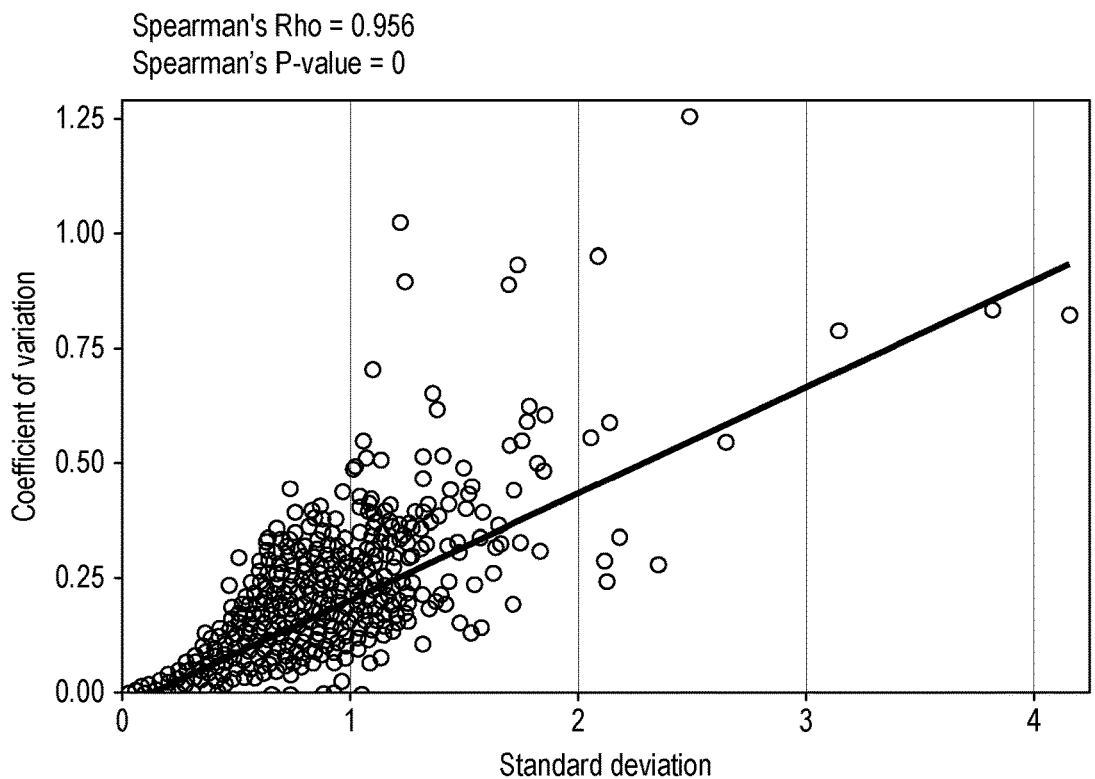
FIG. 3c plots the coefficient of variation (CV) against the standard deviation scores for each gene.

FIG. 3b plots the median absolute deviation (MAD) against the standard deviation scores for each gene. Similarly, FIG. 3c plots the coefficient of variation (CV) against the standard deviation scores for each gene. FIGS. 3b and 3c show that MAD and CV are alternative metrics for the quantification of gene-wise RNA-ITH which show good agreement with standard deviation scores.

Figure 3D:
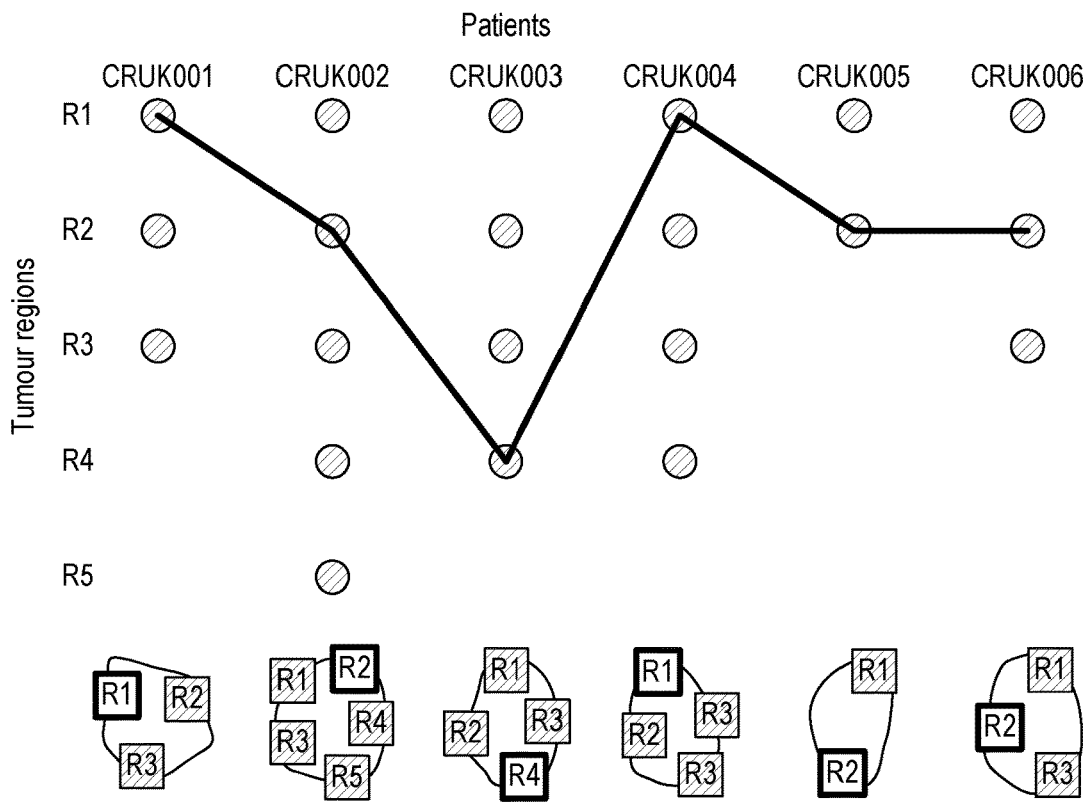
FIG. 3d illustrates the random sampling process to calculate the RNA inter-tumour heterogeneity measure.

As shown in FIG. 3d, an inter-tumour heterogeneity measure may be derived for each gene by randomly sampling one region per patient, for example R1 for patient CRUK001, R2 for patient CRUK002 and so on. The standard deviation across the resulting single-biopsy cohort may then be taken. The random sampling and calculating of the standard deviation may be repeated multiple times (e.g. ten) to take the average score across iterations. As a check, the same method may also be applied to the TCGA NSCLC data-set which is a true single-biopsy cohort. Such a check found good agreement with scores calculated within the TRACERx cohort (PMCC=0.94, P<0.001), which indicates calculation of inter-tumour heterogeneity scores is reproducible.

Figure 3E:
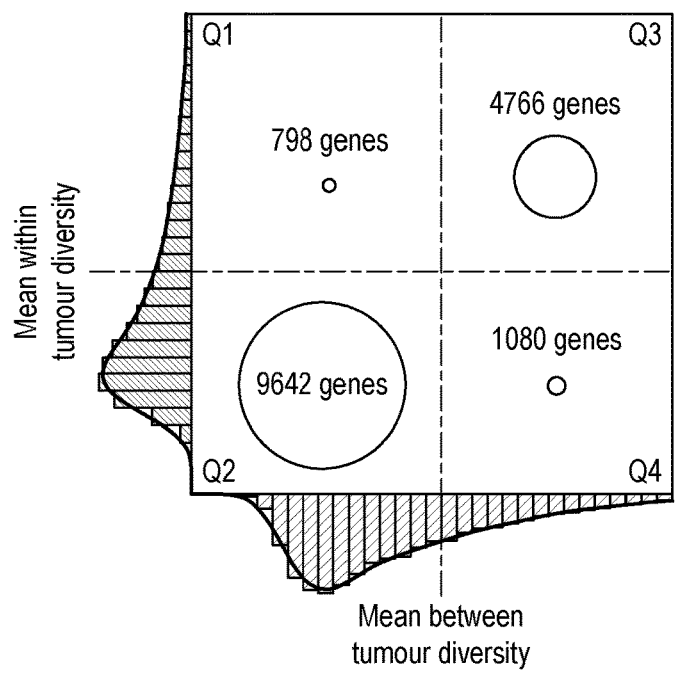
FIG. 3e plots values for RNA intra-tumour heterogeneity (y-axis) against values RNA inter-tumour heterogeneity (x-axis) for a plurality of genes.

FIG. 3e plots values (also termed scores and the terms may be used interchangeably) for RNA intra-tumour heterogeneity (y-axis) against values RNA inter-tumour heterogeneity (x-axis) for each gene. The plot in FIG. 3b is spilt into quadrants by the mean intra-tumour heterogeneity value (dashed horizontal line) and mean inter-tumour heterogeneity value (dashed vertical line). The quadrants are numbered Q1, Q2, Q3 and Q4 with the number of genes per quadrant indicated. Q1 represents low inter-tumour heterogeneity and high intra-tumour heterogeneity value genes and contains 798 genes. Q2 represents low inter-tumour heterogeneity and low intra-tumour heterogeneity value genes and contains 9642 genes. Q3 represents high inter-tumour heterogeneity and high intra-tumour heterogeneity value genes and contains 4766 genes. Q4 represents high inter-tumour heterogeneity and low intra-tumour heterogeneity value genes and contains 1080 genes. Genes in Q2 and Q4 exhibit homogenous expression within tumours (i.e. low inter-tumour heterogeneity) which may restrict sampling bias. However, in Q2 the genes also have low inter-tumour heterogeneity which means that they exhibit homogenous expression between different tumours and are thus not informative for patient stratification into high/low risk groups. Accordingly, the group of genes in Q4 is the more useful and thus the clonal expression filter may filter out all genes outside the Q4 quadrant, i.e. genes having both an inter-tumour heterogeneity value above the inter-tumour threshold (e.g. the median value) and an intra-tumour heterogeneity value below the intra-tumour threshold (e.g. the median value).

FIGS. 4a to 4e illustrate example results of the final optional step of the method of FIG. 2a which is to evaluate the prognostic accuracy of the output (ORACLE) signature using validation data. In this example, the validation data is taken from the "Uppsala II" dataset which is an independent cohort of early stage LUAD patients (UII, n=103, stage I to III). The validation data comprises pre-processed Uppsala RNAseq and clinical data downloaded for 170 NSCLC patients (103 LUAD+67 LUSC) enrolled in the Uppsala NSCLC II cohort from the Gene Expression Omnibus. The cohort are described in "Profiling cancer testis antigens in non-small-cell lung cancer" by Djureinovic et al published in JCL Insight 1 (2016).

Gene information was extracted from the data set using known step. For example, alignment to the human genome was performed, e.g. using the TopHat package described in "TopHat2: accurate alignment of transcriptomes in the presence of insertions, deletions and gene fusions" by Kim et al publication in Genome Biol 14, R36 (2013). Raw reads were then calculated, for example using the Subread package described in "The Subread aligner: fast, accurate and scalable read mapping by seed-and-vote" by Liao et al published in Nucleic Acids Res 41, e108 (2013). Gene IDs were converted to HGNC IDs using the biomaRt package described in "Mapping Identifiers for the Integration of Genomic Datasets with the R/Bioconductor package biomaRt" by Durinck et al publications in Nat Protoc 4, 1184-1191 (2009). Max values were then selected for multi-mapping probes. Lowly expressed genes, which were identified in the training dataset described above, were filtered from the validation dataset and a variance stabilizing transform was applied using the DESeq2 package described above to output normalized count values. Additional clinical information (e.g. treatment status and tumour size) was also obtained.

Figure 4A:
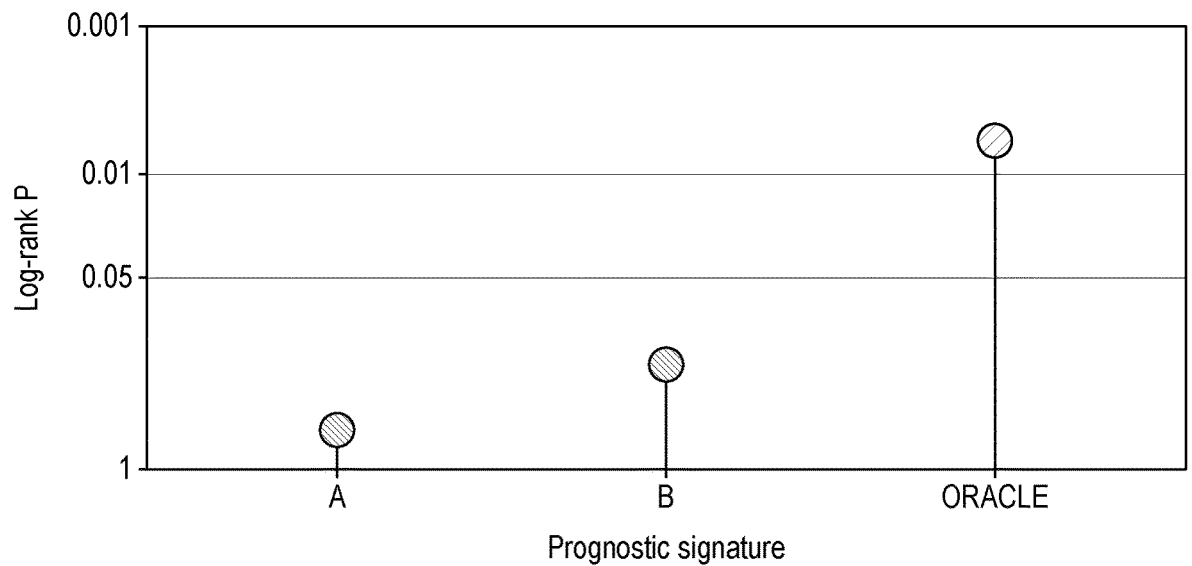
FIG. 4a plots the prognostic value for each of three signatures in a validation cohort.

FIG. 4a compares the performance of the output 23 gene signature to similar signatures based on known papers. Signature A is based on a signature construction pipeline described in "Development of a RNA-seq Based Prognostic Signature in Lung Adenocarcinoma" by Shukla at al in JNCL J Natl Cancer Inst 109 (2017). The signature is derived from the genes identified in the Shukla paper and uses standard techniques to select several genes for the signature. For example, using the training dataset from the TCGA database, in particular the LUAD patients, a univariate Cox regression analysis is performed, and a primary prognostic filter is applied (univariate Cox analysis P<0.00025) to reduce the number of genes identified in the Shukla paper to 108. Another prognostic filter, this time univariate Cox analysis FDR<0.02 reduces the 108 genes to 15. Finally, a forward conditional stepwise regression is applied to yield a 6-gene signature. The steps outlined in the Shukla paper have thus been followed but the different training data has yielded a 6-gene signature rather that the prognostic model containing 4 genes on page 4 of Shukla.

Signature B is based on the signature construction pipeline described in "A practical molecular assay to predict survival in resected non-squamous, non-small lung cancer: development and international validation studies" by Kratz et al published in the Lancet 379, 823-832 (2012). In the development of signature B, all the genes identified in the papers listed in the table in the background section are first collated in a list. Using the training dataset from the TCGA database, in particular the LUAD patients, a univariate Cox regression analysis is performed, and a primary prognostic filter is applied (univariate Cox analysis P<0.00025) to reduce the number of genes identified to 249. A secondary prognostic filter is applied by short-listing only the genes which are cancer-related to reduce the number from 249 to 56. Finally, a lasso regression is applied to yield a 24 gene prognostic signature. As with signature A, this signature B is thus derived using the methodology described in the Kratz paper but results in a different selection of genes because of the training cohort. Both signatures are comparable with the 24 gene signature described above.

FIG. 4a plots the prognostic value for each of three signatures. The prognostic accuracy of the three signatures is tested using the validation data from the Uppsala dataset. As shown the signature resulting from the process shown in FIG. 2a predicted significant survival risk (log-rank P=0.006) and outperformed both signatures A and B. In other words, FIG. 4a shows that using the riskscore calculated using the signature derived by the FIG. 2a process, patients in the validation cohort may be more successfully spilt into subgroups with significantly different survival times than using the riskscores from signatures A and B.

Figure 4B:
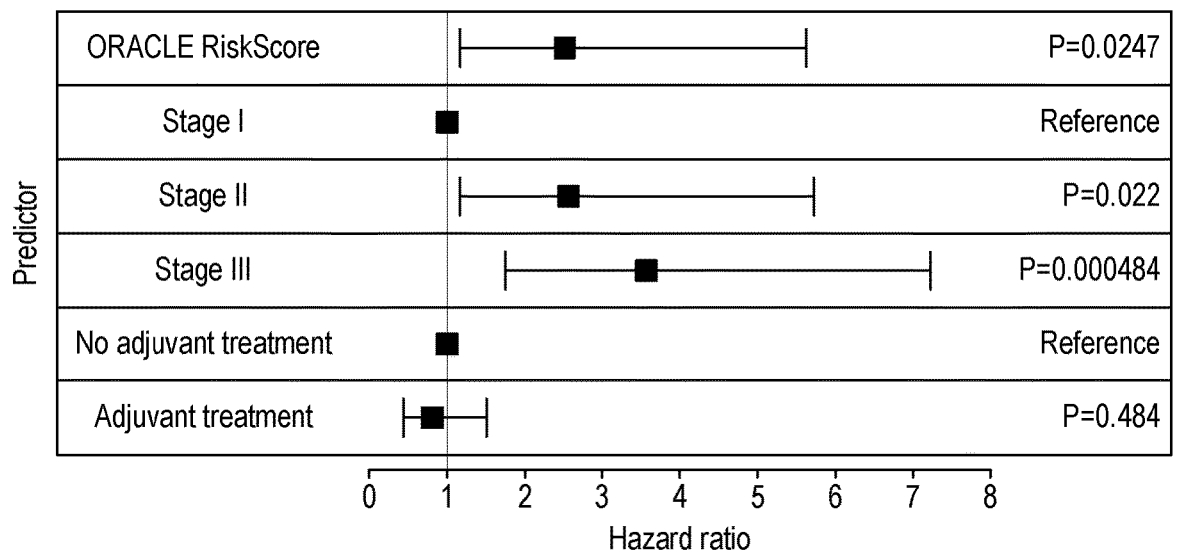
FIG. 4b shows a Forest plot with predictive value over known risk factors.

FIG. 4b is a Forest plot and shows the predictive value of the new signature when combined with other known risk factors. In FIG. 4b, a multivariate (rather than the previous univariate) analysis is performed to demonstrate that the calculated riskscore (which is input as a continuous variable) maintains significance even when clinical information is integrated to predict survival. The relative risk of death (hazard score) is shown as the solid block as a combined function of tumour stage (e.g. I to III), therapy status (no or some adjuvant treatment) and the risk score calculated using the output (ORACLE) signature. The 95% confidence level is also indicated by the bars. The higher the hazard ratio, the greater the risk of death and not unsurprisingly, the stage III patients have the highest values. FIG. 4b shows that the output signature is significant when using multivariate analysis with tumour stage and treatment status (Cox MVA P=0.0247) because the signature provides additional prognostic information.

Figure 4D:
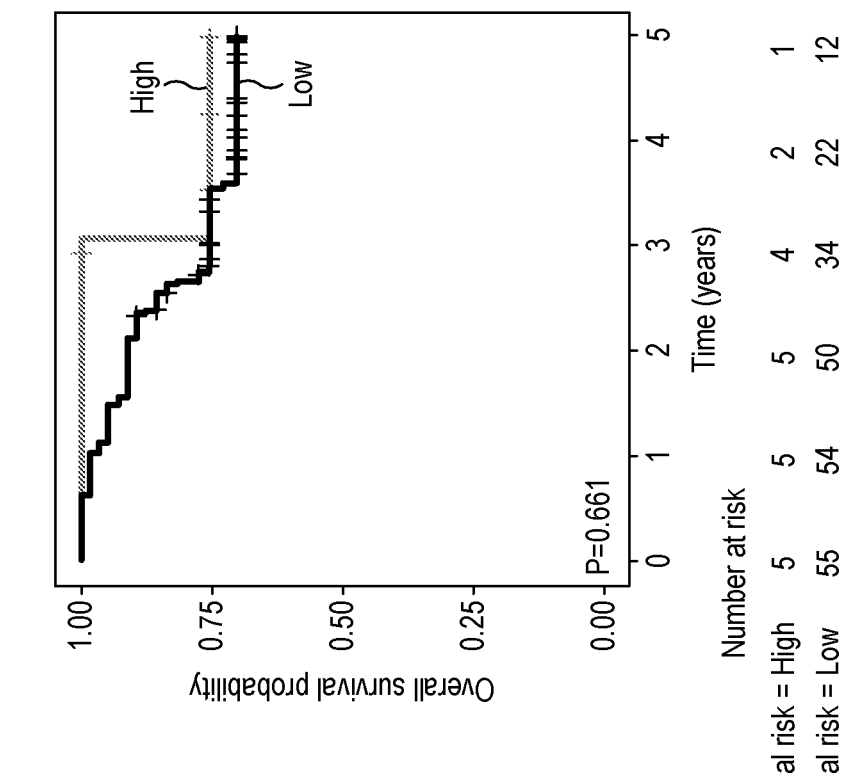
FIGS. 4c, 4d and 4e plot prognostic value of substaging criteria, current clinical guidelines for chemotherapy and the output signatures in stage I patients where improved risk prediction could impact clinical decision-making.
Figure 4C:
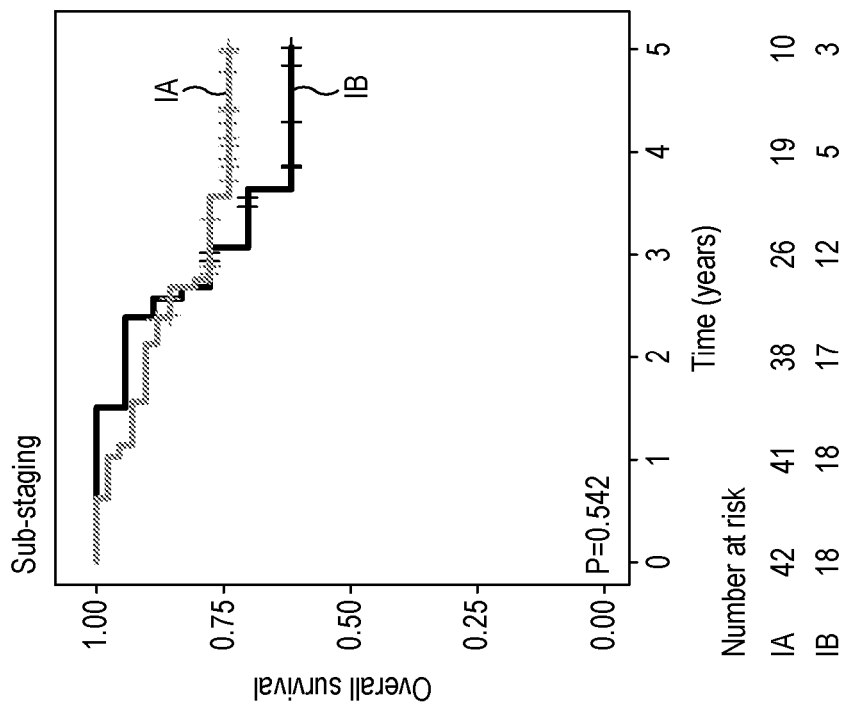
Figure 4E:
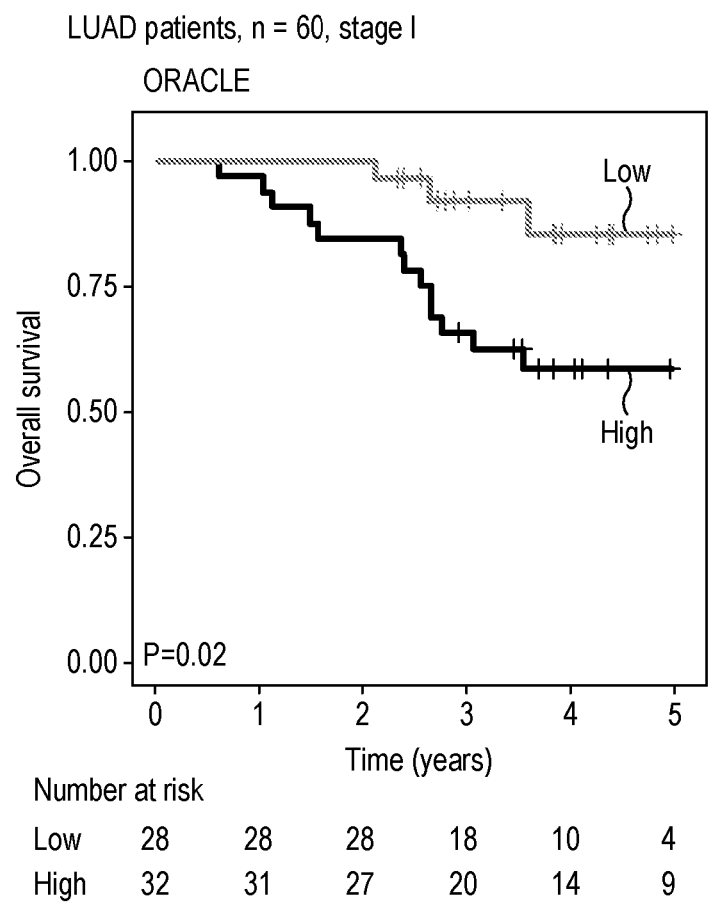
Figure 4F:
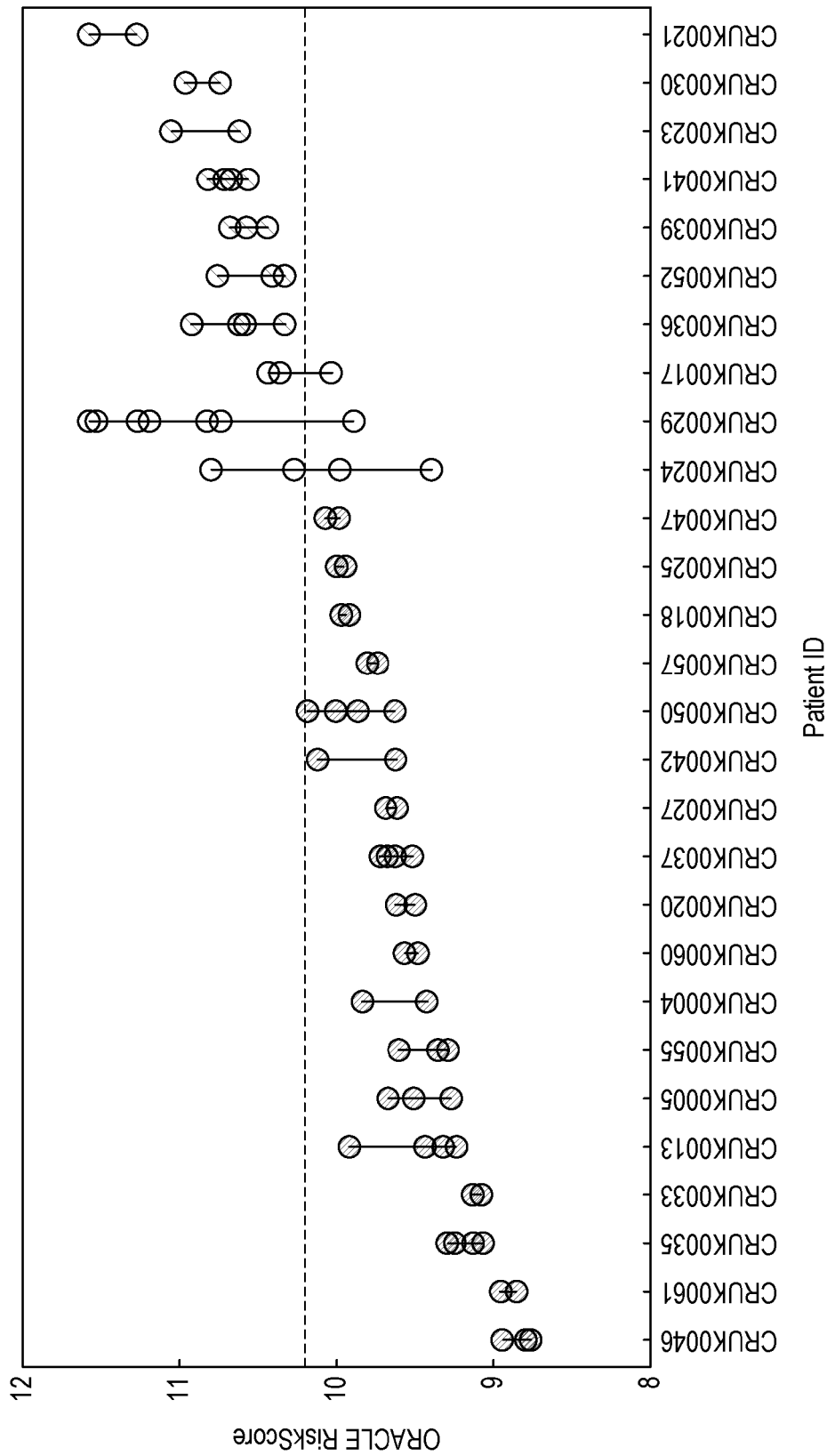
FIG. 4f plots the riskscore from the output signature for a plurality of patients.

FIGS. 4c to 4e show the clinically actionable information in stage I patients. There are approximately 60 such patients in the validation dataset. FIG. 4c shows the stage I patients divided into two groups: IA (n=42) and IB (n=18) according to substaging criteria (log-rank P=0.52). Classifying the patients in this way does not effectively stratify the patients into those having a good overall survival rate and a lower overall survival rate. Similarly, FIG. 4f shows the stage I patients classified into high and low risk patients based on tumour size. Current clinical guidelines stage I LUAD patients are that patients having stage IB tumours greater than 4 cm in size are though to be high-risk and other patients (i.e. with stage IA tumours or stage IB tumours less than 4 cm) are low risk. In the group of 60 patients, just five patients are classified as high risk. As shown in FIG. 4d, the patients are not well stratified into those having a good overall survival rate and a lower overall survival rate.

FIG. 4e shows the stage I patients divided into two groups: a high risk group (red) and a low risk group (blue) using the output (ORACLE) signature. As shown, this split is much more effective in predicting the survival rate of the patients.

FIG. 4f shows the effect of tumour sampling bias on the output (ORACLE) signature. Tumour regions are classified as either "high-risk" or "low-risk" using the calculated risk scores. Individual patients are then assessed for discordant classification whereby different regions from the same tumour may be classified as harbouring distinct profiles of molecular risk. As shown just 3/28 patients (i.e. 11%) are discordant and this is a much lower rate of discordance than those shown in FIGS. 1c and 1d.

Figure 4G:
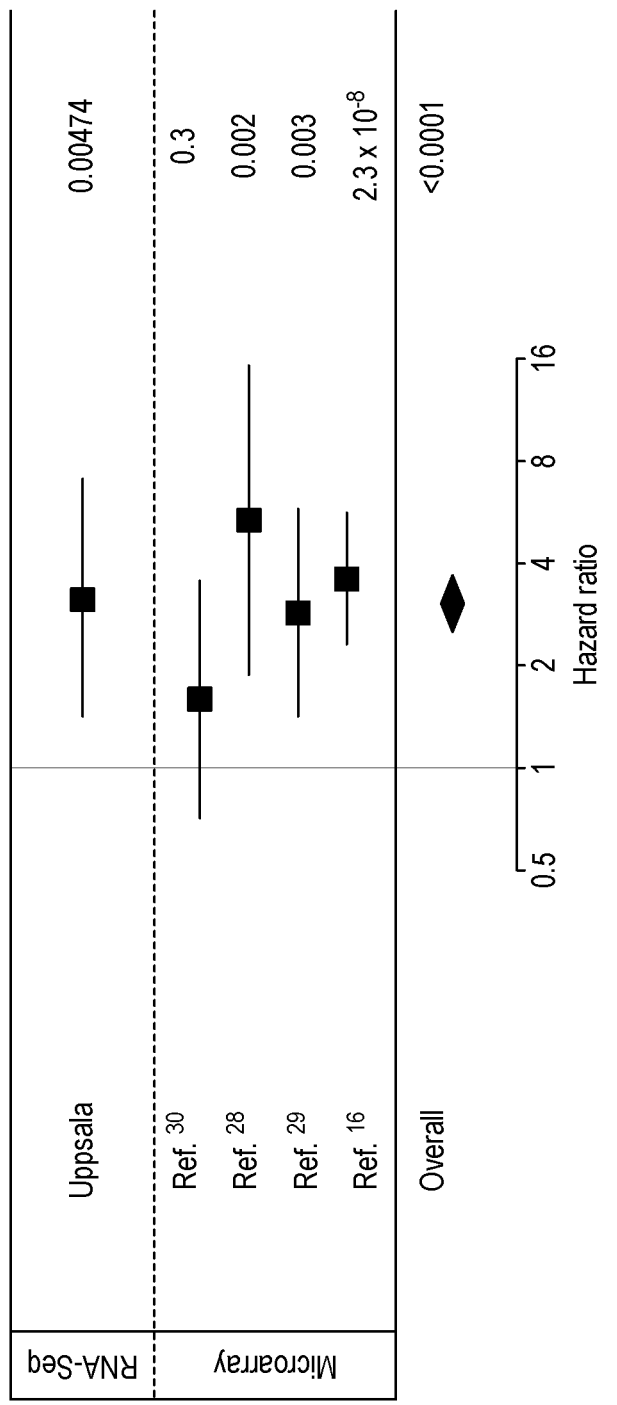
FIG. 4g plots prognostic value assessment using a RNA-Seq dataset and four microarray datasets.

FIG. 4g plots prognostic value assessment using a RNA-Seq dataset and four microarray datasets. To investigate concordance across multiple cohorts, the output (ORACLE) signature was applied to four microarray datasets. Specifically, prognostic value of the output (ORACLE) signature was assessed in a meta-analysis across five validation cohorts of patients with LUAD (n=904 patients with stage I-III LUAD). Univariate Cox analysis was performed in one RNA-Seq dataset and four microarray datasets. In the microarray cohorts, 19 of the 23 genes were available for analysis (ASPM, CDCA4, FURIN, GOLGA8A, ITGA6, JAG1, LRP12, MAFF, MRPS17, PLK1, PNP, PPP1R13L, PRKCA, PYGB, SCPEP1, SLC46A3, SNX7, TPBG, XBP1). Hazard ratios with a 95% confidence interval are shown for each cohort and are plotted on a natural log scale. It was expected that the output signature's performance would be poorer, as only 19 of the 23 genes were matched to the microarray probe sets, and signature weights that were trained on RNA-Seq data were used. However, ORACLE significantly associated with survival in three of the four microarray datasets. Meta-analysis considered all validation cohorts—the diamond indicates the hazard ratio for the meta-analysis of the five validation cohorts—which shows that ORACLE was significantly associated with the outcome with an overall hazard ratio of 3.57. These data indicate that survival associations resistant to differences in expression profiling technology can be obtained by controlling for RNA-ITH in biomarker design. Further information on this analysis can be found in "A clonal expression biomarker associates with lung cancer mortality" by D. Biswas et al, Nature Medicine 25, 1540-1548 (2019).

Figure 4H:
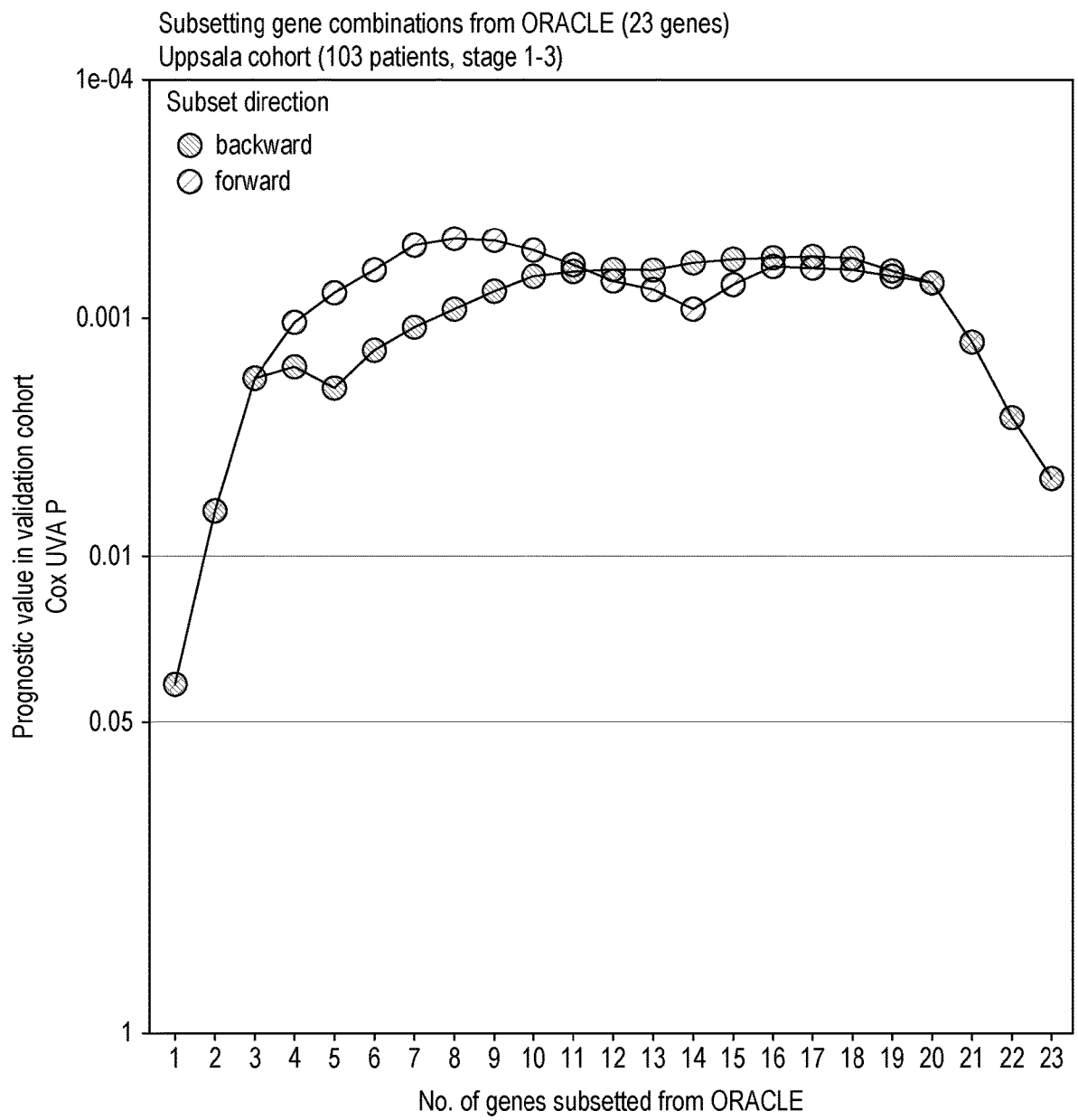
FIG. 4h shows a plot indicating that any subset of the ORACLE signature may have a prognostic value.

FIG. 4h plots the prognostic value for combinations of 1 to 23 genes selected from the ORACLE signature. Two procedures for selecting gene combinations from the full ORACLE signature were considered, as computationally efficient alternatives to an exhaustive search through every combination of the 23 genes. Backward subsetting began with the full model containing all 23 genes, all 22 gene combinations were evaluated, then the best combination with highest prognostic significance was chosen. This procedure continued iteratively, removing genes one-at-a-time, until one gene remained. Forward subsetting began with a model containing no genes, and then added genes yielding the highest prognostic significance to the model, one-at-a-time, until all 23 genes were included. Importantly, the weights for each gene were not re-trained, so each combination was evaluated as a subset of the full ORACLE signature defined above. These data indicate that any combination of two or more of the 23 genes of the ORACLE signature may have a prognostic value. Data from these two procedures is shown in Appendix A.

Figure 5A:
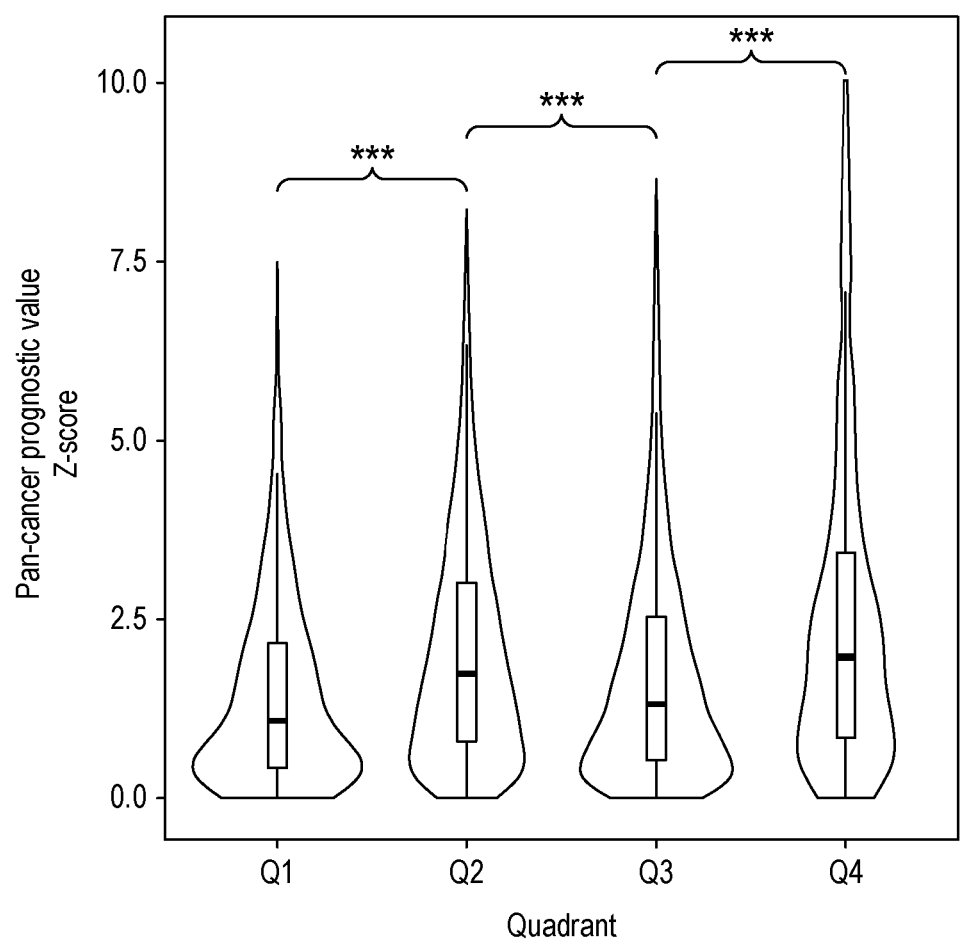
FIG. 5a plots the prognostic association of RNA heterogeneity quadrants across cancer types.
Figure 5B:
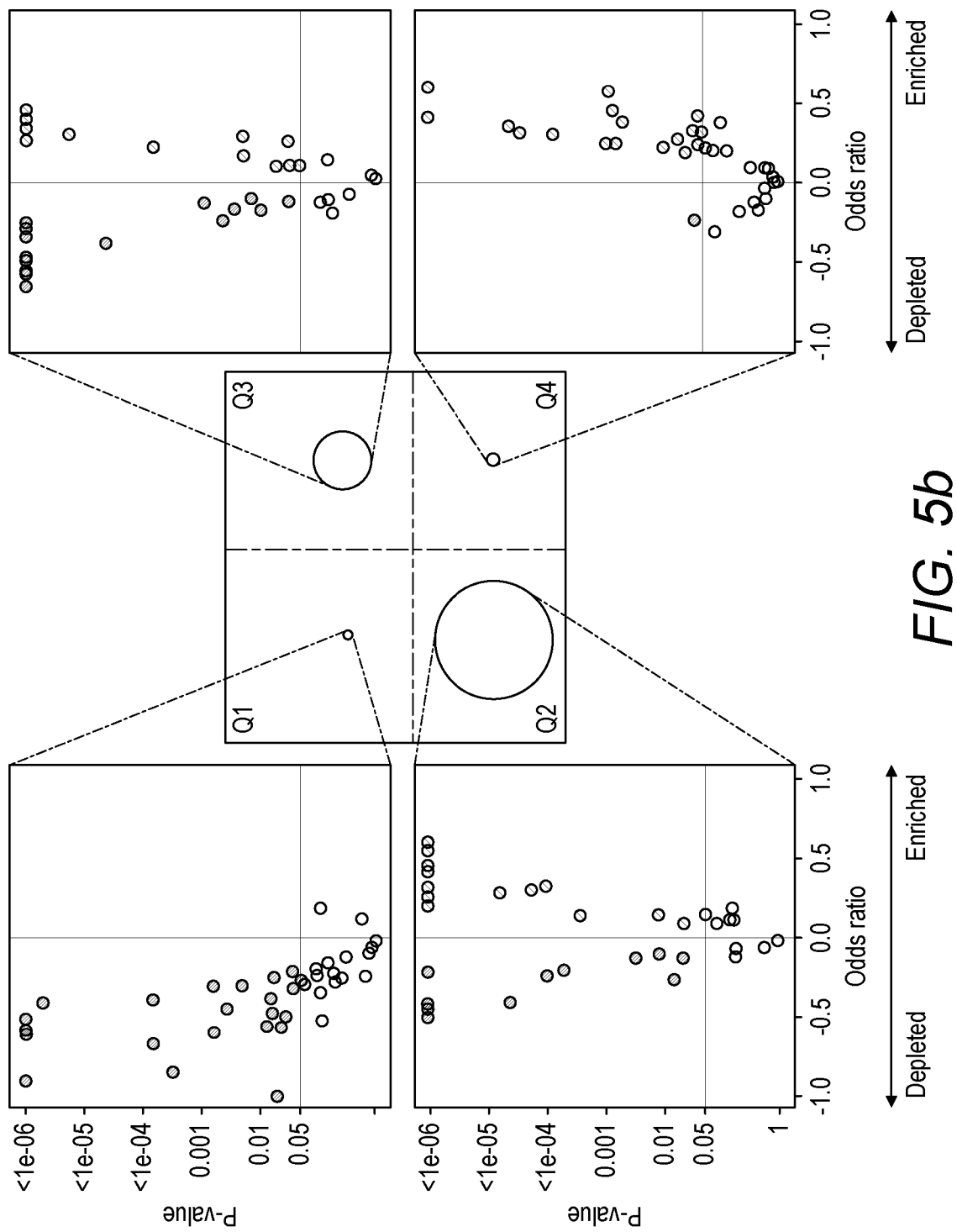
FIG. 5b compares the performance of genes within each quadrant for a plurality of cancer types to determine whether the quadrants are enriched or depleted in prognostic genes.

FIGS. 5a and 5b illustrate that the method described above in FIG. 2a may hold prognostic relevance across other cancer types. The clonal expression filter described in FIGS. 3a to 3f was generated by leveraging the full multi-region RNAseq dataset from the TRACERx lung cohort incorporating data from multi-region LUSC tumours and other NSCLC histologies. This data was then used to calculate an intra-tumour heterogeneity score and an inter-tumour heterogeneity for each gene using the same gene-wise metric described above. The genes are divided into four quadrants as described above.

The proportion of each of the genes in each of the quadrants which give a pan-cancer significant prognostic value was then assessed and is displayed in FIG. 5a. For example, Pan-cancer gene-wise prognostic values may be downloaded from the PRECOG resource described in "The prognostic landscape of genes and infiltrating immune cells across human cancers" by Gentles et al published in Nat Med 21, 938-945 (2015). The PRECOG resource is a meta-dataset summarizing 166 microarray datasets covering 39 distinct malignant histologies. The dataset comprises Z-scores which have previously been calculated using a Cox univariate regression analysis. The genes having a |z| score>1.96 (which is equivalent to a two-sided P<0.05) are selected. Consistent with the analysis in FIGS. 3a to 3f, genes in quadrant Q4 (i.e. high inter-tumour heterogeneity and low intra-tumour heterogeneity value genes) exhibited a significantly higher pan-cancer Z score (reflecting significant prognostic ability) compared to all other quadrants.

FIG. 5b also compares the performance of genes within each quadrant to determine whether the genes are enriched or depleted in prognostic genes. Each point in FIG. 5b corresponds to one out of 33 cancer types sourced from the PRECOG database. The number of prognostically significant genes (|z| score>1.96) per NSCLC RNA heterogeneity quadrant is indicated for each cancer types as non-significant (gray), significantly enriched (red) or significantly depleted (blue). As shown in FIG. 5b, the genes in Q4 were significantly enriched in prognostic genes in 49% (19/39) of cancer types and only significantly depleted in head and neck cancer 3/% (1/39). Conversely, genes in Q1 (low inter-tumour heterogeneity and high intra-tumour heterogeneity value genes) were not significantly enriched in any cancer types and depleted in 56% (22/39). Genes in Q2 (low inter-tumour heterogeneity and low intra-tumour heterogeneity value genes) and Q3 (high inter-tumour heterogeneity and high intra-tumour heterogeneity value genes) showed similar numbers of depleted and enriched cancer types.

Figure 6A:
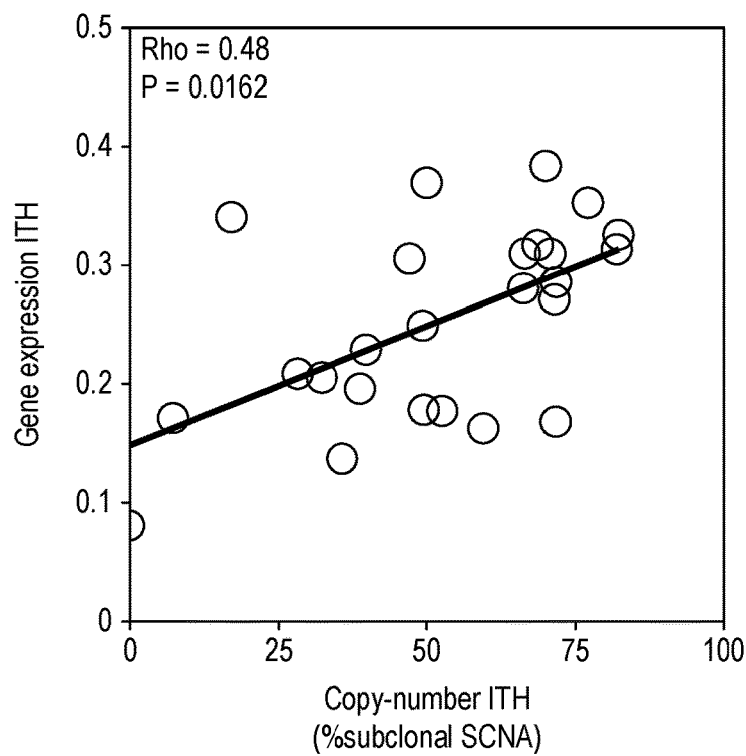
FIG. 6a plots gene expression ITH against copy number ITH.
Figure 6B:
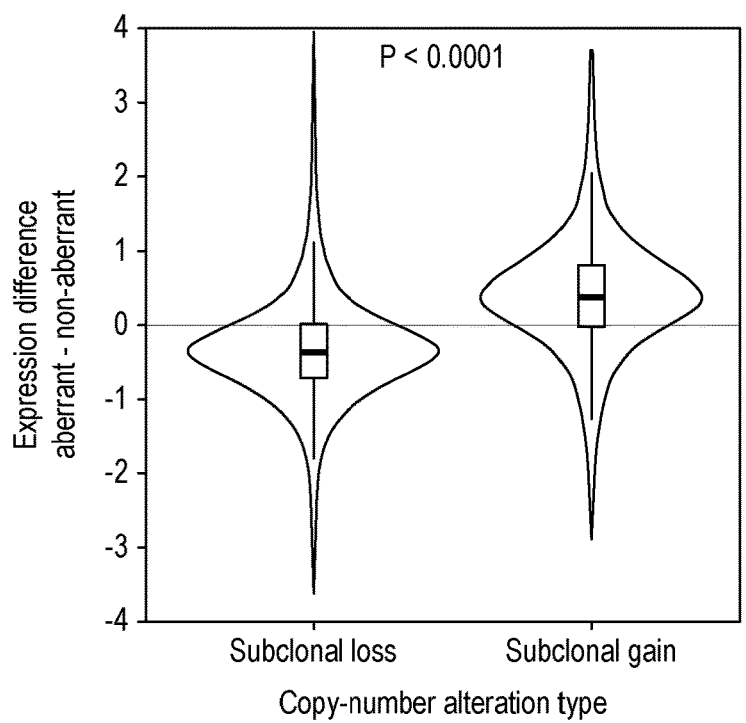
FIG. 6b shows the expression difference for subclonal chromosomal copy-number changes (losses and gains respectively)
Figure 6C:
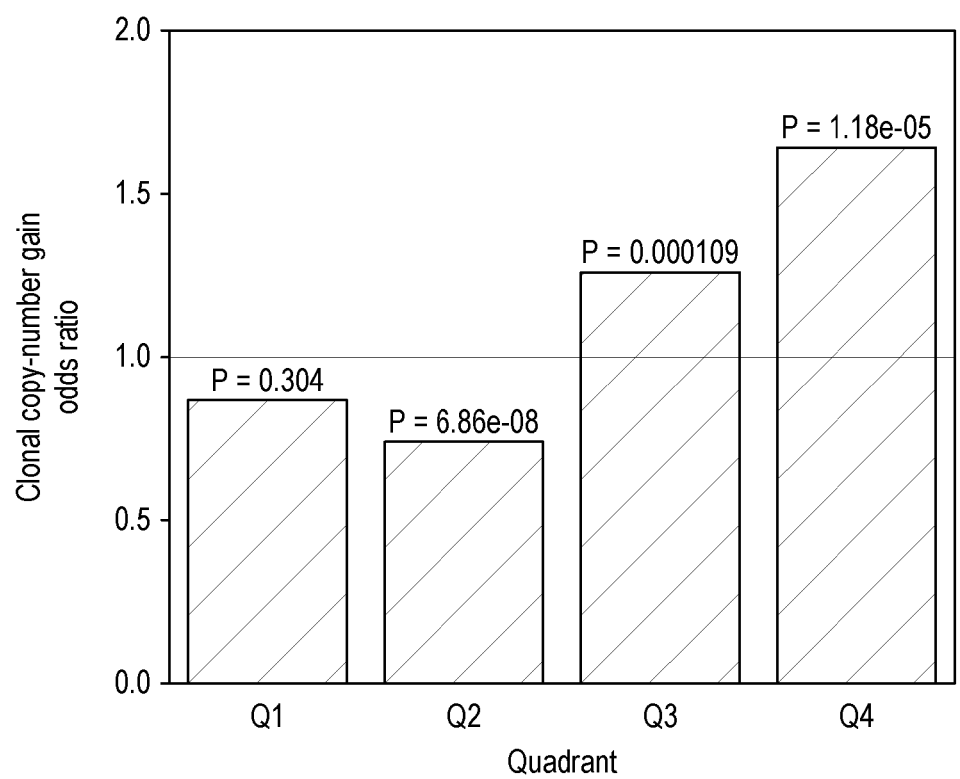
FIG. 6c plots clonal copy-number gains by RNA heterogeneity quadrant.

FIGS. 6a to 6c explore the genomic mechanisms underpinning RNA-ITH. The relationship between RNA-ITH scores calculated as described above using the multi-region RNAseq data and a copy number heterogeneity quantified using multi-region WES data described in "Tracking the Evolution of Non-Small Cell Lung Cancer" by Jamal-Hanjani et al published in N Engl J Med 376, 2109-2121 (2017) is first considered. FIG. 6a correlates gene expression ITH correlated with copy number ITH. From the TRACERx LUAD cohort, patient-wise RNA-ITH scores are plotted against patient-wise SCNA-ITH scores. FIG. 6a shows that there is a significant correlation between the median RNA-ITH score per patient and the percentage of subclonal SCNA events per patients ($R_s$=0.48, P=0.0162). This indicates that SCNA-ITH may contribute to transcriptomic heterogeneity.

FIG. 6b shows that there is a highly significant association between subclonal copy-number gains and increased expression as well as between subclonal copy-number losses and decreased expression (P<0.001). This data indicates an association between chromosomal copy number gains and losses at the subclonal level and gene transcription and that RNA-ITH reflects on-going CIN and likely selection of heterogeneous DNA copy number events.

FIG. 6c shows the clonal copy number gains odds ratio for each quadrant. FIG. 6c assesses the relative enrichment of genes within each quadrant most commonly subjected to clonal copy number gain (upper quartile) versus the genes that rarely showed clonal copy number gain (lower quartile) in the TRACERx cohort. FIG. 6c shows that there is a highly significant enrichment of Q4 genes subject to clonal copy number gain events in TRACERx (P=1.18e-05, Fisher's exact test) and to a lesser extent Q3 genes (P=0.000109, Fisher's exact test). By contrast, there is a depletion of Q2 genes (P=6.86e-08, Fisher's exact test). This data suggests that homogeneous expression across a tumour is likely rooted in clonal DNA copy number alterations, selected early in tumour evolution.

Figure 6D:
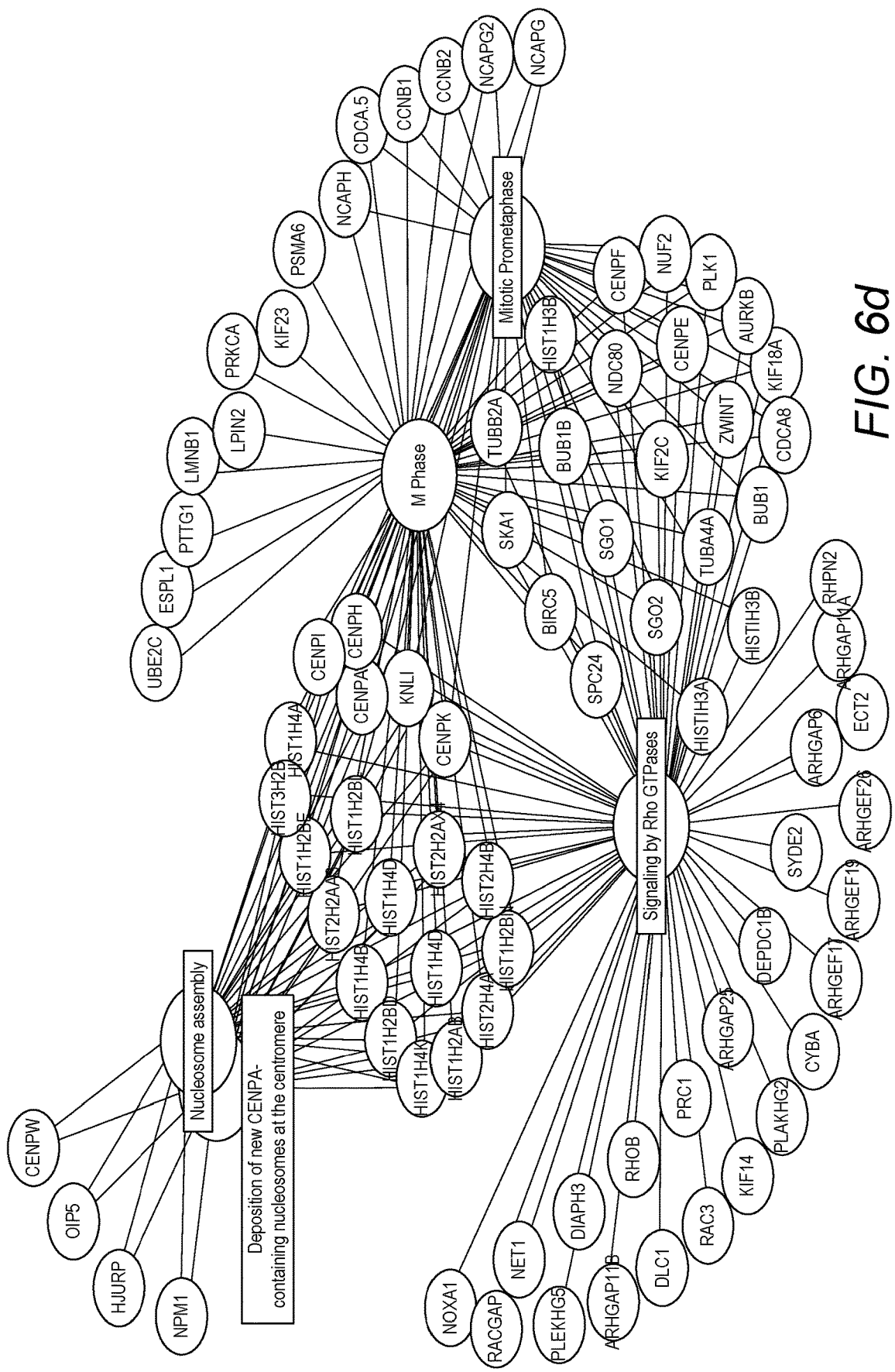
FIG. 6d plots the enriched reactome pathways in RNA heterogeneity quadrant Q4.

FIG. 6d shows the enriched reactome pathways in Q4 and these relate to cell proliferation, including mitosis, nucleosome assembly and epigenetic regulation. By contrast, the same analysis of the pathways for the genes in the other quadrants showed that the Q1 genes showed no significant enrichment, the Q2 genes showed involvement in RNA splicing processing and the Q3 genes showed involvement in GPCR ligand binding and extracellular matrix organisation. This analysis shows that the Q4 genes may be linked to specific biological features of tumour aggressiveness that might explain their prognostic discriminatory pathways.

Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

Appendix A—Data showing particular combinations of biomarkers that have a prognostic value, as obtained using the forward and backward subsetting procedures of FIG. 4h.

Forward Analysis

| # genes | genes | cox_uva_p |
|---|---|---|
| 1 | ANLN | 0.041818455 |
| 1 | ASPM | 0.263058884 |
| 1 | CDCA4 | 0.163652217 |
| 1 | ERRFI1 | 0.177093247 |
| 1 | FURIN | 0.348998955 |
| 1 | GOLGA8A | 0.034540474 |
| 1 | ITGA6 | 0.084813068 |
| 1 | JAG1 | 0.205932533 |
| 1 | LRP12 | 0.683185595 |
| 1 | MAFF | 0.961062033 |
| 1 | MRPS17 | 0.858212313 |
| 1 | PLK1 | 0.042617432 |
| 1 | PNP | 0.121687458 |
| 1 | PPP1R13L | 0.968657519 |
| 1 | PRKCA | 0.702483557 |
| 1 | PTTG1 | 0.088427122 |
| 1 | PYGB | 0.517237935 |
| 1 | RPP25 | 0.232296771 |
| 1 | SCPEP1 | 0.104884518 |
| 1 | SLC46A3 | 0.405174216 |
| 1 | SNX7 | 0.115122189 |
| 1 | TPBG | 0.605770565 |
| 1 | XBP1 | 0.066390377 |
| 2 | GOLGA8A; ANLN | 0.012275494 |
| 2 | GOLGA8A; ASPM | 0.027556598 |
| 2 | GOLGA8A; CDCA4 | 0.030188165 |
| 2 | GOLGA8A; ERRFI1 | 0.015332111 |
| 2 | GOLGA8A; FURIN | 0.235362518 |
| 2 | GOLGA8A; ITGA6 | 0.99075881 |
| 2 | GOLGA8A; JAG1 | 0.016157845 |
| 2 | GOLGA8A; LRP12 | 0.057145738 |
| 2 | GOLGA8A; MAFF | 0.260293836 |
| 2 | GOLGA8A; MRPS17 | 0.539533791 |
| 2 | GOLGA8A; PLK1 | 0.006443672 |
| 2 | GOLGA8A; PNP | 0.020611578 |
| 2 | GOLGA8A; PPP1R13L | 0.224888126 |
| 2 | GOLGA8A; PRKCA | 0.088811222 |
| 2 | GOLGA8A; PTTG1 | 0.034670244 |
| 2 | GOLGA8A; PYGB | 0.265020258 |
| 2 | GOLGA8A; RPP25 | 0.028327058 |
| 2 | GOLGA8A; SCPEP1 | 0.029802609 |
| 2 | GOLGA8A; SLC46A3 | 0.034263244 |
| 2 | GOLGA8A; SNX7 | 0.03129588 |
| 2 | GOLGA8A; TPBG | 0.028335986 |
| 2 | GOLGA8A; XBP1 | 0.011472183 |
| 3 | GOLGA8A; PLK1; ANLN | 0.012045891 |
| 3 | GOLGA8A; PLK1; ASPM | 0.007699803 |
| 3 | GOLGA8A; PLK1; CDCA4 | 0.015432575 |
| 3 | GOLGA8A; PLK1; ERRFI1 | 0.004636685 |
| 3 | GOLGA8A; PLK1; FURIN | 0.15518042 |
| 3 | GOLGA8A; PLK1; ITGA6 | 0.275025589 |
| 3 | GOLGA8A; PLK1; JAG1 | 0.003158185 |
| 3 | GOLGA8A; PLK1; LRP12 | 0.012813514 |
| 3 | GOLGA8A; PLK1; MAFF | 0.048935457 |
| 3 | GOLGA8A; PLK1; MRPS17 | 0.217170811 |
| 3 | GOLGA8A; PLK1; PNP | 0.004784289 |
| 3 | GOLGA8A; PLK1; PPP1R13L | 0.049607072 |
| 3 | GOLGA8A; PLK1; PRKCA | 0.014158048 |
| 3 | GOLGA8A; PLK1; PTTG1 | 0.023815233 |
| 3 | GOLGA8A; PLK1; PYGB | 0.111936102 |
| 3 | GOLGA8A; PLK1; RPP25 | 0.00629167 |
| 3 | GOLGA8A; PLK1; SCPEP1 | 0.005822547 |
| 3 | GOLGA8A; PLK1; SLC46A3 | 0.008722335 |
| 3 | GOLGA8A; PLK1; SNX7 | 0.010349843 |
| 3 | GOLGA8A; PLK1; TPBG | 0.005846027 |
| 3 | GOLGA8A; PLK1; XBP1 | 0.001819835 |
| 4 | GOLGA8A; PLK1; XBP1; ANLN | 0.001067805 |
| 4 | GOLGA8A; PLK1; XBP1; ASPM | 0.00163718 |
| 4 | GOLGA8A; PLK1; XBP1; CDCA4 | 0.001375324 |
| 4 | GOLGA8A; PLK1; XBP1; ERRFI1 | 0.001429671 |
| 4 | GOLGA8A; PLK1; XBP1; FURIN | 0.038642914 |
| 4 | GOLGA8A; PLK1; XBP1; ITGA6 | 0.01217843 |
| 4 | GOLGA8A; PLK1; XBP1; JAG1 | 0.001428901 |
| 4 | GOLGA8A; PLK1; XBP1; LRP12 | 0.001945919 |
| 4 | GOLGA8A; PLK1; XBP1; MAFF | 0.002939452 |
| 4 | GOLGA8A; PLK1; XBP1; MRPS17 | 0.020350539 |

| # genes | genes | cox_uva_p |
|---|---|---|
| 4 | GOLGA8A; PLK1; XBP1; PNP | 0.001098998 |
| 4 | GOLGA8A; PLK1; XBP1; PPP1R13L | 0.008063382 |
| 4 | GOLGA8A; PLK1; XBP1; PRKCA | 0.003495628 |
| 4 | GOLGA8A; PLK1; XBP1; PTTG1 | 0.001624782 |
| 4 | GOLGA8A; PLK1; XBP1; PYGB | 0.01674869 |
| 4 | GOLGA8A; PLK1; XBP1; RPP25 | 0.001349407 |
| 4 | GOLGA8A; PLK1; XBP1; SCPEP1 | 0.00165571 |
| 4 | GOLGA8A; PLK1; XBP1; SLC46A3 | 0.001823592 |
| 4 | GOLGA8A; PLK1; XBP1; SNX7 | 0.002487021 |
| 4 | GOLGA8A; PLK1; XBP1; TPBG | 0.001871382 |
| 5 | GOLGA8A; PLK1; XBP1; ANLN; ASPM | 0.001151107 |
| 5 | GOLGA8A; PLK1; XBP1; ANLN; CDCA4 | 0.00133396 |
| 5 | GOLGA8A; PLK1; XBP1; ANLN; ERRFI1 | 0.001062368 |
| 5 | GOLGA8A; PLK1; XBP1; ANLN; FURIN | 0.010494351 |
| 5 | GOLGA8A; PLK1; XBP1; ANLN; ITGA6 | 0.004508898 |
| 5 | GOLGA8A; PLK1; XBP1; ANLN; JAG1 | 0.000873319 |
| 5 | GOLGA8A; PLK1; XBP1; ANLN; LRP12 | 0.001390939 |
| 5 | GOLGA8A; PLK1; XBP1; ANLN; MAFF | 0.001155984 |
| 5 | GOLGA8A; PLK1; XBP1; ANLN; MRPS17 | 0.007128406 |
| 5 | GOLGA8A; PLK1; XBP1; ANLN; PNP | 0.000800722 |
| 5 | GOLGA8A; PLK1; XBP1; ANLN; PPP1R13L | 0.002833564 |
| 5 | GOLGA8A; PLK1; XBP1; ANLN; PRKCA | 0.001687466 |
| 5 | GOLGA8A; PLK1; XBP1; ANLN; PTTG1 | 0.002319761 |
| 5 | GOLGA8A; PLK1; XBP1; ANLN; PYGB | 0.002659737 |
| 5 | GOLGA8A; PLK1; XBP1; ANLN; RPP25 | 0.000834291 |
| 5 | GOLGA8A; PLK1; XBP1; ANLN; SCPEP1 | 0.001005162 |
| 5 | GOLGA8A; PLK1; XBP1; ANLN; SLC46A3 | 0.00126263 |
| 5 | GOLGA8A; PLK1; XBP1; ANLN; SNX7 | 0.001365227 |
| 5 | GOLGA8A; PLK1; XBP1; ANLN; TPBG | 0.001200283 |
| 6 | GOLGA8A; PLK1; XBP1; ANLN; PNP; ASPM | 0.000871977 |
| 6 | GOLGA8A; PLK1; XBP1; ANLN; PNP; CDCA4 | 0.001045786 |
| 6 | GOLGA8A; PLK1; XBP1; ANLN; PNP; ERRFI1 | 0.000815129 |
| 6 | GOLGA8A; PLK1; XBP1; ANLN; PNP; FURIN | 0.009454011 |
| 6 | GOLGA8A; PLK1; XBP1; ANLN; PNP; ITGA6 | 0.003375094 |
| 6 | GOLGA8A; PLK1; XBP1; ANLN; PNP; JAG1 | 0.000649796 |
| 6 | GOLGA8A; PLK1; XBP1; ANLN; PNP; LRP12 | 0.001094424 |
| 6 | GOLGA8A; PLK1; XBP1; ANLN; PNP; MAFF | 0.000927384 |
| 6 | GOLGA8A; PLK1; XBP1; ANLN; PNP; MRPS17 | 0.005625551 |
| 6 | GOLGA8A; PLK1; XBP1; ANLN; PNP; PPP1R13L | 0.002099149 |
| 6 | GOLGA8A; PLK1; XBP1; ANLN; PNP; PRKCA | 0.001294491 |
| 6 | GOLGA8A; PLK1; XBP1; ANLN; PNP; PTTG1 | 0.001967547 |
| 6 | GOLGA8A; PLK1; XBP1; ANLN; PNP; PYGB | 0.002078703 |
| 6 | GOLGA8A; PLK1; XBP1; ANLN; PNP; RPP25 | 0.000637493 |
| 6 | GOLGA8A; PLK1; XBP1; ANLN; PNP; SCPEP1 | 0.000753103 |
| 6 | GOLGA8A; PLK1; XBP1; ANLN; PNP; SLC46A3 | 0.000940625 |
| 6 | GOLGA8A; PLK1; XBP1; ANLN; PNP; SNX7 | 0.00114478 |
| 6 | GOLGA8A; PLK1; XBP1; ANLN; PNP; TPBG | 0.000908059 |
| 7 | GOLGA8A; PLK1; XBP1; ANLN; PNP; RPP25; ASPM | 0.000696296 |
| 7 | GOLGA8A; PLK1; XBP1; ANLN; PNP; RPP25; CDCA4 | 0.00086646 |
| 7 | GOLGA8A; PLK1; XBP1; ANLN; PNP; RPP25; ERRFI1 | 0.000631494 |
| 7 | GOLGA8A; PLK1; XBP1; ANLN; PNP; RPP25; FURIN | 0.008803482 |
| 7 | GOLGA8A; PLK1; XBP1; ANLN; PNP; RPP25; ITGA6 | 0.002641657 |
| 7 | GOLGA8A; PLK1; XBP1; ANLN; PNP; RPP25; JAG1 | 0.000506688 |
| 7 | GOLGA8A; PLK1; XBP1; ANLN; PNP; RPP25; LRP12 | 0.000886742 |
| 7 | GOLGA8A; PLK1; XBP1; ANLN; PNP; RPP25; MAFF | 0.000733813 |
| 7 | GOLGA8A; PLK1; XBP1; ANLN; PNP; RPP25; MRPS17 | 0.004866355 |
| 7 | GOLGA8A; PLK1; XBP1; ANLN; PNP; RPP25; PPP1R13L | 0.001691473 |
| 7 | GOLGA8A; PLK1; XBP1; ANLN; PNP; RPP25; PRKCA | 0.000928416 |
| 7 | GOLGA8A; PLK1; XBP1; ANLN; PNP; RPP25; PTTG1 | 0.001656462 |
| 7 | GOLGA8A; PLK1; XBP1; ANLN; PNP; RPP25; PYGB | 0.001912721 |
| 7 | GOLGA8A; PLK1; XBP1; ANLN; PNP; RPP25; SCPEP1 | 0.000600101 |
| 7 | GOLGA8A; PLK1; XBP1; ANLN; PNP; RPP25; SLC46A3 | 0.000759857 |
| 7 | GOLGA8A; PLK1; XBP1; ANLN; PNP; RPP25; SNX7 | 0.000956246 |
| 7 | GOLGA8A; PLK1; XBP1; ANLN; PNP; RPP25; TPBG | 0.000721601 |
| 8 | GOLGA8A; PLK1; XBP1; ANLN; PNP; RPP25; JAG1; ASPM | 0.000555802 |
| 8 | GOLGA8A; PLK1; XBP1; ANLN; PNP; RPP25; JAG1; CDCA4 | 0.000692848 |
| 8 | GOLGA8A; PLK1; XBP1; ANLN; PNP; RPP25; JAG1; ERRFI1 | 0.000508326 |
| 8 | GOLGA8A; PLK1; XBP1; ANLN; PNP; RPP25; JAG1; FURIN | 0.007833882 |
| 8 | GOLGA8A; PLK1; XBP1; ANLN; PNP; RPP25; JAG1; ITGA6 | 0.00213277 |
| 8 | GOLGA8A; PLK1; XBP1; ANLN; PNP; RPP25; JAG1; LRP12 | 0.000741326 |
| 8 | GOLGA8A; PLK1; XBP1; ANLN; PNP; RPP25; JAG1; MAFF | 0.000616331 |
| 8 | GOLGA8A; PLK1; XBP1; ANLN; PNP; RPP25; JAG1; MRPS17 | 0.003874023 |
| 8 | GOLGA8A; PLK1; XBP1; ANLN; PNP; RPP25; JAG1; PPP1R13L | 0.001387564 |
| 8 | GOLGA8A; PLK1; XBP1; ANLN; PNP; RPP25; JAG1; PRKCA | 0.000774936 |
| 8 | GOLGA8A; PLK1; XBP1; ANLN; PNP; RPP25; JAG1; PTTG1 | 0.001390476 |
| 8 | GOLGA8A; PLK1; XBP1; ANLN; PNP; RPP25; JAG1; PYGB | 0.001591054 |

| # genes | genes | cox_uva_p |
|---|---|---|
| 8 | GOLGA8A; PLK1; XBP1; ANLN; PNP; RPP25; JAG1; SCPEP1 | 0.000476355 |
| 8 | GOLGA8A; PLK1; XBP1; ANLN; PNP; RPP25; JAG1; SLC46A3 | 0.000606713 |
| 8 | GOLGA8A; PLK1; XBP1; ANLN; PNP; RPP25; JAG1; SNX7 | 0.000791577 |
| 8 | GOLGA8A; PLK1; XBP1; ANLN; PNP; RPP25; JAG1; TPBG | 0.000585591 |
| 9 | GOLGA8A; PLK1; XBP1; ANLN; PNP; RPP25; JAG1; SCPEP1; ASPM | 0.000523602 |
| 9 | GOLGA8A; PLK1; XBP1; ANLN; PNP; RPP25; JAG1; SCPEP1; CDCA4 | 0.000659565 |
| 9 | GOLGA8A; PLK1; XBP1; ANLN; PNP; RPP25; JAG1; SCPEP1; ERRFI1 | 0.000479525 |
| 9 | GOLGA8A; PLK1; XBP1; ANLN; PNP; RPP25; JAG1; SCPEP1; FURIN | 0.007746134 |
| 9 | GOLGA8A; PLK1; XBP1; ANLN; PNP; RPP25; JAG1; SCPEP1; ITGA6 | 0.002017874 |
| 9 | GOLGA8A; PLK1; XBP1; ANLN; PNP; RPP25; JAG1; SCPEP1; LRP12 | 0.000702243 |
| 9 | GOLGA8A; PLK1; XBP1; ANLN; PNP; RPP25; JAG1; SCPEP1; MAFF | 0.000585322 |
| 9 | GOLGA8A; PLK1; XBP1; ANLN; PNP; RPP25; JAG1; SCPEP1; MRPS17 | 0.003723678 |
| 9 | GOLGA8A; PLK1; XBP1; ANLN; PNP; RPP25; JAG1; SCPEP1; PPP1R13L | 0.001319606 |
| 9 | GOLGA8A; PLK1; XBP1; ANLN; PNP; RPP25; JAG1; SCPEP1; PRKCA | 0.000728205 |
| 9 | GOLGA8A; PLK1; XBP1; ANLN; PNP; RPP25; JAG1; SCPEP1; PTTG1 | 0.00134489 |
| 9 | GOLGA8A; PLK1; XBP1; ANLN; PNP; RPP25; JAG1; SCPEP1; PYGB | 0.00154244 |
| 9 | GOLGA8A; PLK1; XBP1; ANLN; PNP; RPP25; JAG1; SCPEP1; SLC46A3 | 0.000573298 |
| 9 | GOLGA8A; PLK1; XBP1; ANLN; PNP; RPP25; JAG1; SCPEP1; SNX7 | 0.000753306 |
| 9 | GOLGA8A; PLK1; XBP1; ANLN; PNP; RPP25; JAG1; SCPEP1; TPBG | 0.00055091 |
| 10 | GOLGA8A; PLK1; XBP1; ANLN; PNP; RPP25; JAG1; SCPEP1; ERRFI1; ASPM | 0.000525483 |
| 10 | GOLGA8A; PLK1; XBP1; ANLN; PNP; RPP25; JAG1; SCPEP1; ERRFI1; CDCA4 | 0.000644867 |
| 10 | GOLGA8A; PLK1; XBP1; ANLN; PNP; RPP25; JAG1; SCPEP1; ERRFI1; FURIN | 0.006579792 |
| 10 | GOLGA8A; PLK1; XBP1; ANLN; PNP; RPP25; JAG1; SCPEP1; ERRFI1; ITGA6 | 0.001848955 |
| 10 | GOLGA8A; PLK1; XBP1; ANLN; PNP; RPP25; JAG1; SCPEP1; ERRFI1; LRP12 | 0.000682897 |
| 10 | GOLGA8A; PLK1; XBP1; ANLN; PNP; RPP25; JAG1; SCPEP1; ERRFI1; MAFF | 0.000636855 |
| 10 | GOLGA8A; PLK1; XBP1; ANLN; PNP; RPP25; JAG1; SCPEP1; ERRFI1; MRPS17 | 0.003158618 |
| 10 | GOLGA8A; PLK1; XBP1; ANLN; PNP; RPP25; JAG1; SCPEP1; ERRFI1; PPP1R13L | 0.001244988 |
| 10 | GOLGA8A; PLK1; XBP1; ANLN; PNP; RPP25; JAG1; SCPEP1; ERRFI1; PRKCA | 0.000779841 |
| 10 | GOLGA8A; PLK1; XBP1; ANLN; PNP; RPP25; JAG1; SCPEP1; ERRFI1; PTTG1 | 0.001274829 |
| 10 | GOLGA8A; PLK1; XBP1; ANLN; PNP; RPP25; JAG1; SCPEP1; ERRFI1; PYGB | 0.001158669 |
| 10 | GOLGA8A; PLK1; XBP1; ANLN; PNP; RPP25; JAG1; SCPEP1; ERRFI1; SLC46A3 | 0.00058145 |
| 10 | GOLGA8A; PLK1; XBP1; ANLN; PNP; RPP25; JAG1; SCPEP1; ERRFI1; SNX7 | 0.000758055 |
| 10 | GOLGA8A; PLK1; XBP1; ANLN; PNP; RPP25; JAG1; SCPEP1; ERRFI1; TPBG | 0.000557529 |
| 11 | GOLGA8A; PLK1; XBP1; ANLN; PNP; RPP25; JAG1; SCPEP1; ERRFI1; ASPM; CDCA4 | 0.000703539 |
| 11 | GOLGA8A; PLK1; XBP1; ANLN; PNP; RPP25; JAG1; SCPEP1; ERRFI1; ASPM; FURIN | 0.006399642 |
| 11 | GOLGA8A; PLK1; XBP1; ANLN; PNP; RPP25; JAG1; SCPEP1; ERRFI1; ASPM; ITGA6 | 0.001965204 |
| 11 | GOLGA8A; PLK1; XBP1; ANLN; PNP; RPP25; JAG1; SCPEP1; ERRFI1; ASPM; LRP12 | 0.000744638 |
| 11 | GOLGA8A; PLK1; XBP1; ANLN; PNP; RPP25; JAG1; SCPEP1; ERRFI1; ASPM; MAFF | 0.000680295 |
| 11 | GOLGA8A; PLK1; XBP1; ANLN; PNP; RPP25; JAG1; SCPEP1; ERRFI1; ASPM; MRPS17 | 0.003264589 |
| 11 | GOLGA8A; PLK1; XBP1; ANLN; PNP; RPP25; JAG1; SCPEP1; ERRFI1; ASPM; PPP1R13L | 0.001300682 |
| 11 | GOLGA8A; PLK1; XBP1; ANLN; PNP; RPP25; JAG1; SCPEP1; ERRFI1; ASPM; PRKCA | 0.00083915 |
| 11 | GOLGA8A; PLK1; XBP1; ANLN; PNP; RPP25; JAG1; SCPEP1; ERRFI1; ASPM; PTTG1 | 0.001379242 |
| 11 | GOLGA8A; PLK1; XBP1; ANLN; PNP; RPP25; JAG1; SCPEP1; ERRFI1; ASPM; PYGB | 0.001112283 |
| 11 | GOLGA8A; PLK1; XBP1; ANLN; PNP; RPP25; JAG1; SCPEP1; ERRFI1; ASPM; SLC46A3 | 0.000632537 |
| 11 | GOLGA8A; PLK1; XBP1; ANLN; PNP; RPP25; JAG1; SCPEP1; ERRFI1; ASPM; SNX7 | 0.000791258 |
| 11 | GOLGA8A; PLK1; XBP1; ANLN; PNP; RPP25; JAG1; SCPEP1; ERRFI1; ASPM; TPBG | 0.000606543 |
| 12 | GOLGA8A; PLK1; XBP1; ANLN; PNP; RPP25; JAG1; SCPEP1; ERRFI1; ASPM; TPBG; CDCA4 | 0.000778418 |
| 12 | GOLGA8A; PLK1; XBP1; ANLN; PNP; RPP25; JAG1; SCPEP1; ERRFI1; ASPM; TPBG; FURIN | 0.005593133 |
| 12 | GOLGA8A; PLK1; XBP1; ANLN; PNP; RPP25; JAG1; SCPEP1; ERRFI1; ASPM; TPBG; ITGA6 | 0.002136194 |
| 12 | GOLGA8A; PLK1; XBP1; ANLN; PNP; RPP25; JAG1; SCPEP1; ERRFI1; ASPM; TPBG; LRP12 | 0.000851595 |
| 12 | GOLGA8A; PLK1; XBP1; ANLN; PNP; RPP25; JAG1; SCPEP1; ERRFI1; ASPM; TPBG; MAFF | 0.000731375 |
| 12 | GOLGA8A; PLK1; XBP1; ANLN; PNP; RPP25; JAG1; SCPEP1; ERRFI1; ASPM; TPBG; MRPS17 | 0.003255138 |
| 12 | GOLGA8A; PLK1; XBP1; ANLN; PNP; RPP25; JAG1; SCPEP1; ERRFI1; ASPM; TPBG; PPP1R13L | 0.00152152 |
| 12 | GOLGA8A; PLK1; XBP1; ANLN; PNP; RPP25; JAG1; SCPEP1; ERRFI1; ASPM; TPBG; PRKCA | 0.000913282 |
| 12 | GOLGA8A; PLK1; XBP1; ANLN; PNP; RPP25; JAG1; SCPEP1; ERRFI1; ASPM; TPBG; PTTG1 | 0.001473473 |
| 12 | GOLGA8A; PLK1; XBP1; ANLN; PNP; RPP25; JAG1; SCPEP1; ERRFI1; ASPM; TPBG; PYGB | 0.000959376 |
| 12 | GOLGA8A; PLK1; XBP1; ANLN; PNP; RPP25; JAG1; SCPEP1; ERRFI1; ASPM; TPBG; SLC46A3 | 0.000710603 |
| 12 | GOLGA8A; PLK1; XBP1; ANLN; PNP; RPP25; JAG1; SCPEP1; ERRFI1; ASPM; TPBG; SNX7 | 0.000899224 |
| 13 | GOLGA8A; PLK1; XBP1; ANLN; PNP; RPP25; JAG1; SCPEP1; ERRFI1; ASPM; TPBG; SLC46A3; CDCA4 | 0.000919638 |
| 13 | GOLGA8A; PLK1; XBP1; ANLN; PNP; RPP25; JAG1; SCPEP1; ERRFI1; ASPM; TPBG; SLC46A3; FURIN | 0.005172175 |
| 13 | GOLGA8A; PLK1; XBP1; ANLN; PNP; RPP25; JAG1; SCPEP1; ERRFI1; ASPM; TPBG; SLC46A3; ITGA6 | 0.00234948 |

| # genes | genes | cox_uva_p |
|---|---|---|
| 13 | GOLGA8A; PLK1; XBP1; ANLN; PNP; RPP25; JAG1; SCPEP1; ERRFI1; ASPM; TPBG; SLC46A3; LRP12 | 0.000884973 |
| 13 | GOLGA8A; PLK1; XBP1; ANLN; PNP; RPP25; JAG1; SCPEP1; ERRFI1; ASPM; TPBG; SLC46A3; MAFF | 0.00076908 |
| 13 | GOLGA8A; PLK1; XBP1; ANLN; PNP; RPP25; JAG1; SCPEP1; ERRFI1; ASPM; TPBG; SLC46A3; MRPS17 | 0.003853782 |
| 13 | GOLGA8A; PLK1; XBP1; ANLN; PNP; RPP25; JAG1; SCPEP1; ERRFI1; ASPM; TPBG; SLC46A3; PPP1R13L | 0.001790409 |
| 13 | GOLGA8A; PLK1; XBP1; ANLN; PNP; RPP25; JAG1; SCPEP1; ERRFI1; ASPM; TPBG; SLC46A3; PRKCA | 0.00107647 |
| 13 | GOLGA8A; PLK1; XBP1; ANLN; PNP; RPP25; JAG1; SCPEP1; ERRFI1; ASPM; TPBG; SLC46A3; PTTG1 | 0.001510399 |
| 13 | GOLGA8A; PLK1; XBP1; ANLN; PNP; RPP25; JAG1; SCPEP1; ERRFI1; ASPM; TPBG; SLC46A3; PYGB | 0.001044021 |
| 13 | GOLGA8A; PLK1; XBP1; ANLN; PNP; RPP25; JAG1; SCPEP1; ERRFI1; ASPM; TPBG; SLC46A3; SNX7 | 0.000905041 |
| 14 | GOLGA8A; PLK1; XBP1; ANLN; PNP; RPP25; JAG1; SCPEP1; ERRFI1; ASPM; TPBG; SLC46A3; MAFF; CDCA4 | 0.000978697 |
| 14 | GOLGA8A; PLK1; XBP1; ANLN; PNP; RPP25; JAG1; SCPEP1; ERRFI1; ASPM; TPBG; SLC46A3; MAFF; FURIN | 0.007155365 |
| 14 | GOLGA8A; PLK1; XBP1; ANLN; PNP; RPP25; JAG1; SCPEP1; ERRFI1; ASPM; TPBG; SLC46A3; MAFF; ITGA6 | 0.00261825 |
| 14 | GOLGA8A; PLK1; XBP1; ANLN; PNP; RPP25; JAG1; SCPEP1; ERRFI1; ASPM; TPBG; SLC46A3; MAFF; LRP12 | 0.001006003 |
| 14 | GOLGA8A; PLK1; XBP1; ANLN; PNP; RPP25; JAG1; SCPEP1; ERRFI1; ASPM; TPBG; SLC46A3; MAFF; MRPS17 | 0.002903731 |
| 14 | GOLGA8A; PLK1; XBP1; ANLN; PNP; RPP25; JAG1; SCPEP1; ERRFI1; ASPM; TPBG; SLC46A3; MAFF; PPP1R13L | 0.001509429 |
| 14 | GOLGA8A; PLK1; XBP1; ANLN; PNP; RPP25; JAG1; SCPEP1; ERRFI1; ASPM; TPBG; SLC46A3; MAFF; PRKCA | 0.001290283 |
| 14 | GOLGA8A; PLK1; XBP1; ANLN; PNP; RPP25; JAG1; SCPEP1; ERRFI1; ASPM; TPBG; SLC46A3; MAFF; PTTG1 | 0.001413577 |
| 14 | GOLGA8A; PLK1; XBP1; ANLN; PNP; RPP25; JAG1; SCPEP1; ERRFI1; ASPM; TPBG; SLC46A3; MAFF; PYGB | 0.001446697 |
| 14 | GOLGA8A; PLK1; XBP1; ANLN; PNP; RPP25; JAG1; SCPEP1; ERRFI1; ASPM; TPBG; SLC46A3; MAFF; SNX7 | 0.000934429 |
| 15 | GOLGA8A; PLK1; XBP1; ANLN; PNP; RPP25; JAG1; SCPEP1; ERRFI1; ASPM; TPBG; SLC46A3; MAFF; SNX7; CDCA4 | 0.000847867 |
| 15 | GOLGA8A; PLK1; XBP1; ANLN; PNP; RPP25; JAG1; SCPEP1; ERRFI1; ASPM; TPBG; SLC46A3; MAFF; SNX7; FURIN | 0.001988329 |
| 15 | GOLGA8A; PLK1; XBP1; ANLN; PNP; RPP25; JAG1; SCPEP1; ERRFI1; ASPM; TPBG; SLC46A3; MAFF; SNX7; ITGA6 | 0.002820134 |
| 15 | GOLGA8A; PLK1; XBP1; ANLN; PNP; RPP25; JAG1; SCPEP1; ERRFI1; ASPM; TPBG; SLC46A3; MAFF; SNX7; LRP12 | 0.00114868 |
| 15 | GOLGA8A; PLK1; XBP1; ANLN; PNP; RPP25; JAG1; SCPEP1; ERRFI1; ASPM; TPBG; SLC46A3; MAFF; SNX7; MRPS17 | 0.002273779 |
| 15 | GOLGA8A; PLK1; XBP1; ANLN; PNP; RPP25; JAG1; SCPEP1; ERRFI1; ASPM; TPBG; SLC46A3; MAFF; SNX7; PPP1R13L | 0.001110718 |
| 15 | GOLGA8A; PLK1; XBP1; ANLN; PNP; RPP25; JAG1; SCPEP1; ERRFI1; ASPM; TPBG; SLC46A3; MAFF; SNX7; PRKCA | 0.001384835 |
| 15 | GOLGA8A; PLK1; XBP1; ANLN; PNP; RPP25; JAG1; SCPEP1; ERRFI1; ASPM; TPBG; SLC46A3; MAFF; SNX7; PTTG1 | 0.001356447 |
| 15 | GOLGA8A; PLK1; XBP1; ANLN; PNP; RPP25; JAG1; SCPEP1; ERRFI1; ASPM; TPBG; SLC46A3; MAFF; SNX7; PYGB | 0.000737892 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; CDCA4 | 0.000708894 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; FURIN | 0.004567885 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; ITGA6 | 0.00216458 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; LRP12 | 0.000758464 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; MRPS17 | 0.001543282 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; PPP1R13L | 0.000848371 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; PRKCA | 0.000956596 |
| 16 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1 | 0.000618833 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; CDCA4 | 0.000659882 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; FURIN | 0.002239651 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; ITGA6 | 0.001534245 |

| # genes | genes | cox_uva_p |
|---|---|---|
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; LRP12 | 0.000661161 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; MRPS17 | 0.001327286 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L | 0.000626561 |
| 17 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PRKCA | 0.000721668 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; CDCA4 | 0.000686023 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; FURIN | 0.002264136 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; ITGA6 | 0.001467503 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12 | 0.000636362 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; MRPS17 | 0.001281134 |
| 18 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; PRKCA | 0.000682987 |
| 19 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; CDCA4 | 0.000701266 |
| 19 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; FURIN | 0.002249549 |
| 19 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; ITGA6 | 0.00148685 |
| 19 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; MRPS17 | 0.001234511 |
| 19 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA | 0.000683265 |
| 20 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4 | 0.000719478 |
| 20 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; FURIN | 0.001950733 |
| 20 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; ITGA6 | 0.001574417 |
| 20 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; MRPS17 | 0.00123664 |
| 21 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; FURIN | 0.002118878 |
| 21 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; ITGA6 | 0.00157084 |
| 21 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; MRPS17 | 0.001279942 |
| 22 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; MRPS17; FURIN | 0.003246655 |
| 22 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; MRPS17; ITGA6 | 0.00262722 |
| 23 | GOLGA8A; PLK1; XBP1; ANLN; PNP; RPP25; JAG1; SCPEP1; ERRFI1; ASPM; TPBG; SLC46A3; MAFF; SNX7; PYGB; PTTG1; PPP1R13L; LRP12; PRKCA; CDCA4; MRPS17; ITGA6; FURIN | 0.004740789 |

50

Backward Analysis

| # genes | genes | cox_uva_p |
|---|---|---|
| 23 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.004741 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG | 0.015958 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; XBP1 | 0.005193 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; TPBG; XBP1 | 0.012021 |

| # genes | genes | cox_uva_p |
|---|---|---|
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SNX7; TPBG; XBP1 | 0.00489 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SLC46A3; SNX7; TPBG; XBP1 | 0.004777 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; SCPEP1; SLC46A3; SNX7; TPBG; XBP1 | 0.004931 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PTTG1; RPP25; SCPEP1; SLC46A3; SNX7; TPBG; XBP1 | 0.003411 |
| 22 | ANLN; ASPM; CDCA4; ERRFI1; FURIN; GOLGA8A; ITGA6; JAG1; LRP12; MAFF; MRPS17; PLK1; PNP; PPP1R13L; PRKCA; PYGB; RPP25; SCPEP1; SLC46A3; SNX7; TPBG; XBP1 | 0.008673 |
| 22 | ANLN; ASPM; CDCA4; ERRFI1; FURIN; GOLGA8A; ITGA6; JAG1; LRP12; MAFF; MRPS17; PLK1; PNP; PPP1R13L; PTTG1; PYGB; RPP25; SCPEP1; SLC46A3; SNX7; TPBG; XBP1 | 0.005497 |
| 22 | ANLN; ASPM; CDCA4; ERRFI1; FURIN; GOLGA8A; ITGA6; JAG1; LRP12; MAFF; MRPS17; PLK1; PNP; PRKCA; PTTG1; PYGB; RPP25; SCPEP1; SLC46A3; SNX7; TPBG; XBP1 | 0.00495 |
| 22 | ANLN; ASPM; CDCA4; ERRFI1; FURIN; GOLGA8A; ITGA6; JAG1; LRP12; MAFF; MRPS17; PLK1; PPP1R13L; PRKCA; PTTG1; PYGB; RPP25; SCPEP1; SLC46A3; SNX7; TPBG; XBP1 | 0.005074 |
| 22 | ANLN; ASPM; CDCA4; ERRFI1; FURIN; GOLGA8A; ITGA6; JAG1; LRP12; MAFF; MRPS17; PNP; PPP1R13L; PRKCA; PTTG1; PYGB; RPP25; SCPEP1; SLC46A3; SNX7; TPBG; XBP1 | 0.005619 |
| 22 | ANLN; ASPM; CDCA4; ERRFI1; FURIN; GOLGA8A; ITGA6; JAG1; LRP12; MAFF; PLK1; PNP; PPP1R13L; PRKCA; PTTG1; PYGB; RPP25; SCPEP1; SLC46A3; SNX7; TPBG; XBP1 | 0.003191 |
| 22 | ANLN; ASPM; CDCA4; ERRFI1; FURIN; GOLGA8A; ITGA6; JAG1; LRP12; MRPS17; PLK1; PNP; PPP1R13L; PRKCA; PTTG1; PYGB; RPP25; SCPEP1; SLC46A3; SNX7; TPBG; XBP1 | 0.004142 |
| 22 | ANLN; ASPM; CDCA4; ERRFI1; FURIN; GOLGA8A; ITGA6; JAG1; MAFF; MRPS17; PLK1; PNP; PPP1R13L; PRKCA; PTTG1; PYGB; RPP25; SCPEP1; SLC46A3; SNX7; TPBG; XBP1 | 0.004903 |
| 22 | ANLN; ASPM; CDCA4; ERRFI1; FURIN; GOLGA8A; ITGA6; LRP12; MAFF; MRPS17; PLK1; PNP; PPP1R13L; PRKCA; PTTG1; PYGB; RPP25; SCPEP1; SLC46A3; SNX7; TPBG; XBP1 | 0.005157 |
| 22 | ANLN; ASPM; CDCA4; ERRFI1; FURIN; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.003247 |
| 22 | ANLN; ASPM; CDCA4; ERRFI1; FURIN; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.006409 |
| 22 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.002627 |
| 22 | ANLN; ASPM; CDCA4; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.005244 |
| 22 | ANLN; ASPM; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.004571 |
| 22 | ANLN; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.004797 |
| 22 | ASPM; CDCA4; ERRFI1; FURIN; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.008463 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG | 0.011783 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; XBP1 | 0.002741 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; TPBG; XBP1 | 0.004937 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SNX7; TPBG; XBP1 | 0.002537 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SLC46A3; SNX7; TPBG; XBP1 | 0.002675 |

| # genes | genes | cox_uva_p |
|---|---|---|
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; PYGB; SCPEP1; SLC46A3; SNX7; TPBG; XBP1 | 0.002878 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PTTG1; RPP25; SCPEP1; SLC46A3; SNX7; TPBG; XBP1 | 0.005503 |
| 21 | ANLN; ASPM; CDCA4; ERRFI1; GOLGA8A; ITGA6; JAG1; LRP12; MAFF; MRPS17; PLK1; PNP; PPP1R13L; PRKCA; PYGB; RPP25; SCPEP1; SLC46A3; SNX7; TPBG; XBP1 | 0.003434 |
| 21 | ANLN; ASPM; CDCA4; ERRFI1; GOLGA8A; ITGA6; JAG1; LRP12; MAFF; MRPS17; PLK1; PNP; PPP1R13L; PTTG1; PYGB; RPP25; SCPEP1; SLC46A3; SNX7; TPBG; XBP1 | 0.0027 |
| 21 | ANLN; ASPM; CDCA4; ERRFI1; GOLGA8A; ITGA6; JAG1; LRP12; MAFF; MRPS17; PLK1; PNP; PRKCA; PTTG1; PYGB; RPP25; SCPEP1; SLC46A3; SNX7; TPBG; XBP1 | 0.002961 |
| 21 | ANLN; ASPM; CDCA4; ERRFI1; GOLGA8A; ITGA6; JAG1; LRP12; MAFF; MRPS17; PLK1; PPP1R13L; PRKCA; PTTG1; PYGB; RPP25; SCPEP1; SLC46A3; SNX7; TPBG; XBP1 | 0.002937 |
| 21 | ANLN; ASPM; CDCA4; ERRFI1; GOLGA8A; ITGA6; JAG1; LRP12; MAFF; MRPS17; PNP; PPP1R13L; PRKCA; PTTG1; PYGB; RPP25; SCPEP1; SLC46A3; SNX7; TPBG; XBP1 | 0.003049 |
| 21 | ANLN; ASPM; CDCA4; ERRFI1; GOLGA8A; ITGA6; JAG1; LRP12; MAFF; PLK1; PNP; PPP1R13L; PRKCA; PTTG1; PYGB; RPP25; SCPEP1; SLC46A3; SNX7; TPBG; XBP1 | 0.001571 |
| 21 | ANLN; ASPM; CDCA4; ERRFI1; GOLGA8A; ITGA6; JAG1; LRP12; MRPS17; PLK1; PNP; PPP1R13L; PRKCA; PTTG1; PYGB; RPP25; SCPEP1; SLC46A3; SNX7; TPBG; XBP1 | 0.002735 |
| 21 | ANLN; ASPM; CDCA4; ERRFI1; GOLGA8A; ITGA6; JAG1; MAFF; MRPS17; PLK1; PNP; PPP1R13L; PRKCA; PTTG1; PYGB; RPP25; SCPEP1; SLC46A3; SNX7; TPBG; XBP1 | 0.002717 |
| 21 | ANLN; ASPM; CDCA4; ERRFI1; GOLGA8A; ITGA6; LRP12; MAFF; MRPS17; PLK1; PNP; PPP1R13L; PRKCA; PTTG1; PYGB; RPP25; SCPEP1; SLC46A3; SNX7; TPBG; XBP1 | 0.002943 |
| 21 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.00128 |
| 21 | ANLN; ASPM; CDCA4; ERRFI1; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.00396 |
| 21 | ANLN; ASPM; CDCA4; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.002857 |
| 21 | ANLN; ASPM; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.002668 |
| 21 | ANLN; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.002598 |
| 21 | ASPM; CDCA4; ERRFI1; GOLGA8A; ITGA6; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.003095 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG | 0.005707 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; XBP1 | 0.001329 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; TPBG; XBP1 | 0.002493 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SNX7; TPBG; XBP1 | 0.00121 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; RPP25; SLC46A3; SNX7; TPBG; XBP1 | 0.001305 |
| 20 | ANLN; ASPM; CDCA4; ERRFI1; GOLGA8A; JAG1; LRP12; MAFF; MRPS17; PLK1; PNP; PPP1R13L; PRKCA; PTTG1; PYGB; SCPEP1; SLC46A3; SNX7; TPBG; XBP1 | 0.001394 |
| 20 | ANLN; ASPM; CDCA4; ERRFI1; GOLGA8A; JAG1; LRP12; MAFF; MRPS17; PLK1; PNP; PPP1R13L; PRKCA; PTTG1; RPP25; SCPEP1; SLC46A3; SNX7; TPBG; XBP1 | 0.002858 |
| 20 | ANLN; ASPM; CDCA4; ERRFI1; GOLGA8A; JAG1; LRP12; MAFF; MRPS17; PLK1; PNP; PPP1R13L; PRKCA; PYGB; RPP25; SCPEP1; SLC46A3; SNX7; TPBG; XBP1 | 0.001475 |
| 20 | ANLN; ASPM; CDCA4; ERRFI1; GOLGA8A; JAG1; LRP12; MAFF; MRPS17; PLK1; PNP; PPP1R13L; PTTG1; PYGB; RPP25; SCPEP1; SLC46A3; SNX7; TPBG; XBP1 | 0.001318 |
| 20 | ANLN; ASPM; CDCA4; ERRFI1; GOLGA8A; JAG1; LRP12; MAFF; MRPS17; PLK1; PNP; PRKCA; PTTG1; PYGB; RPP25; SCPEP1; SLC46A3; SNX7; TPBG; XBP1 | 0.001407 |
| 20 | ANLN; ASPM; CDCA4; ERRFI1; GOLGA8A; JAG1; LRP12; MAFF; MRPS17; PLK1; PPP1R13L; PRKCA; PTTG1; PYGB; RPP25; SCPEP1; SLC46A3; SNX7; TPBG; XBP1 | 0.001429 |
| 20 | ANLN; ASPM; CDCA4; ERRFI1; GOLGA8A; JAG1; LRP12; MAFF; MRPS17; PNP; PPP1R13L; PRKCA; PTTG1; PYGB; RPP25; SCPEP1; SLC46A3; SNX7; TPBG; XBP1 | 0.001396 |

| # genes | genes | cox_uva_p |
|---|---|---|
| 20 | ANLN; ASPM; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; SNX7; TPBG; XBP1 | 0.000719 |
| 20 | ANLN; ASPM; CDCA4; ERRFI1; GOLGA8A; JAG1; LRP12; MRPS17; PLK1; PNP; PPP1R13L; PRKCA; PTTG1; PYGB; RPP25; SCPEP1; SLC46A3; SNX7; TPBG; XBP1 | 0.001357 |
| 20 | ANLN; ASPM; CDCA4; ERRFI1; GOLGA8A; JAG1; MAFF; MRPS17; PLK1; PNP; PPP1R13L; PRKCA; PTTG1; PYGB; RPP25; SCPEP1; SLC46A3; SNX7; TPBG; XBP1 | 0.001325 |
| 20 | ANLN; ASPM; CDCA4; ERRFI1; GOLGA8A; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001447 |
| 20 | ANLN; ASPM; CDCA4; ERRFI1; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001943 |
| 20 | ANLN; ASPM; CDCA4; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001373 |
| 20 | ANLN; ASPM; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001237 |
| 20 | ANLN; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001257 |
| 20 | ASPM; CDCA4; ERRFI1; GOLGA8A; JAG1; LRP12; MAFF; MRPS17; PLK1; PNP; PPP1R13L; PRKCA; PTTG1; PYGB; RPP25; SCPEP1; SLC46A3; SNX7; TPBG; XBP1 | 0.001325 |
| 19 | ANLN; ASPM; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; SNX7; TPBG | 0.003291 |
| 19 | ANLN; ASPM; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; SNX7; XBP1 | 0.000726 |
| 19 | ANLN; ASPM; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; TPBG; XBP1 | 0.001281 |
| 19 | ANLN; ASPM; CDCA4; ERRFI1; GOLGA8A; JAG1; LRP12; MAFF; PLK1; PNP; PPP1R13L; PRKCA; PTTG1; PYGB; RPP25; SCPEP1; SNX7; TPBG; XBP1 | 0.000708 |
| 19 | ANLN; ASPM; CDCA4; ERRFI1; GOLGA8A; JAG1; LRP12; MAFF; PLK1; PNP; PPP1R13L; PRKCA; PTTG1; PYGB; RPP25; SLC46A3; SNX7; TPBG; XBP1 | 0.000735 |
| 19 | ANLN; ASPM; CDCA4; ERRFI1; GOLGA8A; JAG1; LRP12; MAFF; PLK1; PNP; PPP1R13L; PRKCA; PTTG1; PYGB; SCPEP1; SLC46A3; SNX7; TPBG; XBP1 | 0.000799 |
| 19 | ANLN; ASPM; CDCA4; ERRFI1; GOLGA8A; JAG1; LRP12; MAFF; PLK1; PNP; PPP1R13L; PRKCA; PTTG1; RPP25; SCPEP1; SLC46A3; SNX7; TPBG; XBP1 | 0.001652 |
| 19 | ANLN; ASPM; CDCA4; ERRFI1; GOLGA8A; JAG1; LRP12; MAFF; PLK1; PNP; PPP1R13L; PRKCA; PYGB; RPP25; SCPEP1; SLC46A3; SNX7; TPBG; XBP1 | 0.000886 |
| 19 | ANLN; ASPM; CDCA4; ERRFI1; GOLGA8A; JAG1; LRP12; MAFF; PLK1; PNP; PPP1R13L; PTTG1; PYGB; RPP25; SCPEP1; SLC46A3; SNX7; TPBG; XBP1 | 0.000701 |
| 19 | ANLN; ASPM; CDCA4; ERRFI1; GOLGA8A; JAG1; LRP12; MAFF; PLK1; PNP; PRKCA; PTTG1; PYGB; RPP25; SCPEP1; SLC46A3; SNX7; TPBG; XBP1 | 0.00077 |
| 19 | ANLN; ASPM; CDCA4; ERRFI1; GOLGA8A; JAG1; LRP12; MAFF; PLK1; PPP1R13L; PRKCA; PTTG1; PYGB; RPP25; SCPEP1; SLC46A3; SNX7; TPBG; XBP1 | 0.000802 |
| 19 | ANLN; ASPM; CDCA4; ERRFI1; GOLGA8A; JAG1; LRP12; MAFF; PNP; PPP1R13L; PRKCA; PTTG1; PYGB; RPP25; SCPEP1; SLC46A3; SNX7; TPBG; XBP1 | 0.000772 |
| 19 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000646 |
| 19 | ANLN; ASPM; CDCA4; ERRFI1; GOLGA8A; JAG1; MAFF; PLK1; PNP; PPP1R13L; PRKCA; PTTG1; PYGB; RPP25; SCPEP1; SLC46A3; SNX7; TPBG; XBP1 | 0.000713 |
| 19 | ANLN; ASPM; CDCA4; ERRFI1; GOLGA8A; LRP12; MAFF; PLK1; PNP; PPP1R13L; PRKCA; PTTG1; PYGB; RPP25; SCPEP1; SLC46A3; SNX7; TPBG; XBP1 | 0.000799 |
| 19 | ANLN; ASPM; CDCA4; ERRFI1; JAG1; LRP12; MAFF; PLK1; PNP; PPP1R13L; PRKCA; PTTG1; PYGB; RPP25; SCPEP1; SLC46A3; SNX7; TPBG; XBP1 | 0.001138 |
| 19 | ANLN; ASPM; CDCA4; GOLGA8A; JAG1; LRP12; MAFF; PLK1; PNP; PPP1R13L; PRKCA; PTTG1; PYGB; RPP25; SCPEP1; SLC46A3; SNX7; TPBG; XBP1 | 0.000746 |
| 19 | ANLN; ASPM; ERRFI1; GOLGA8A; JAG1; LRP12; MAFF; PLK1; PNP; PPP1R13L; PRKCA; PTTG1; PYGB; RPP25; SCPEP1; SLC46A3; SNX7; TPBG; XBP1 | 0.000683 |
| 19 | ANLN; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; SNX7; TPBG; XBP1 | 0.000703 |
| 19 | ASPM; CDCA4; ERRFI1; GOLGA8A; JAG1; LRP12; MAFF; PLK1; PNP; PPP1R13L; PRKCA; PTTG1; PYGB; RPP25; SCPEP1; SLC46A3; SNX7; TPBG; XBP1 | 0.000713 |
| 18 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG | 0.002825 |
| 18 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; XBP1 | 0.000642 |
| 18 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SLC46A3; TPBG; XBP1 | 0.001145 |
| 18 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SNX7; TPBG; XBP1 | 0.000616 |
| 18 | ANLN; ASPM; CDCA4; ERRFI1; GOLGA8A; JAG1; LRP12; PLK1; PNP; PPP1R13L; PRKCA; PTTG1; PYGB; RPP25; SLC46A3; SNX7; TPBG; XBP1 | 0.000662 |
| 18 | ANLN; ASPM; CDCA4; ERRFI1; GOLGA8A; JAG1; LRP12; PLK1; PNP; PPP1R13L; PRKCA; PTTG1; PYGB; SCPEP1; SLC46A3; SNX7; TPBG; XBP1 | 0.000719 |
| 18 | ANLN; ASPM; CDCA4; ERRFI1; GOLGA8A; JAG1; LRP12; PLK1; PNP; PPP1R13L; PRKCA; PTTG1; RPP25; SCPEP1; SLC46A3; SNX7; TPBG; XBP1 | 0.001771 |
| 18 | ANLN; ASPM; CDCA4; ERRFI1; GOLGA8A; JAG1; LRP12; PLK1; PNP; PPP1R13L; PRKCA; PYGB; RPP25; SCPEP1; SLC46A3; SNX7; TPBG; XBP1 | 0.000701 |
| 18 | ANLN; ASPM; CDCA4; ERRFI1; GOLGA8A; JAG1; LRP12; PLK1; PNP; PPP1R13L; PTTG1; PYGB; RPP25; SCPEP1; SLC46A3; SNX7; TPBG; XBP1 | 0.000659 |

| # genes | genes | cox_uva_p |
|---|---|---|
| 18 | ANLN; ASPM; CDCA4; ERRFI1; GOLGA8A; JAG1; LRP12; PLK1; PNP; PRKCA; PTTG1; PYGB; RPP25; SCPEP1; SLC46A3; SNX7; TPBG; XBP1 | 0.000641 |
| 18 | ANLN; ASPM; CDCA4; ERRFI1; GOLGA8A; JAG1; LRP12; PLK1; PPP1R13L; PRKCA; PTTG1; PYGB; RPP25; SCPEP1; SLC46A3; SNX7; TPBG; XBP1 | 0.000733 |
| 18 | ANLN; ASPM; CDCA4; ERRFI1; GOLGA8A; JAG1; LRP12; PNP; PPP1R13L; PRKCA; PTTG1; PYGB; RPP25; SCPEP1; SLC46A3; SNX7; TPBG; XBP1 | 0.00067 |
| 18 | ANLN; ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000656 |
| 18 | ANLN; ASPM; CDCA4; ERRFI1; GOLGA8A; LRP12; PLK1; PNP; PPP1R13L; PRKCA; PTTG1; PYGB; RPP25; SCPEP1; SLC46A3; SNX7; TPBG; XBP1 | 0.00073 |
| 18 | ANLN; ASPM; CDCA4; ERRFI1; JAG1; LRP12; PLK1; PNP; PPP1R13L; PRKCA; PTTG1; PYGB; RPP25; SCPEP1; SLC46A3; SNX7; TPBG; XBP1 | 0.001047 |
| 18 | ANLN; ASPM; CDCA4; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000686 |
| 18 | ANLN; ASPM; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000606 |
| 18 | ANLN; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000628 |
| 18 | ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000572 |
| 17 | ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG | 0.002725 |
| 17 | ASPM; CDCA4; ERRFI1; GOLGA8A; JAG1; LRP12; PLK1; PNP; PPP1R13L; PRKCA; PTTG1; PYGB; RPP25; SCPEP1; SLC46A3; SNX7; XBP1 | 0.000584 |
| 17 | ASPM; CDCA4; ERRFI1; GOLGA8A; JAG1; LRP12; PLK1; PNP; PPP1R13L; PRKCA; PTTG1; PYGB; RPP25; SCPEP1; SLC46A3; TPBG; XBP1 | 0.001141 |
| 17 | ASPM; CDCA4; ERRFI1; GOLGA8A; JAG1; LRP12; PLK1; PNP; PPP1R13L; PRKCA; PTTG1; PYGB; RPP25; SCPEP1; SNX7; TPBG; XBP1 | 0.000566 |
| 17 | ASPM; CDCA4; ERRFI1; GOLGA8A; JAG1; LRP12; PLK1; PNP; PPP1R13L; PRKCA; PTTG1; PYGB; RPP25; SLC46A3; SNX7; TPBG; XBP1 | 0.000588 |
| 17 | ASPM; CDCA4; ERRFI1; GOLGA8A; JAG1; LRP12; PLK1; PNP; PPP1R13L; PRKCA; PTTG1; PYGB; SCPEP1; SLC46A3; SNX7; TPBG; XBP1 | 0.000635 |
| 17 | ASPM; CDCA4; ERRFI1; GOLGA8A; JAG1; LRP12; PLK1; PNP; PPP1R13L; PRKCA; PTTG1; RPP25; SCPEP1; SLC46A3; SNX7; TPBG; XBP1 | 0.001249 |
| 17 | ASPM; CDCA4; ERRFI1; GOLGA8A; JAG1; LRP12; PLK1; PNP; PPP1R13L; PRKCA; PYGB; RPP25; SCPEP1; SLC46A3; SNX7; TPBG; XBP1 | 0.001246 |
| 17 | ASPM; CDCA4; ERRFI1; GOLGA8A; JAG1; LRP12; PLK1; PNP; PPP1R13L; PTTG1; PYGB; RPP25; SCPEP1; SLC46A3; SNX7; TPBG; XBP1 | 0.000597 |
| 17 | ASPM; CDCA4; ERRFI1; GOLGA8A; JAG1; LRP12; PLK1; PNP; PRKCA; PTTG1; PYGB; RPP25; SCPEP1; SLC46A3; SNX7; TPBG; XBP1 | 0.000578 |
| 17 | ASPM; CDCA4; ERRFI1; GOLGA8A; JAG1; LRP12; PLK1; PPP1R13L; PRKCA; PTTG1; PYGB; RPP25; SCPEP1; SLC46A3; SNX7; TPBG; XBP1 | 0.000672 |
| 17 | ASPM; CDCA4; ERRFI1; GOLGA8A; JAG1; LRP12; PNP; PPP1R13L; PRKCA; PTTG1; PYGB; RPP25; SCPEP1; SLC46A3; SNX7; TPBG; XBP1 | 0.000773 |
| 17 | ASPM; CDCA4; ERRFI1; GOLGA8A; JAG1; PLK1; PNP; PPP1R13L; PRKCA; PTTG1; PYGB; RPP25; SCPEP1; SLC46A3; SNX7; TPBG; XBP1 | 0.000637 |
| 17 | ASPM; CDCA4; ERRFI1; GOLGA8A; LRP12; PLK1; PNP; PPP1R13L; PRKCA; PTTG1; PYGB; RPP25; SCPEP1; SLC46A3; SNX7; TPBG; XBP1 | 0.000658 |
| 17 | ASPM; CDCA4; ERRFI1; JAG1; LRP12; PLK1; PNP; PPP1R13L; PRKCA; PTTG1; PYGB; RPP25; SCPEP1; SLC46A3; SNX7; TPBG; XBP1 | 0.001055 |
| 17 | ASPM; CDCA4; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000645 |
| 17 | ASPM; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000611 |
| 17 | CDCA4; ERRFI1; GOLGA8A; JAG1; LRP12; PLK1; PNP; PPP1R13L; PRKCA; PTTG1; PYGB; RPP25; SCPEP1; SLC46A3; SNX7; TPBG; XBP1 | 0.000574 |
| 16 | ASPM; CDCA4; ERRFI1; GOLGA8A; JAG1; LRP12; PLK1; PNP; PPP1R13L; PRKCA; PTTG1; PYGB; RPP25; SCPEP1; SNX7; TPBG | 0.002766 |
| 16 | ASPM; CDCA4; ERRFI1; GOLGA8A; JAG1; LRP12; PLK1; PNP; PPP1R13L; PRKCA; PTTG1; PYGB; RPP25; SCPEP1; SNX7; XBP1 | 0.000575 |
| 16 | ASPM; CDCA4; ERRFI1; GOLGA8A; JAG1; LRP12; PLK1; PNP; PPP1R13L; PRKCA; PTTG1; PYGB; RPP25; SCPEP1; TPBG; XBP1 | 0.001081 |
| 16 | ASPM; CDCA4; ERRFI1; GOLGA8A; JAG1; LRP12; PLK1; PNP; PPP1R13L; PRKCA; PTTG1; PYGB; RPP25; SNX7; TPBG; XBP1 | 0.000583 |
| 16 | ASPM; CDCA4; ERRFI1; GOLGA8A; JAG1; LRP12; PLK1; PNP; PPP1R13L; PRKCA; PTTG1; PYGB; SCPEP1; SNX7; TPBG; XBP1 | 0.00063 |
| 16 | ASPM; CDCA4; ERRFI1; GOLGA8A; JAG1; LRP12; PLK1; PNP; PPP1R13L; PRKCA; PTTG1; RPP25; SCPEP1; SNX7; TPBG; XBP1 | 0.001251 |
| 16 | ASPM; CDCA4; ERRFI1; GOLGA8A; JAG1; LRP12; PLK1; PNP; PPP1R13L; PRKCA; PYGB; RPP25; SCPEP1; SNX7; TPBG; XBP1 | 0.001253 |
| 16 | ASPM; CDCA4; ERRFI1; GOLGA8A; JAG1; LRP12; PLK1; PNP; PPP1R13L; PTTG1; PYGB; RPP25; SCPEP1; SNX7; TPBG; XBP1 | 0.000612 |
| 16 | ASPM; CDCA4; ERRFI1; GOLGA8A; JAG1; LRP12; PLK1; PNP; PRKCA; PTTG1; PYGB; RPP25; SCPEP1; SNX7; TPBG; XBP1 | 0.000601 |
| 16 | ASPM; CDCA4; ERRFI1; GOLGA8A; JAG1; LRP12; PLK1; PPP1R13L; PRKCA; PTTG1; PYGB; RPP25; SCPEP1; SNX7; TPBG; XBP1 | 0.000662 |

| # genes | genes | cox_uva_p |
|---|---|---|
| 16 | ASPM; CDCA4; ERRFI1; GOLGA8A; JAG1; LRP12; PNP; PPP1R13L; PRKCA; PTTG1; PYGB; RPP25; SCPEP1; SNX7; TPBG; XBP1 | 0.000782 |
| 16 | ASPM; CDCA4; ERRFI1; GOLGA8A; JAG1; PLK1; PNP; PPP1R13L; PRKCA; PTTG1; PYGB; RPP25; SCPEP1; SNX7; TPBG; XBP1 | 0.000609 |
| 16 | ASPM; CDCA4; ERRFI1; GOLGA8A; LRP12; PLK1; PNP; PPP1R13L; PRKCA; PTTG1; PYGB; RPP25; SCPEP1; SNX7; TPBG; XBP1 | 0.000652 |
| 16 | ASPM; CDCA4; ERRFI1; JAG1; LRP12; PLK1; PNP; PPP1R13L; PRKCA; PTTG1; PYGB; RPP25; SCPEP1; SNX7; TPBG; XBP1 | 0.001064 |
| 16 | ASPM; CDCA4; GOLGA8A; JAG1; LRP12; PLK1; PNP; PPP1R13L; PRKCA; PTTG1; PYGB; RPP25; SCPEP1; SNX7; TPBG; XBP1 | 0.000649 |
| 16 | ASPM; ERRFI1; GOLGA8A; JAG1; LRP12; PLK1; PNP; PPP1R13L; PRKCA; PTTG1; PYGB; RPP25; SCPEP1; SNX7; TPBG; XBP1 | 0.000626 |
| 16 | CDCA4; ERRFI1; GOLGA8A; JAG1; LRP12; PLK1; PNP; PPP1R13L; PRKCA; PTTG1; PYGB; RPP25; SCPEP1; SNX7; TPBG; XBP1 | 0.00057 |
| 15 | CDCA4; ERRFI1; GOLGA8A; JAG1; LRP12; PLK1; PNP; PPP1R13L; PRKCA; PTTG1; PYGB; RPP25; SCPEP1; SNX7; TPBG | 0.002742 |
| 15 | CDCA4; ERRFI1; GOLGA8A; JAG1; LRP12; PLK1; PNP; PPP1R13L; PRKCA; PTTG1; PYGB; RPP25; SCPEP1; SNX7; XBP1 | 0.000581 |
| 15 | CDCA4; ERRFI1; GOLGA8A; JAG1; LRP12; PLK1; PNP; PPP1R13L; PRKCA; PTTG1; PYGB; RPP25; SCPEP1; TPBG; XBP1 | 0.001101 |
| 15 | CDCA4; ERRFI1; GOLGA8A; JAG1; LRP12; PLK1; PNP; PPP1R13L; PRKCA; PTTG1; PYGB; RPP25; SNX7; TPBG; XBP1 | 0.000588 |
| 15 | CDCA4; ERRFI1; GOLGA8A; JAG1; LRP12; PLK1; PNP; PPP1R13L; PRKCA; PTTG1; PYGB; SCPEP1; SNX7; TPBG; XBP1 | 0.000635 |
| 15 | CDCA4; ERRFI1; GOLGA8A; JAG1; LRP12; PLK1; PNP; PPP1R13L; PRKCA; PTTG1; RPP25; SCPEP1; SNX7; TPBG; XBP1 | 0.001207 |
| 15 | CDCA4; ERRFI1; GOLGA8A; JAG1; LRP12; PLK1; PNP; PPP1R13L; PRKCA; PYGB; RPP25; SCPEP1; SNX7; TPBG; XBP1 | 0.001348 |
| 15 | CDCA4; ERRFI1; GOLGA8A; JAG1; LRP12; PLK1; PNP; PPP1R13L; PTTG1; PYGB; RPP25; SCPEP1; SNX7; TPBG; XBP1 | 0.000619 |
| 15 | CDCA4; ERRFI1; GOLGA8A; JAG1; LRP12; PLK1; PNP; PRKCA; PTTG1; PYGB; RPP25; SCPEP1; SNX7; TPBG; XBP1 | 0.000603 |
| 15 | CDCA4; ERRFI1; GOLGA8A; JAG1; LRP12; PLK1; PPP1R13L; PRKCA; PTTG1; PYGB; RPP25; SCPEP1; SNX7; TPBG; XBP1 | 0.000669 |
| 15 | CDCA4; ERRFI1; GOLGA8A; JAG1; LRP12; PNP; PPP1R13L; PRKCA; PTTG1; PYGB; RPP25; SCPEP1; SNX7; TPBG; XBP1 | 0.00081 |
| 15 | CDCA4; ERRFI1; GOLGA8A; JAG1; PLK1; PNP; PPP1R13L; PRKCA; PTTG1; PYGB; RPP25; SCPEP1; SNX7; TPBG; XBP1 | 0.000618 |
| 15 | CDCA4; ERRFI1; GOLGA8A; LRP12; PLK1; PNP; PPP1R13L; PRKCA; PTTG1; PYGB; RPP25; SCPEP1; SNX7; TPBG; XBP1 | 0.000657 |
| 15 | CDCA4; ERRFI1; JAG1; LRP12; PLK1; PNP; PPP1R13L; PRKCA; PTTG1; PYGB; RPP25; SCPEP1; SNX7; TPBG; XBP1 | 0.001079 |
| 15 | CDCA4; GOLGA8A; JAG1; LRP12; PLK1; PNP; PPP1R13L; PRKCA; PTTG1; PYGB; RPP25; SCPEP1; SNX7; TPBG; XBP1 | 0.000657 |
| 15 | ERRFI1; GOLGA8A; JAG1; LRP12; PLK1; PNP; PPP1R13L; PRKCA; PTTG1; PYGB; RPP25; SCPEP1; SNX7; TPBG; XBP1 | 0.00064 |
| 14 | CDCA4; ERRFI1; GOLGA8A; JAG1; LRP12; PLK1; PNP; PPP1R13L; PRKCA; PTTG1; PYGB; RPP25; SCPEP1; SNX7 | 0.002897 |
| 14 | CDCA4; ERRFI1; GOLGA8A; JAG1; LRP12; PLK1; PNP; PPP1R13L; PRKCA; PTTG1; PYGB; RPP25; SCPEP1; XBP1 | 0.00121 |
| 14 | CDCA4; ERRFI1; GOLGA8A; JAG1; LRP12; PLK1; PNP; PPP1R13L; PRKCA; PTTG1; PYGB; RPP25; SNX7; XBP1 | 0.000598 |
| 14 | CDCA4; ERRFI1; GOLGA8A; JAG1; LRP12; PLK1; PNP; PPP1R13L; PRKCA; PTTG1; PYGB; SCPEP1; SNX7; XBP1 | 0.000645 |
| 14 | CDCA4; ERRFI1; GOLGA8A; JAG1; LRP12; PLK1; PNP; PPP1R13L; PRKCA; PTTG1; RPP25; SCPEP1; SNX7; XBP1 | 0.00108 |
| 14 | CDCA4; ERRFI1; GOLGA8A; JAG1; LRP12; PLK1; PNP; PPP1R13L; PRKCA; PYGB; RPP25; SCPEP1; SNX7; XBP1 | 0.001433 |
| 14 | CDCA4; ERRFI1; GOLGA8A; JAG1; LRP12; PLK1; PNP; PPP1R13L; PTTG1; PYGB; RPP25; SCPEP1; SNX7; XBP1 | 0.000623 |
| 14 | CDCA4; ERRFI1; GOLGA8A; JAG1; LRP12; PLK1; PNP; PRKCA; PTTG1; PYGB; RPP25; SCPEP1; SNX7; XBP1 | 0.000645 |
| 14 | CDCA4; ERRFI1; GOLGA8A; JAG1; LRP12; PLK1; PPP1R13L; PRKCA; PTTG1; PYGB; RPP25; SCPEP1; SNX7; XBP1 | 0.000681 |
| 14 | CDCA4; ERRFI1; GOLGA8A; JAG1; LRP12; PNP; PPP1R13L; PRKCA; PTTG1; PYGB; RPP25; SCPEP1; SNX7; XBP1 | 0.000832 |
| 14 | CDCA4; ERRFI1; GOLGA8A; JAG1; PLK1; PNP; PPP1R13L; PRKCA; PTTG1; PYGB; RPP25; SCPEP1; SNX7; XBP1 | 0.000637 |
| 14 | CDCA4; ERRFI1; GOLGA8A; LRP12; PLK1; PNP; PPP1R13L; PRKCA; PTTG1; PYGB; RPP25; SCPEP1; SNX7; XBP1 | 0.000674 |
| 14 | CDCA4; ERRFI1; JAG1; LRP12; PLK1; PNP; PPP1R13L; PRKCA; PTTG1; PYGB; RPP25; SCPEP1; SNX7; XBP1 | 0.0011 |
| 14 | CDCA4; GOLGA8A; JAG1; LRP12; PLK1; PNP; PPP1R13L; PRKCA; PTTG1; PYGB; RPP25; SCPEP1; SNX7; XBP1 | 0.000676 |
| 14 | ERRFI1; GOLGA8A; JAG1; LRP12; PLK1; PNP; PPP1R13L; PRKCA; PTTG1; PYGB; RPP25; SCPEP1; SNX7; XBP1 | 0.000652 |

-continued

| # genes | genes | cox_uva_p |
|---|---|---|
| 13 | CDCA4; ERRFI1; GOLGA8A; JAG1; LRP12; PLK1; PNP; PPP1R13L; PRKCA; PTTG1; PYGB; RPP25; SNX7 | 0.002962 |
| 13 | CDCA4; ERRFI1; GOLGA8A; JAG1; LRP12; PLK1; PNP; PPP1R13L; PRKCA; PTTG1; PYGB; RPP25; XBP1 | 0.001243 |
| 13 | CDCA4; ERRFI1; GOLGA8A; JAG1; LRP12; PLK1; PNP; PPP1R13L; PRKCA; PTTG1; PYGB; SNX7; XBP1 | 0.000665 |
| 13 | CDCA4; ERRFI1; GOLGA8A; JAG1; LRP12; PLK1; PNP; PPP1R13L; PRKCA; PTTG1; RPP25; SNX7; XBP1 | 0.001119 |
| 13 | CDCA4; ERRFI1; GOLGA8A; JAG1; LRP12; PLK1; PNP; PPP1R13L; PRKCA; PYGB; RPP25; SNX7; XBP1 | 0.001484 |
| 13 | CDCA4; ERRFI1; GOLGA8A; JAG1; LRP12; PLK1; PNP; PPP1R13L; PTTG1; PYGB; RPP25; SNX7; XBP1 | 0.00064 |
| 13 | CDCA4; ERRFI1; GOLGA8A; JAG1; LRP12; PLK1; PNP; PRKCA; PTTG1; PYGB; RPP25; SNX7; XBP1 | 0.000664 |
| 13 | CDCA4; ERRFI1; GOLGA8A; JAG1; LRP12; PLK1; PPP1R13L; PRKCA; PTTG1; PYGB; RPP25; SNX7; XBP1 | 0.000701 |
| 13 | CDCA4; ERRFI1; GOLGA8A; JAG1; LRP12; PNP; PPP1R13L; PRKCA; PTTG1; PYGB; RPP25; SNX7; XBP1 | 0.000859 |
| 13 | CDCA4; ERRFI1; GOLGA8A; JAG1; PLK1; PNP; PPP1R13L; PRKCA; PTTG1; PYGB; RPP25; SNX7; XBP1 | 0.000657 |
| 13 | CDCA4; ERRFI1; GOLGA8A; LRP12; PLK1; PNP; PPP1R13L; PRKCA; PTTG1; PYGB; RPP25; SNX7; XBP1 | 0.000694 |
| 13 | CDCA4; ERRFI1; JAG1; LRP12; PLK1; PNP; PPP1R13L; PRKCA; PTTG1; PYGB; RPP25; SNX7; XBP1 | 0.001133 |
| 13 | CDCA4; GOLGA8A; JAG1; LRP12; PLK1; PNP; PPP1R13L; PRKCA; PTTG1; PYGB; RPP25; SNX7; XBP1 | 0.000697 |
| 13 | ERRFI1; GOLGA8A; JAG1; LRP12; PLK1; PNP; PPP1R13L; PRKCA; PTTG1; PYGB; RPP25; SNX7; XBP1 | 0.000674 |
| 12 | CDCA4; ERRFI1; GOLGA8A; JAG1; LRP12; PLK1; PNP; PPP1R13L; PTTG1; PYGB; RPP25; SNX7 | 0.003435 |
| 12 | CDCA4; ERRFI1; GOLGA8A; JAG1; LRP12; PLK1; PNP; PPP1R13L; PTTG1; PYGB; RPP25; XBP1 | 0.001587 |
| 12 | CDCA4; ERRFI1; GOLGA8A; JAG1; LRP12; PLK1; PNP; PPP1R13L; PTTG1; PYGB; SNX7; XBP1 | 0.00068 |
| 12 | CDCA4; ERRFI1; GOLGA8A; JAG1; LRP12; PLK1; PNP; PPP1R13L; PTTG1; RPP25; SNX7; XBP1 | 0.001094 |
| 12 | CDCA4; ERRFI1; GOLGA8A; JAG1; LRP12; PLK1; PNP; PPP1R13L; PYGB; RPP25; SNX7; XBP1 | 0.001517 |
| 12 | CDCA4; ERRFI1; GOLGA8A; JAG1; LRP12; PLK1; PNP; PTTG1; PYGB; RPP25; SNX7; XBP1 | 0.000643 |
| 12 | CDCA4; ERRFI1; GOLGA8A; JAG1; LRP12; PLK1; PPP1R13L; PTTG1; PYGB; RPP25; SNX7; XBP1 | 0.000751 |
| 12 | CDCA4; ERRFI1; GOLGA8A; JAG1; LRP12; PNP; PPP1R13L; PTTG1; PYGB; RPP25; SNX7; XBP1 | 0.000898 |
| 12 | CDCA4; ERRFI1; GOLGA8A; JAG1; PLK1; PNP; PPP1R13L; PTTG1; PYGB; RPP25; SNX7; XBP1 | 0.000691 |
| 12 | CDCA4; ERRFI1; GOLGA8A; LRP12; PLK1; PNP; PPP1R13L; PTTG1; PYGB; RPP25; SNX7; XBP1 | 0.000755 |
| 12 | CDCA4; ERRFI1; JAG1; LRP12; PLK1; PNP; PPP1R13L; PTTG1; PYGB; RPP25; SNX7; XBP1 | 0.001177 |
| 12 | CDCA4; GOLGA8A; JAG1; LRP12; PLK1; PNP; PPP1R13L; PTTG1; PYGB; RPP25; SNX7; XBP1 | 0.000783 |
| 12 | ERRFI1; GOLGA8A; JAG1; LRP12; PLK1; PNP; PPP1R13L; PTTG1; PYGB; RPP25; SNX7; XBP1 | 0.00068 |
| 11 | CDCA4; ERRFI1; GOLGA8A; JAG1; LRP12; PLK1; PNP; PTTG1; PYGB; RPP25; SNX7 | 0.003971 |
| 11 | CDCA4; ERRFI1; GOLGA8A; JAG1; LRP12; PLK1; PNP; PTTG1; PYGB; RPP25; XBP1 | 0.001197 |
| 11 | CDCA4; ERRFI1; GOLGA8A; JAG1; LRP12; PLK1; PNP; PTTG1; PYGB; SNX7; XBP1 | 0.000679 |
| 11 | CDCA4; ERRFI1; GOLGA8A; JAG1; LRP12; PLK1; PNP; PTTG1; RPP25; SNX7; XBP1 | 0.001064 |
| 11 | CDCA4; ERRFI1; GOLGA8A; JAG1; LRP12; PLK1; PNP; PYGB; RPP25; SNX7; XBP1 | 0.001314 |
| 11 | CDCA4; ERRFI1; GOLGA8A; JAG1; LRP12; PLK1; PTTG1; PYGB; RPP25; SNX7; XBP1 | 0.000734 |
| 11 | CDCA4; ERRFI1; GOLGA8A; JAG1; LRP12; PNP; PTTG1; PYGB; RPP25; SNX7; XBP1 | 0.000908 |
| 11 | CDCA4; ERRFI1; GOLGA8A; JAG1; PLK1; PNP; PTTG1; PYGB; RPP25; SNX7; XBP1 | 0.000646 |
| 11 | CDCA4; ERRFI1; GOLGA8A; LRP12; PLK1; PNP; PTTG1; PYGB; RPP25; SNX7; XBP1 | 0.000759 |
| 11 | CDCA4; ERRFI1; JAG1; LRP12; PLK1; PNP; PTTG1; PYGB; RPP25; SNX7; XBP1 | 0.001152 |
| 11 | CDCA4; GOLGA8A; JAG1; LRP12; PLK1; PNP; PTTG1; PYGB; RPP25; SNX7; XBP1 | 0.000793 |
| 11 | ERRFI1; GOLGA8A; JAG1; LRP12; PLK1; PNP; PTTG1; PYGB; RPP25; SNX7; XBP1 | 0.000718 |
| 10 | CDCA4; ERRFI1; GOLGA8A; JAG1; PLK1; PNP; PTTG1; PYGB; RPP25; SNX7 | 0.003926 |
| 10 | CDCA4; ERRFI1; GOLGA8A; JAG1; PLK1; PNP; PTTG1; PYGB; RPP25; XBP1 | 0.001287 |
| 10 | CDCA4; ERRFI1; GOLGA8A; JAG1; PLK1; PNP; PTTG1; PYGB; SNX7; XBP1 | 0.000686 |

| # genes | genes | cox_uva_p |
|---|---|---|
| 10 | CDCA4; ERRFI1; GOLGA8A; JAG1; PLK1; PNP; PTTG1; RPP25; SNX7; XBP1 | 0.000901 |
| 10 | CDCA4; ERRFI1; GOLGA8A; JAG1; PLK1; PNP; PYGB; RPP25; SNX7; XBP1 | 0.001446 |
| 10 | CDCA4; ERRFI1; GOLGA8A; JAG1; PLK1; PTTG1; PYGB; RPP25; SNX7; XBP1 | 0.000749 |
| 10 | CDCA4; ERRFI1; GOLGA8A; JAG1; PNP; PTTG1; PYGB; RPP25; SNX7; XBP1 | 0.000944 |
| 10 | CDCA4; ERRFI1; GOLGA8A; PLK1; PNP; PTTG1; PYGB; RPP25; SNX7; XBP1 | 0.000777 |
| 10 | CDCA4; ERRFI1; JAG1; PLK1; PNP; PTTG1; PYGB; RPP25; SNX7; XBP1 | 0.001155 |
| 10 | CDCA4; GOLGA8A; JAG1; PLK1; PNP; PTTG1; PYGB; RPP25; SNX7; XBP1 | 0.000799 |
| 10 | ERRFI1; GOLGA8A; JAG1; PLK1; PNP; PTTG1; PYGB; RPP25; SNX7; XBP1 | 0.000734 |
| 9 | CDCA4; ERRFI1; GOLGA8A; JAG1; PLK1; PNP; PTTG1; PYGB; SNX7 | 0.004189 |
| 9 | CDCA4; ERRFI1; GOLGA8A; JAG1; PLK1; PNP; PTTG1; PYGB; XBP1 | 0.001396 |
| 9 | CDCA4; ERRFI1; GOLGA8A; JAG1; PLK1; PNP; PTTG1; SNX7; XBP1 | 0.001044 |
| 9 | CDCA4; ERRFI1; GOLGA8A; JAG1; PLK1; PNP; PYGB; SNX7; XBP1 | 0.001551 |
| 9 | CDCA4; ERRFI1; GOLGA8A; JAG1; PLK1; PTTG1; PYGB; SNX7; XBP1 | 0.000802 |
| 9 | CDCA4; ERRFI1; GOLGA8A; JAG1; PNP; PTTG1; PYGB; SNX7; XBP1 | 0.001016 |
| 9 | CDCA4; ERRFI1; GOLGA8A; PLK1; PNP; PTTG1; PYGB; SNX7; XBP1 | 0.00082 |
| 9 | CDCA4; ERRFI1; JAG1; PLK1; PNP; PTTG1; PYGB; SNX7; XBP1 | 0.001267 |
| 9 | CDCA4; GOLGA8A; JAG1; PLK1; PNP; PTTG1; PYGB; SNX7; XBP1 | 0.000839 |
| 9 | ERRFI1; GOLGA8A; JAG1; PLK1; PNP; PTTG1; PYGB; SNX7; XBP1 | 0.00079 |
| 8 | ERRFI1; GOLGA8A; JAG1; PLK1; PNP; PTTG1; PYGB; SNX7 | 0.004579 |
| 8 | ERRFI1; GOLGA8A; JAG1; PLK1; PNP; PTTG1; PYGB; XBP1 | 0.001341 |
| 8 | ERRFI1; GOLGA8A; JAG1; PLK1; PNP; PTTG1; SNX7; XBP1 | 0.001313 |
| 8 | ERRFI1; GOLGA8A; JAG1; PLK1; PNP; PYGB; SNX7; XBP1 | 0.00233 |
| 8 | ERRFI1; GOLGA8A; JAG1; PLK1; PTTG1; PYGB; SNX7; XBP1 | 0.000935 |
| 8 | ERRFI1; GOLGA8A; JAG1; PNP; PTTG1; PYGB; SNX7; XBP1 | 0.001364 |
| 8 | ERRFI1; GOLGA8A; PLK1; PNP; PTTG1; PYGB; SNX7; XBP1 | 0.000939 |
| 8 | ERRFI1; JAG1; PLK1; PNP; PTTG1; PYGB; SNX7; XBP1 | 0.001587 |
| 8 | GOLGA8A; JAG1; PLK1; PNP; PTTG1; PYGB; SNX7; XBP1 | 0.00098 |
| 7 | ERRFI1; GOLGA8A; JAG1; PLK1; PTTG1; PYGB; SNX7 | 0.005196 |
| 7 | ERRFI1; GOLGA8A; JAG1; PLK1; PTTG1; PYGB; XBP1 | 0.001705 |
| 7 | ERRFI1; GOLGA8A; JAG1; PLK1; PTTG1; SNX7; XBP1 | 0.001535 |
| 7 | ERRFI1; GOLGA8A; JAG1; PLK1; PYGB; SNX7; XBP1 | 0.002871 |
| 7 | ERRFI1; GOLGA8A; JAG1; PTTG1; PYGB; SNX7; XBP1 | 0.001635 |
| 7 | ERRFI1; GOLGA8A; PLK1; PTTG1; PYGB; SNX7; XBP1 | 0.001107 |
| 7 | ERRFI1; JAG1; PLK1; PTTG1; PYGB; SNX7; XBP1 | 0.001909 |
| 7 | GOLGA8A; JAG1; PLK1; PTTG1; PYGB; SNX7; XBP1 | 0.001165 |
| 6 | ERRFI1; GOLGA8A; PLK1; PTTG1; PYGB; SNX7 | 0.006268 |
| 6 | ERRFI1; GOLGA8A; PLK1; PTTG1; PYGB; XBP1 | 0.002066 |
| 6 | ERRFI1; GOLGA8A; PLK1; PTTG1; SNX7; XBP1 | 0.001841 |
| 6 | ERRFI1; GOLGA8A; PLK1; PYGB; SNX7; XBP1 | 0.003342 |
| 6 | ERRFI1; GOLGA8A; PTTG1; PYGB; SNX7; XBP1 | 0.001914 |
| 6 | ERRFI1; PLK1; PTTG1; PYGB; SNX7; XBP1 | 0.002243 |
| 6 | GOLGA8A; PLK1; PTTG1; PYGB; SNX7; XBP1 | 0.00138 |
| 5 | GOLGA8A; PLK1; PTTG1; PYGB; SNX7 | 0.007952 |
| 5 | GOLGA8A; PLK1; PTTG1; PYGB; XBP1 | 0.002872 |
| 5 | GOLGA8A; PLK1; PTTG1; SNX7; XBP1 | 0.001994 |
| 5 | GOLGA8A; PLK1; PYGB; SNX7; XBP1 | 0.004417 |
| 5 | GOLGA8A; PTTG1; PYGB; SNX7; XBP1 | 0.002451 |
| 5 | PLK1; PTTG1; PYGB; SNX7; XBP1 | 0.002803 |
| 4 | GOLGA8A; PLK1; PTTG1; SNX7 | 0.012094 |
| 4 | GOLGA8A; PLK1; PTTG1; XBP1 | 0.001625 |
| 4 | GOLGA8A; PLK1; SNX7; XBP1 | 0.002487 |
| 4 | GOLGA8A; PTTG1; SNX7; XBP1 | 0.003022 |
| 4 | PLK1; PTTG1; SNX7; XBP1 | 0.004507 |
| 3 | GOLGA8A; PLK1; PTTG1 | 0.023815 |
| 3 | GOLGA8A; PLK1; XBP1 | 0.00182 |
| 3 | GOLGA8A; PTTG1; XBP1 | 0.002344 |
| 3 | PLK1; PTTG1; XBP1 | 0.004261 |
| 2 | GOLGA8A; PLK1 | 0.006444 |
| 2 | GOLGA8A; XBP1 | 0.011472 |
| 2 | PLK1; XBP1 | 0.012748 |
| 1 | GOLGA8A | 0.03454 |
| 1 | PLK1 | 0.042617 |

The invention claimed is:

1. A method of treatment of a subject with lung cancer comprising the steps of predicting a level of risk of mortality for a subject with lung cancer the method comprising:
 (a) contacting a biological sample from the subject with reagents that specifically bind to each member of a panel of biomarkers consisting of ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, and XBP1;
 (b) determining a risk score of the subject based on the nucleic acid levels of expression of the biomarkers in the samples;
 (c) comparing the risk score to a threshold to predict whether the subject is at high or low risk of mortality;
 (d) selecting a treatment from surgical treatment, chemotherapy, radiotherapy, immunotherapy or CAR-T therapy,
  wherein for a subject at low risk of mortality the selected treatment is surgical treatment alone, and wherein for a subject at high risk of mortality the selected treatment is surgical treatment, and chemotherapy, radiotherapy, immunotherapy or CAR-T therapy; and (e) administering the treatment.

2. The method of claim 1 wherein determining a risk score of the subject comprises:

for each of the biomarkers, determining a score indicative of nucleic acid levels of expression in the tissue sample;

calculating a risk score based on the determined scores, wherein the risk score is calculated by summing weighted biomarker scores, wherein the biomarker scores are based on the determined scores and each biomarker score has an associated weight; and comparing the risk score to a threshold.

3. The method of claim 2 wherein the associated weight for each of the biomarker scores for GOLGA8A, SCPEP1, SLC46A3 and XBP1 has a negative value and the associated weight for the biomarker score for ANLN, ASPM, CDCA4, ERRFI1, FURIN, ITGA6, JAG1, LRP12, MAFF, MRPS17, PLK1, PNP, PPP1R13L, PRKCA, PTTG1, PYGB, RPP25, SNX7 and TPBG has a positive value.

4. The method of claim 2, wherein the weighted sum for the risk score is:

$$riskscore = b_1 x_{1i} + b_2 x_{2i} + \ldots + b_n x_{ni}$$

where $x_{1i}, x_{2i}, \ldots, x_{ni}$ are the biomarker scores for the four selected biomarkers for each subject i and $b_1, b_2, \ldots, b_n$ are a set of associated weights for each biomarker score.

5. The method of claim 4, further comprising determining the weights for the weighted sum using a Cox proportional hazard model which is trained using training data comprising information on a plurality of biomarkers in a set of subjects.

6. The method of claim 5, further comprising identifying the plurality of biomarkers to be used in the Cox proportional hazard model, wherein the plurality of biomarkers are selected from the group comprising ANLN, ASPM, CDCA4, ERRFI1, FURIN, GOLGA8A, ITGA6, JAG1, LRP12, MAFF, MRPS17, PLK1, PNP, PPP1R13L, PRKCA, PTTG1, PYGB, RPP25, SCPEP1, SLC46A3, SNX7, TPBG, and XBP1.

7. The method of claim 5, wherein the threshold is the median risk score for the training data.

8. The method of claim 2, wherein determining a biomarker score indicative of a level of the biomarker comprises determining a scaled intensity score.

9. The method of claim 8, wherein the biomarker score is based on the scaled intensity score which has been adjusted by subtracting an adjustment factor.

10. The method of claim 2, wherein determining a score indicative of a level of the biomarker comprises awarding a first value when the level is above a threshold and a second value when the level is below the threshold.

11. The method of claim 2, wherein determining a score indicative of a level of the biomarker comprises awarding a first value when the level is above an upper threshold, a second value when the level is below the upper threshold but above a lower threshold and a third value when the level is below the lower threshold.

12. The method of claim 1, wherein the reagents are nucleic acids.

13. The method of claim 1, wherein the lung cancer is non-small lung cancer (NSCLC).

14. The method of claim 13 wherein the NSCLC is selected from invasive adenocarcinoma (LUAD), squamous cell carcinoma (LUSC), large cell carcinoma, adenosquamous carcinoma, carcinosarcoma or large cell neuroendocrine.

* * * * *